US007863029B2

(12) United States Patent
Jaffe

(10) Patent No.: US 7,863,029 B2
(45) Date of Patent: Jan. 4, 2011

(54) ALTERNATE MORPHEEINS OF ALLOSTERIC PROTEINS AS A TARGET FOR THE DEVELOPMENT OF BIOACTIVE MOLECULES

(75) Inventor: Eileen K. Jaffe, Jenkintown, PA (US)

(73) Assignee: Fox Chase Cancer Center, Jenkintown, PA (US)

( * ) Notice: Subject to any disclaimer, the term of this patent is extended or adjusted under 35 U.S.C. 154(b) by 0 days.

(21) Appl. No.: 12/106,498

(22) Filed: Apr. 21, 2008

(65) Prior Publication Data

US 2008/0286847 A1    Nov. 20, 2008

Related U.S. Application Data

(60) Division of application No. 11/327,762, filed on Jan. 6, 2006, now abandoned, which is a continuation-in-part of application No. PCT/US2004/021722, filed on Jul. 7, 2004.

(60) Provisional application No. 60/577,312, filed on Jun. 4, 2004, provisional application No. 60/690,649, filed on Jun. 15, 2005.

(51) Int. Cl.
 *C07K 14/00* (2006.01)
 *C12N 9/99* (2006.01)
 *C12N 9/10* (2006.01)
(52) U.S. Cl. .................. 435/184; 435/189; 435/193; 435/194; 435/196; 435/232; 530/402
(58) Field of Classification Search .............. 514/6, 514/569; 800/278; 435/193, 184, 189, 194, 435/196, 232; 530/402
See application file for complete search history.

(56) References Cited

U.S. PATENT DOCUMENTS

| 4,879,236 | A  | 11/1989 | Smith et al. |
| 5,061,620 | A  | 10/1991 | Tsukamoto et al. |
| 5,583,973 | A  | 12/1996 | DeLisi et al. |
| 5,612,894 | A  | 3/1997  | Wertz |
| 5,681,559 | A  | 10/1997 | DiGiusto et al. |
| 5,871,986 | A  | 2/1999  | Boyce |
| 6,140,363 | A  | 10/2000 | Hur et al. |
| 6,335,195 | B1 | 1/2002  | Rodgers |
| 6,645,489 | B2 | 11/2003 | Pykett et al. |
| 6,667,064 | B2 | 12/2003 | Surette |
| 6,689,372 | B1 | 2/2004  | Holzl |
| 6,740,311 | B2 | 3/2004  | White, Jr. |
| 2006/0162014 | A1 | 7/2006 | Jaffe |

FOREIGN PATENT DOCUMENTS

| WO | WO9007861 | 7/1990 |
| WO | WO9110741 | 7/1991 |
| WO | WO9117271 | 11/1991 |
| WO | WO9118980 | 12/1991 |
| WO | WO9201047 | 1/1992 |
| WO | 9204449 A1 | 3/1992 |
| WO | 9206201 A1 | 4/1992 |
| WO | WO9306121 | 4/1993 |
| WO | WO9312227 | 6/1993 |
| WO | 9319189 A1 | 9/1993 |
| WO | WO9319189 | 9/1993 |
| WO | WO9408051 | 4/1994 |
| WO | WO8402913 | 8/1994 |
| WO | WO9512608 | 5/1995 |
| WO | WO9530642 | 11/1995 |
| WO | WO9535503 | 12/1995 |
| WO | WO2005007817 | 1/2005 |

OTHER PUBLICATIONS

Horsch, R.B. and Klee, H.J. (1986) Rapid assay of foreign gene expression in leaf discs transformed by agrobacterium tumefaciens: Role of T-DNA borders in the transfer process. Proc. Natl. Acad. Sci. U S A 83 (12), 4428-4432.
Hayashimoto, A. et al. (1990) A polyethylene glycol-mediated protoplast transformation system for production of fertile transgenic rice plants. Plant Physiol. 93, 857-863.
Wetmur, J.G. et al. (1986) Human delta-aminolevulinate dehydratase: nucleotide sequence of a full-length cDNA clone. Proc Natl Acad Sci U S A 83 (20), 7703-7707.
Jaffe, E.K. et al. (2001) The molecular mechanism of lead inhibition of human porphobilinogen synthase. J Biol Chem 276 (2), 1531-1537.
Frankenberg, N. et al. (1999) Pseudomonas aeruginosa contains a novel type V porphobilinogen synthase with no required catalytic metal ions. Biochemistry 38 (42), 13976-13982.
Erskine, P.T. et al. (2001) The x-ray structure of yeast 5-aminolaevulinic acid dehydratase complexed with substrate and three inhibitors. J Mol Biol 312 (1), 133-141.
Erskine, P.T. et al. (2000) MAD analyses of yeast 5-aminolaevulinate dehydratase: their use in structure determination and in defining the metal-binding sites. Acta Crystallogr D Biol Crystallogr 56 ( Pt 4), 421-430.
Erskine, P.T. et al. (1997) X-ray structure of 5-aminolaevulinate dehydratase, a hybrid aldolase. Nat Struct Biol 4 (12), 1025-1031.
Erskine, P.T. et al. (1999) X-ray structure of 5-aminolevulinic acid dehydratase from *Escherichia coli* complexed with the inhibitor levulinic acid at 2.0 A resolution. Biochemistry 38 (14), 4266-4276.

(Continued)

*Primary Examiner*—Chih-Min Kam
(74) *Attorney, Agent, or Firm*—Caesar, Rivise, Bernstein, Cohen & Pokotilow, Ltd.

(57) ABSTRACT

A composition having an agent adapted to affect a multimeric protein by binding to a binding site of the multimeric protein and thereby affecting an equilibrium of units, wherein the multimeric protein has an assembly having a plurality of said units, wherein each of the units has a first complementary surface and a second complementary surface and wherein the first complementary surface of one unit is associated with the second complementary surface of another unit, provided that the assembly is at least one of different quaternary isoforms on a condition that in the multimeric protein (1) a structure of each of the units determines a structure of the different quaternary isoforms, (2) the units are in the equilibrium and (3) the structure of the different quaternary isoforms influences a function of the multimeric protein.

4 Claims, 39 Drawing Sheets

OTHER PUBLICATIONS

Erskine, P.T. et al. (1999) The Schiff base complex of yeast 5-aminolaevulinic acid dehydratase with laevulinic acid. Protein Sci 8 (6), 1250-1256.

Jaffe, E.K. et al. (2002) Species-specific inhibition of porphobilinogen synthase by 4-oxosebacic acid. J Biol Chem 277 (22), 19792-19799.

Murzin, A.G. et al. (1995) SCOP: a structural classification of proteins database for the investigation of sequences and structures. J Mol Biol 247 (4), 536-540.

Schonfeld, H.J. et al. (1998) Quasi-elastic light scattering and analytical ultracentrifugation are indispensable tools for the purification and characterization of recombinant proteins. Biochem. Soc. Trans. 26 (4), 753-758.

Wu, H. et al. (1997) Dimeric association and segmental variability in the structure of human CD4. Nature 387 (6632), 527-530.

Moradian-Oldak, J. et al. (1998) Temperature and pH-dependent supramolecular self-assembly of amelogenin molecules: a dynamic light-scattering analysis. J. Struct. Biol. 122 (3), 320-327.

Gast, K. et al. (1997) Ribonuclease T1 has different dimensions in the thermally and chemically denatured states: a dynamic light scattering study. FEBS Lett. 403 (3), 245-248.

Ferre-D'Amare, A.R. and Burley, S.K. (1997) Dynamic light scattering in evaluation crystallizability of macromolecules. Methods Enzymol. 276, 157-166.

Canutescu, A.A. and Dunbrack, R.L., Jr. (2005) MoIIDE (Molecular Integrated Development Environment): a homology modeling framework you can click with. Bioinformatics.

Xiang, Z. et al. (2002) Evaluating conformational free energies: the colony energy and its application to the problem of loop prediction. Proc. Natl. Acad. Sci. US 99, 7432-7437.

Canutescu, A.A. et al. (2003) A graph-theory algorithm for rapid protein side-chain prediction. Protein Sci 12 (9), 2001-2014.

Shankar, S. et al. (1995) Exopolysaccharide alginate synthesis in Pseudomonas aeruginosa: enzymology and regulation of gene expression. Adv Enzymol Relat Areas Mol Biol 70, 221-255.

Roychoudhury, S. et al. (1989) Purification and characterization of guanosine diphospho D-mannose dehydrogenase. A key enzyme in the biosynthesis of alginate b Pseudomona aeruginosa. J Biol Chem 264 (16), 9380-9385.

Fieulaine, S. et al. (2001) X-ray structure of HPr kinase: a bacterial protein kinase with a P-loop nucleotide-binding domain. Embo J 20 (15), 3917-3927.

Marquez, J.A. et al. (2002) Structure of the full-length HPr kinase/phosphatase from Staphylococcus xylosus at 1.95 A resolution: Mimicking the product/substrate of the phospho transfer reactions. Proc Natl Acad Sci U S A 99 (6), 3458-3463.

Allen, G.S. et al. (2003) Crystal structure of HPr kinase/phosphatase from Mycoplasma pneumoniae. J Mol Biol 326 (4), 1203-1217.

Ramstrom, H. et al. (2003) Properties and regulation of the bifunctional enzyme HPr kinase/phosphatase in Bacillus subtilis. J Biol Chem 278 (2), 1174-1185.

Jault, J.M. et al. (2000) The HPr kinase from Bacillus subtilis is a homo-oligomeric enzyme which exhibits strong positive cooperativity for nucleotide and fructose 1,6-bisphosphate binding. J Biol Chem 275 (3), 1773-1780.

Caspar, D.L. and Klug, A. (1962) Physical principles in the construction of regular viruses. Cold Spring Harb Symp Quant Biol 27, 1-24.

Suzuki, M. et al. (1994) Isolation and characterization of two tightly linked catalase genes from castor bean that are differentially regulated. Plant Mol. Biol. 25 (3), 507-516.

Herrera-Estrella, L. et al. (1983) Expression of chimaeric genes transferred into plant cells using a Ti-plasmid-derived vector. Nature 303, 209-213.

Bevan, M. (1984) Binary Arobacterium vectors for plant transformation. Nucleic Acids Res. 12 (22), 8711-8721.

Rogers, S.G. et al. (1987) Improved vectors for plant transformation: expression cassette vectors and new slectable markers, San Diego: Academic Press.

Wang, ZX, Kinetic study on the dimer-tetramer interconversion of glycogen phosphorylase a, European Journal of Biochmistry, Feb. 1999, vol. 259, 609-617.

Anfinsen, C.B. (1973) Principles that govern the folding of protein chains. Science 181 (96), 223-230.

Morgan, G.J. (2003) Historical review: viruses, crystals and geodesic domes. Trends Biochem Sci 28 (2), 86-90.

Koshland, D.E., Jr. et al. (1966) Comparison of experimental binding data and theoretical models in proteins containing subunits. Biochemistry 5 (1), 365-385.

Monod, J. et al. (1965) on the Nature of Allosteric Transitions: A Plausible Model. J Mol Biol 12, 88-118.

Jordan, P.M. (1994) Highlights in haem biosynthesis. Curr Opin Struct Biol 4 (6), 902-911.

Battersby, A.R. and Leeper, F.J. (1997) Biosynthesis of vitamin B12. Topics in Current Chemistry 195(Biosynthesis: Polyketides and Vitamins), 143-193.

Battersby, A.R. (2000) Tetrapyrroles: the pigments of life. Nat Prod Rep 17 (6), 507-526.

Jaffe, E.K. (2000) The porphobilinogen synthase family of metalloenzymes. Acta Crystallogr D Biol Crystallogr 56 ( Pt 2), 115-128.

Berman, H.M. et al. (2000) The Protein Data Bank. Nucleic Acids Res 28 (1), 235-242.

Jaffe, E.K. (2003) An unusual phylogenetic variation in the metal ion binding sites of porphobilinogen synthase. Chem Biol 10 (1), 25-34.

Jaffe, E.K. and Hanes, D. (1986) Dissection of the early steps in the porphobilinogen synthase catalyzed reaction. Requirements for Schiff's base formation. J Biol Chem 261 (20), 9348-9353.

Kervinen, J. et al. (2000) Porphobilinogen synthase from pea: expression from an artificial gene, kinetic characterization, and novel implications for subunit interactions. Biochemistry 39 (30), 9018-9029.

Petrovich, R.M. et al. (1996) Bradyrhizobium japonicum porphobilinogen synthase uses two Mg(II) and monovalent cations. J Biol Chem 271 (15), 8692-8699.

Bollivar, D.W. et al. (2004) Rhodobacter capsulatus porphobilinogen synthase, a high activity metal ion independent hexamer. BMC Biochem 5 (1), 17.

Kundrat, L. et al. (2003) A structural basis for half-of-the-sites metal binding revealed in Drosophila melanogaster porphobilinogen synthase. J. Biol. Chem. 278 (33), 31325-31330.

Bevan, D.R. et al. (1980) Mechanism of porphobilinogen synthase. Requirement of Zn2+ for enzyme activity. J Biol Chem 255 (5), 2030-2035.

Snook, C.F. et al. (2003) Crystal structure of GDP-mannose dehydrogenase: a key enzyme of alginate biosynthesis in P. aeruginosa. Biochemistry 42 (16), 4658-4668.

Naught, L.E. et al. (2002) Allosterism and cooperativity in Pseudomonas aeruginosa GDP-mannose dehydrogenase. Biochemistry 41 (30), 9637-9645.

Poncet, S. et al. (2004) HPr kinase/phosphorylase, a Walker motif A-containing bifunctional sensor enzyme controlling catabolite repression in Gram-positive bacteria. Biochim Biophys Acta 1697 (1-2), 123-135.

Rochet, J.C. et al (2000) Pig heart CoA transferase exists as two oligomeric forms separated by a large kinetic barrier. Biochemistry 39 (37), 11291-11302.

Bzowska, A. et al. (1995) Calf spleen purine nucleoside phosphorylase: purification, sequence and crystal structure of its complex with an N(7)-acycloguanosine inhibitor. FEBS Lett 367 (3), 214-218.

Koellner, G. et al. (1998) Crystal structure of the ternary complex of E. coli purine nucleoside phosphorylase with formycin B, a structural analogue of the substrate inosine, and phosphate (Sulphate) at 2.1 A resolution. J Mol Biol 280 (1), 153-166.

Poole, L.B. (2005) Bacterial defenses against oxidants: mechanistic features of cysteine-based peroxidases and their flavoprotein reductases. Arch Biochem Biophys 433 (1), 240-254.

Wood, Z.A. et al (2002) Dimers to doughnuts: redox-sensitive oligomerization of 2-cysteine peroxiredoxins. Biochemistry 41 (17), 5493-5504.

Akagi, R. et al. (1999) A novel mutation of delta-aminolaevulinate dehydratase in a healthy child with 12% erythrocyte enzyme activity. Br J Haematol 106 (4), 931-937.

Maruno, M. et al. (2001) Highly heterogeneous nature of delta-aminolevulinate dehydratase (ALAD) deficiencies in ALAD porphyria. Blood 97 (10), 2972-2978.

Jaffe, E.K. (2004) The porphobilinogen synthase catalyzed reaction mechanism. Bioorg Chem 32 (5), 316-325.

Frankenberg, N. et al. (1999) High resolution crystal structure of a Mg2+ -dependent porphobilinogen synthase. J Mol Biol 289 (3), 591-602.

Kervinen, J. et al. (2001) Mechanistic basis for suicide inactivation of porphobilinogen synthase by 4,7-dioxosebacic acid, an inhibitor that shows dramatic species selectivity. Biochemistry 40 (28), 8227-8236.

Jaffe, E.K. et al. (1995) Characterization of the role of the stimulatory magnesium of *Escherichia coli* porphobilinogen synthase. Biochemistry 34 (1), 244-251.

Frankenberg, N. et al. (1999) *Pseudomonas aeruginosa* contains a novel type V porphobilinogen synthase with no required catalytic metal ions. Biochemistry 38 (42), 13976-13982.

Papenbrock, J. et al. (2000) Role of magnesium chelatase activity in the early steps of the tetrapyrrole biosynthetic pathway. Plant Physiol 122 (4), 1161-1169.

Papenbrock, J. and Grimm, B. (2001) Regulatory network of tetrapyrrole biosynthesis—studies of intracellular signalling involved in metabolic and developmental control of plastids. Planta 213 (5), 667-681.

Walker, D.A. (1976) Regulatory mechanisms in photosynthetic carbon metabolism. Curr Top Cell Regul 11, 203-241.

Stolz, M. and Dornemann, D. (1996) Purification, metal cofactor, N-terminal sequence and subunit composition of a 5-aminolevulinic acid dehydratase from the unicellular green alga *Scenedesmus obliquus*, mutant C-2A'. Eur J Biochem 236 (2), 600-608.

Tamai, H. et al. (1979) Plant Cell Physiol. 20, 435-444.

Breinig, S. et al. (2003) Control of tetrapyrrole biosynthesis by alternate quaternary forms of porphobilinogen synthase. Nat. Struct. Biol. 10, 757-763.

Frere, F. et al. (2002) Structure of porphobilinogen synthase from *Pseudomonas aeruginosa* in complex with 5-fluorolevulinic acid suggests a double Schiff base mechanism. J Mol Biol 320 (2), 237-247.

Friesner, R.A. et al. (2004) Glide: a new approach for rapid, accurate docking and scoring. 1. Method and assessment of docking accuracy. J Med Chem 47 (7), 1739-1749.

Halgren, T.A. et al. (2004) Glide: a new approach for rapid, accurate docking and scoring. 2. Enrichment factors in database screening. J Med Chem 47 (7), 1750-1759.

Cooperman, B.S. and Kashlan, O.B. (2003) A comprehensive model for the allosteric regulation of Class Ia ribonucleotide reductases. Adv Enzyme Regul 43, 167-182.

Dhanasekaran, S. et al. (2004) Delta-aminolevulinic acid dehydratase from Plasmodium falciparum: indigenous versus imported. J Biol Chem 279 (8), 6934-6942.

Irwin, J.J. and Shoichet, B.K. (2005) ZINC—a free database of commercially available compounds for virtual screening. J Chem Int Model 45 (1), 177-182.

Shimizu-Sato, S. et al. (2002) A light-switchable gene promoter system. Nat Biotechnol 20 (10), 1041-1044.

Daniell, H. et al. (1998) Containment of herbicide resistance through genetic engineering of the chloroplast genome. Nat. Biotechnol. 16 (4), 345-348.

Potrykus, I. et al. (1985) Molecular and general genetics of a hybrid foreign gene introduced into tobacco by direct gene transfer. Mol. Gen. Genet. 199 (2), 169-177.

Stalker, D.M. et al. (1988) Purification and properties of a nitrilase specific for the herbicide bromoxynil and corresponding nucleotide sequence analysis of the bxn gene. J. Biol. Chem. 263 (13), 6310-6314.

Thillet, J. et al. (1988) Site-directed mutagenesis of mouse dihydrofolate reductase. Mutants with increased resistance to methotrexate and trimethoprim. J. Biol. Chem. 263 (25), 12500-12508.

Fraley, R.T. et al. (1983) Expression of bacterial genes in plant cells. Proc. Natl. Acad. Sci. U S A 80 (15), 4803-4807.

Schmidhauser, T.J. and Helinski, D.R. (1985) Regions of broad-host-range plasmid RK2 involved in replication and stable maintenance in nine species of Gram-negative bacteria. J. Bacteriol. 164, 446-455.

Jaffe et al., "Morpheeins—a new structural paradigm for allosteric regulation", Trends in Biochemical Sciences, Elsevier, Haywards, GB, vol. 30, No. 9, Sep. 1, 2005, pp. 490-497.

Kimmel et al., "Inactivation of GDP-mannose dehydrogenase from *Pseudomonas aeruginosa* by penicllic acid identifies a critical active site loop", Archives of Biochemistry and Biophysics, NY, US, vol. 441, No. 2, Sep. 15, 2005, pp. 132-140.

Supplementary European Search Report for EP 06 77 3249.

U.S. Appl. No. 11/327,762, filed Jan. 6, 2006.

U.S. Appl. No. 12/142,435, filed Jun. 19, 2008.

Kervinen, J. et al. (2001) Mechanistic basis for suicide inactivation of porphobilinogen synthase by 4,7-dioxosebacic acid, an inhibitor that shows dramatic species selectivity. Biochemistry 40 (28), 8227-8236.

Selwood, T., Tang, L., Lawrence, S.H., Anokhina, Y., and Jaffe, E.K. (2008). Kinetics and thermodynamics of the interchange of the morpheein forms of human porphobilinogen synthase. Biochemistry 47, 3245-3257.

Tang, L., Breinig, S., Stith, L., Mischel, A., Tannir, J., Kokona, B., Fairman, R., and Jaffe, E.K. (2006). Single amino acid mutations alter the distribution of human porphobilinogen synthase quaternary structure isoforms (morpheeins). J Biol Chem 281, 6682-6690.

Tang, L. Stith, L., and Jaffe, E.K. (2005). Substrate-induced interconversion of protein quaternary structure isoforms. J Biol Chem 280, 15786-15793.

Kokona, B., Rigotti, D.J., Wasson, A.S., Lawrence, S.H., Jaffe, E.K., and Fairman, R. (2008). Probing the oligomeric assemblies of pea porphobilinogen synthase by analytical ultracentrifugation. Biochemistry 47, 10649-10656.

Lawrence, S.H., Ramirez, U.D., Tang, L., Fazliyez, F., Kundrat, L., Markham, G.D., and Jaffe, E.K. (2008). Shape shifting leads to small-molecule allosteric drug discovery. Chem Biol 15, 586-596.

Supplementary European Search Report for EP 06 77 3249, (2008).

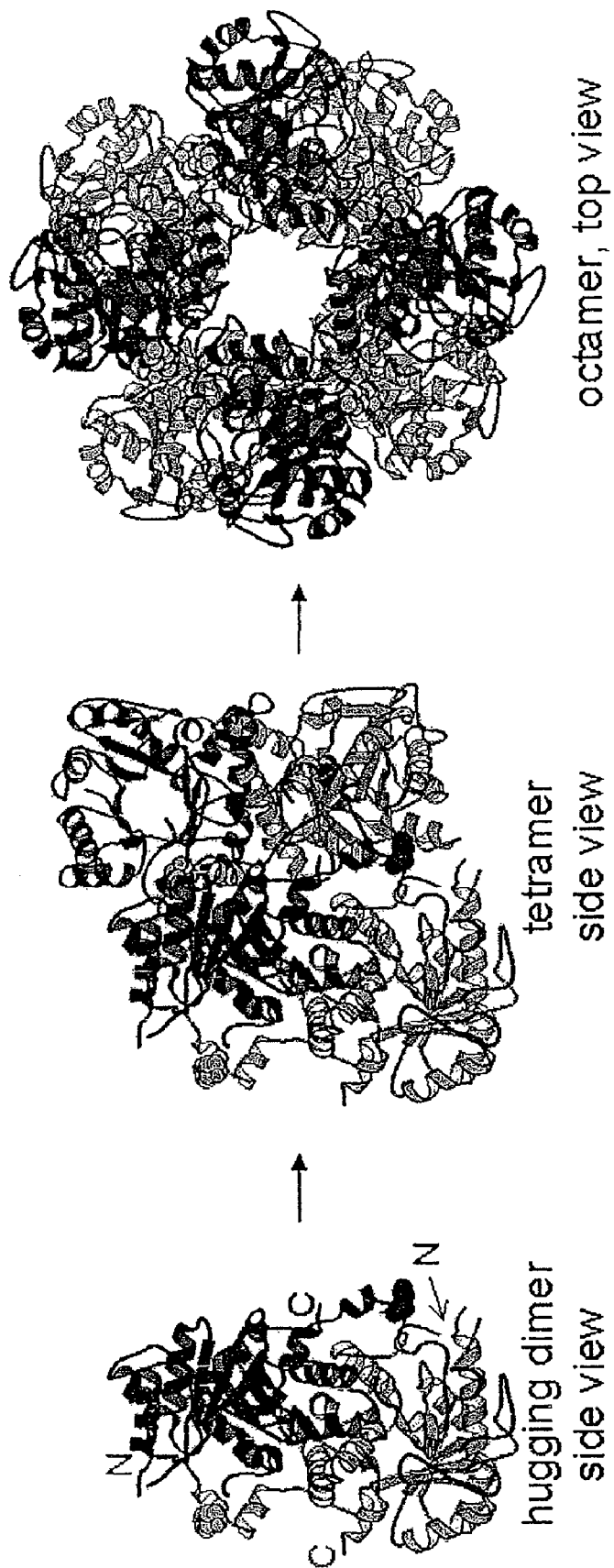

(PRIOR ART)

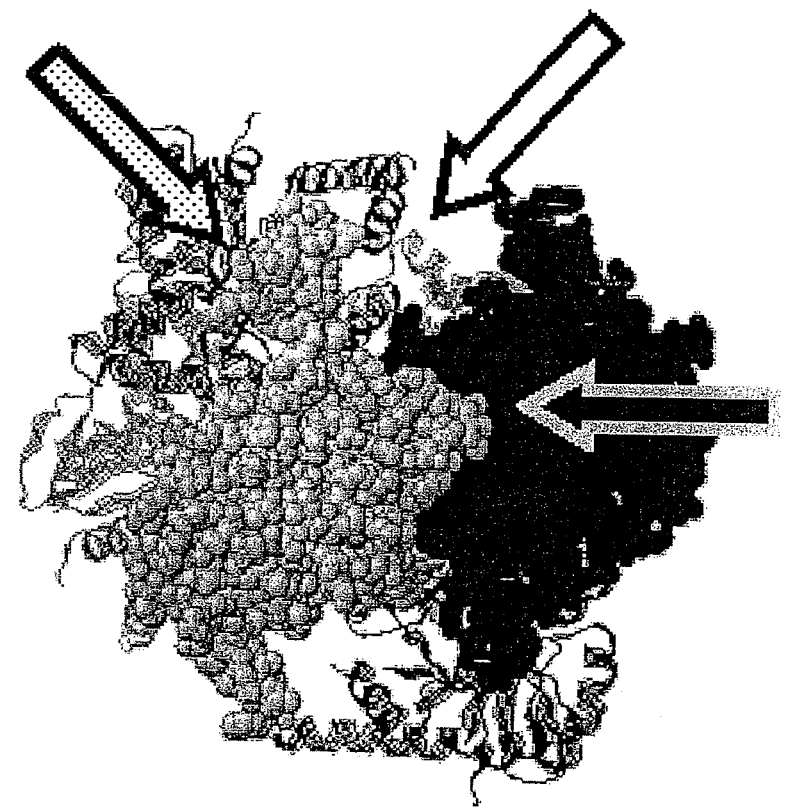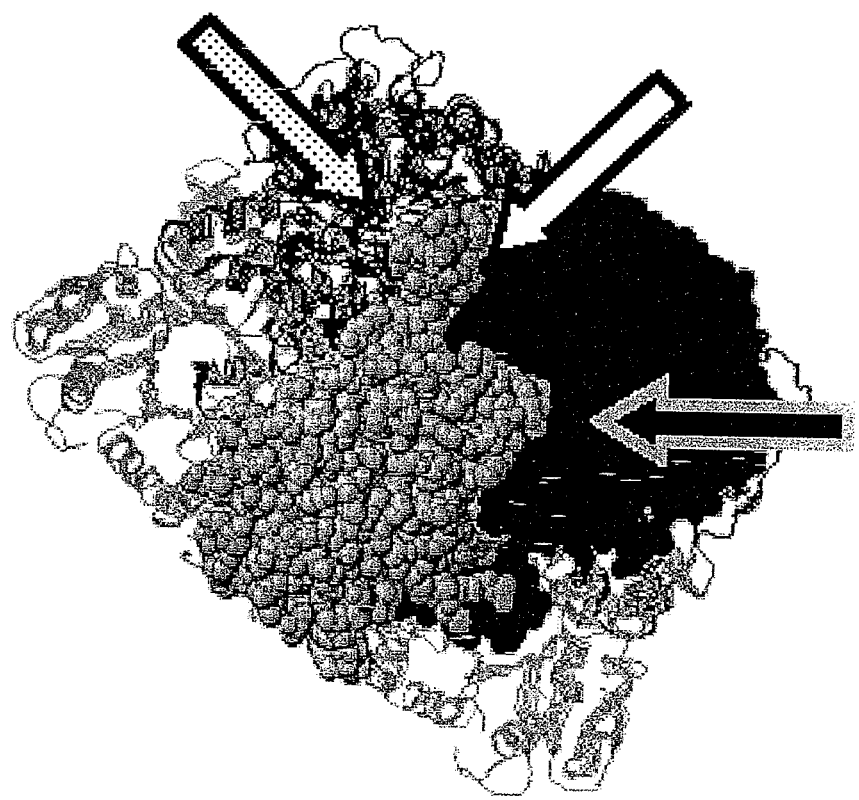
Figure 18B

Human hexamer structure favored by Leu-12 containing chains

Human octamer structure favored by Phe-12 containing chains

Spheres show water molecules that are within 4.0 Å of both subunits A and B.

Figure 30
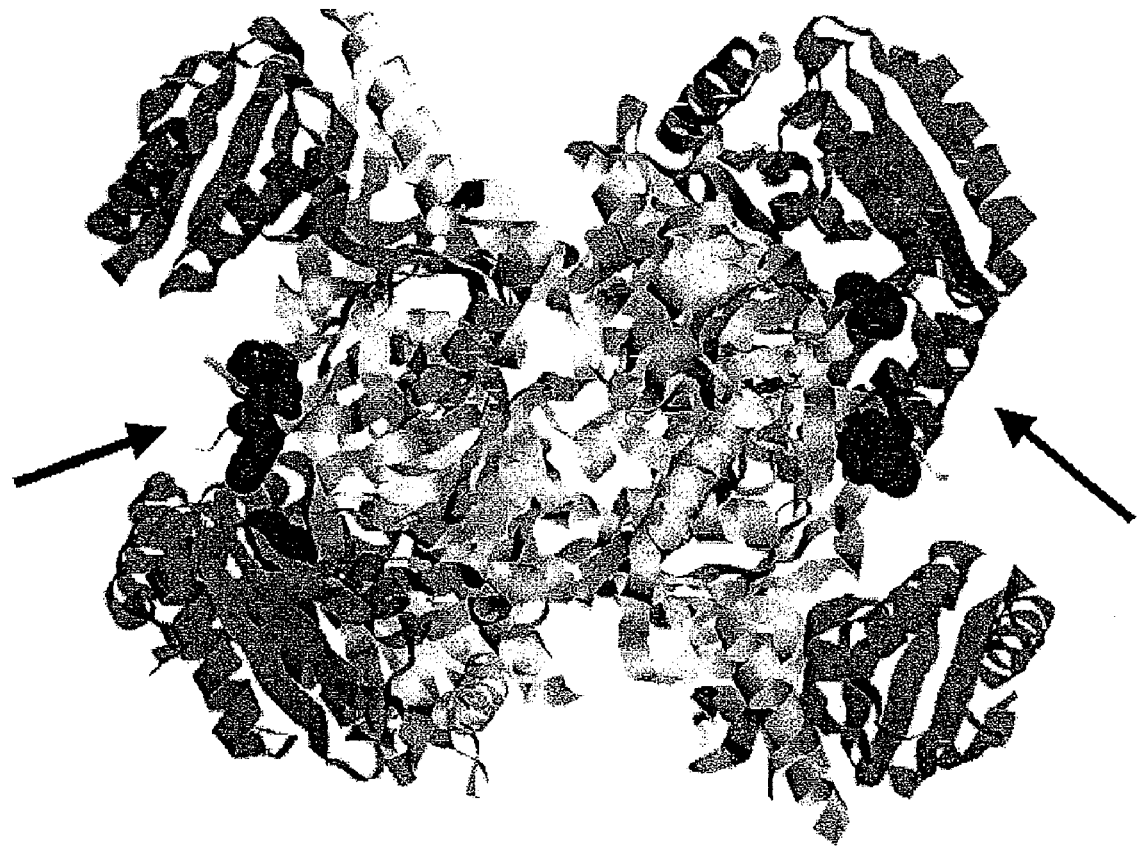

US 7,863,029 B2

ALTERNATE MORPHEEINS OF ALLOSTERIC PROTEINS AS A TARGET FOR THE DEVELOPMENT OF BIOACTIVE MOLECULES

This application is a divisional of U.S. patent application Ser. No. 11/327,762, filed Jan. 6, 2006, now abandoned, which is a continuation-in-part of PCT/US04/21722, filed Jul. 7, 2004, which claims benefit of U.S. Provisional Patent Application Ser. No. 60/577,312, filed Jun. 4, 2004; and said 11/327,762, filed Jan. 6, 2006, which claims benefit of 60/690,649, filed Jun. 15, 2005.

REFERENCE TO MATERIAL ON COMPACT DISC

The Sequence Listing submitted on compact disc is incorporated herein by reference in its entirety.

BACKGROUND OF THE INVENTION

1. Field of Invention

This invention relates to the allosteric regulation of protein function through stabilization of one or more different quaternary assemblies, herein defined as morpheeins. The different morpheeins of a given protein have different surface characteristics that can be targeted for the development of a broad spectrum of bioactive agents. As an example, this invention relates to the biosynthesis of tetrapyrroles, and more particularly to a mechanism for inhibiting activation of porphobilinogen synthase.

2. Description of Related Art

It is generally accepted that the three dimensional structure of a protein is determined by the sequence of that protein and that there is one structure for each protein [1]. Exceptions to this rule include prions, a term that remains controversial, but is taken to refer to proteins that can change from their biologically active globular shape to a fibrillar shape which can form an aggregate that can grow indefinitely into disease causing amyloid plaques (e.g. scrapie). The formation of the amyloid protein structure from the globular prion protein structure is believed to be irreversible. This invention does not deal with prion proteins, nor with any other irreversible transformation in protein shape, such as denaturation. A second example of a situation where one protein is known to exist in two forms, more particularly in two quaternary assemblies, occurs as the quasiequivalence of some virus capsid proteins [2,3]. The quasiequivalent virus capsid proteins are the stable components of the geodesic dome that encapsulates the virus; these stable structures exist as parts of a larger assembly and are fundamentally different from the morpheein structures introduced herein.

Allosteric effects on ligand binding and/or catalytic activity are changes in said binding or activity which are caused by binding of another molecule (the allosteric effector molecule) to a site on the protein that is different from the ligand binding site or active site. The behavior of many proteins is known to be subject to allosteric regulation. Many allosteric proteins are known to exist as homomeric multimers (oligomers made up of subunits where the sequence of each of the subunits is identical to the others). There are two well-accepted models for allosteric regulation, the Monod Wyman Changeux model and the Koshland model [4,5]. Both of these models explicitly presume that the allosteric "ON" state and the allosteric "OFF" state have a constant oligomeric multiplicity as illustrated schematically in FIG. 1. The current invention is about a third model for allosteric regulation of protein function, the morpheein model, where the oligomeric multiplicity of the "ON" state and the "OFF" state of a homo-oligomeric protein are different.

Tetrapyrrole biosynthesis is an essential pathway in animals, plants, and microbes, including bacteria, archae, fungi, and protists. The first common intermediate is 5-aminolevulinic acid (ALA). The enzymatic reactions from ALA to uroporphyrinogen are common to tetrapyrrole biosynthesis in all organisms [6,7].

The enzyme porphobilinogen synthase (PBGS, EC 4.2.1.24), also known as 5-aminolevulinic acid dehydratase (ALAD), is an ancient and highly conserved protein that catalyzes the first common step in the biosynthesis of tetrapyrroles including heme, chlorophyll, vitamin $B_{12}$, and cofactor $F_{430}$ [8,9]. PBGS catalyzes the condensation of two 5-aminolevulinic acid molecules to form the tetrapyrrole precursor porphobilinogen.

PBGS was previously understood to be a homooctameric metalloenzyme, which utilizes a variety of divalent and monovalent cations at catalytic and allosteric sites. The first 18 deposited X-ray crystal structures showed an octameric assembly [10], as illustrated for human PBGS in FIG. 2. Mammalian and yeast enzymes typically require Zn(II), some prokaryotic enzymes require either Mg(II) or Zn(II) or both for maximal activity, and plant enzymes seem to require only Mg(II) for enzymatic activity. A small number of organisms have PBGS enzymes that require neither Zn(II) nor Mg(II). The difference in the use of metal ions is caused by a variation of residues in the primary structures in at least two metal-binding regions [11]. The structure of E. coli PBGS is illustrated in FIGS. 3A-C and serves to illustrate the common metal binding variations in PBGS structures. Each E. coli PBGS monomer contains two metal ions, neither of which is phylogenetically conserved. The active site contains a zinc ion that is essential to E. coli PBGS activity but whose three cysteine ligands are not present in many PBGS. This zinc functions in the binding and reactivity of the second substrate molecule [12]. Details of the zinc site are illustrated in FIG. 3B. In addition, there is an allosteric magnesium that is seen bound at the interface of each alpha, beta-barrel with the N-terminal arm of a neighboring subunit; structural details are in FIG. 3C. The sequence determinants for binding the allosteric magnesium are not present in all PBGS. The PBGS have been categorized into four groups based on whether or not they have the catalytic zinc binding site and whether or not they have the allosteric magnesium binding site, as illustrated in FIG. 4.

FIG. 4 is a schematic for classifying the PBGS into four groups on the basis of whether or not they use an active site zinc and whether or not they use an allosteric magnesium [11]. The first matrix (far left) is divided into two classes: (a) active site zinc on the left (shaded), and (b) no active site zinc on the right (unshaded). The second matrix is divided into two classes: (a) no allosteric magnesium on top (white), and (b) allosteric magnesium on the bottom (squares). Combining the two matrixes provides a matrix (far right) consisting of four quadrants, wherein the northwest quadrant (QNW) represents +Zn/−Mg, the northeast quadrant (QNE) represents −Zn/−Mg, the southwest quadrant (QSW) represents +Zn/+Mg, and the southeast quadrant (QSE) represents −Zn/+Mg. The terms QNR, QNR, QSW, and QSE are used throughout this document to refer to the quadrants of FIG. 4.

The inventor has previously quantified [11] the following distribution of known sequences into the four quadrants: QNW=9; QNE=2; QSW=55 and QSE=63. Thus, approximately one-half of the currently available sequences encode an active site zinc requirement and one-half do not (i.e., QNW+QSW~QNE+QSE). In contrast to the active site metal pattern distribution, more than 90% of the PBGS sequences contain the determinants for allosteric magnesium binding (i.e., QSW+QSE>>QNW+QNE).

It has been found that the specific activity of PBGS from some sources is dependent on protein concentration, as illustrated in FIG. 5. For example, a protein concentration dependence for the specific activity has been seen for *B. japonicum*, *P. aeruginosa*, *R. capsulatus* and pea PBGS, but has not been documented for PBGS from *E. coli*, yeast, or from mammalian sources [13-15]. Prior interpretation of this phenomenon was a simple dissociation reaction of a maximally active octamer to lesser active or inactive tetramers and/or dimers (FIG. 5). Prior interpretation did not include alternative morpheeins of PBGS.

It is known to inhibit PBGS by removing metals from an active site or from an allosteric site, e.g., by treating it with ethylenediaminetetraacetic acid (EDTA), or 1,10-phenanthroline [16,17].

Today, many consumers are demanding that personal health care products such as wet wipes, diapers, etc. have the ability to not only provide their intended function, but to cure or prevent a disease or a damage caused by contacting bacteria, archaea, and/or eucarya, for example, while not harming the consumer's health. To meet this demand, antimicrobial agents have been incorporated into a wide range of consumer products, such as wet wipes, to combat both transient and resident bacteria on skin. Antimicrobial-containing products are currently marketed in many forms such as lotions, deodorant soaps, hard surface cleaners, wet wipes, and surgical disinfectants.

Biofilms can be a problem for certain surfaces. Biofilms may be found on essentially any environmental surface in which sufficient moisture is present. Their development is most rapid in flowing systems where adequate nutrients are available. Biofilms are composed of populations or communities of microorganisms adhering to environmental surfaces and are complex aggregate of cells and polysaccharide. These microorganisms are usually encased in an extracellular polysaccharide that they synthesize. The biofilm, for example can be formed from mixed culture of *Pseudomonas aeruginosa*, *P. fluorescens* and *Klebsiella pneumoniae*. Biofilms may form on solid substrates in contact with moisture, on soft tissue surfaces in living organisms and at liquid air interfaces. Typical locations for biofiln production include rock and other substrate surfaces in marine or freshwater environments. Biofilms are also commonly associated with living organisms, both plant and animal. Tissue surfaces such as teeth and intestinal mucosa which are constantly bathed in a rich aqueous medium rapidly develop a complex aggregation of microorganisms enveloped in an extracellular polysaccharide they themselves produce. The ability of oral bacteria to store iodophilic polysaccharides or glycogen-like molecules inside their cells is associated with dental caries since these storage compounds may extend the time during which lactic acid formation may occur. It is this prolonged exposure to lactic acid which results in decalcification of tooth enamel.

People have made use of microbial biofilms, primarily in the area of habitat remediation. Water treatment plants, waste water treatment plants and septic systems associated with private homes remove pathogens and reduce the amount of organic matter in the water or waste water through interaction with biofilms. On the other hand biofilms can be a serious threat to health especially in patients in whom artificial substrates have been introduced. Also, biofilms are a threat to bottoms of ship wherein barnacles can grow and corrode the surface or on the external or the internal surfaces of pipes such as oil pumps or dehumidifiers.

Despite the foregoing developments, it is desired to provide bioactive compositions having universal applications. It is further desired to provide an agent capable of disturbing an equilibrium of units of multimeric proteins, e.g., an inhibitor capable of inhibiting tetrapyrrole biosynthesis in plants and/or bacteria through the stabilization of a lesser active quaternary assembly of porphobilinogen synthase. It is further desired to accomplish such inhibition via a mechanism that is not applicable to humans and animals, thereby creating a novel, highly specific, approach to bacteriostatic, antibiotic, or herbicide activity. As many essential proteins are homo-oligomeric and allosteric in nature, it is desired to provide bioactive compounds that will inhibit or activate these homo-oligomeric proteins through perturbation of an equilibrium of quaternary assemblies.

All references cited herein are incorporated herein by reference in their entireties.

BRIEF SUMMARY OF THE INVENTION

Accordingly, the invention provides a composition comprising an agent adapted to affect a multimeric protein by binding to a binding site of said multimeric protein and thereby affecting an equilibrium of units, wherein said multimeric protein comprises an assembly having a plurality of said units, wherein each of said units comprises a first complementary surface and a second complementary surface and wherein the first complementary surface of one unit is associated with the second complementary surface of another unit, provided that the assembly is at least one of different quaternary isoforms on a condition that in said multimeric protein (1) a structure of each of said units determines a structure of said different quaternary isoforms, (2) said units are in the equilibrium and (3) the structure of said different quaternary isoforms influences a function of the multimeric protein. In certain embodiments, affecting said multimeric protein comprises affecting a formation of a quaternary isoform.

In certain embodiments, affecting said multimeric protein comprises affecting the function of said multimeric protein. A non-limiting example of a function of said multimeric protein is an activity and wherein affecting is at least one of inhibiting or activating.

In certain embodiments, the agent is bound to at least one of a quaternary isoform having a lesser activity or a quaternary isoform having a greater activity.

Non-limiting examples of the units include a monomer, a dimer, a trimer, a tetramer, a hexamer, and an octamer. For proteins other than PBGS, the units could be also pentamers, heptamers, nonomers, decamers, etc.

In certain embodiments, said multimeric protein is a member selected from the group consisting of porphobilinogen synthase, Class Ia ribonucleotide reductase, GDP-mannose dehydrogenase, histidine containing phosphocarrier protein kinase/phophatase, mammalian CoA transferase, purine nucleoside phosphorylase, and peroxiredoxins.

In certain embodiments, said multimeric protein is porphobilinogen synthase comprising eight porphobilinogen synthase monomers. In other embodiments, the active form of the multimeric porphobilinogen synthase has less than eight monomers.

In certain embodiments, the agent is an inhibitor bound to the quaternary isoform having the lesser activity and wherein the quaternary isoform contains less than eight porphobilinogen synthase monomers. In certain embodiments, the inhibitor is rosmarinic acid or a derivative thereof.

In certain embodiments, said multimeric protein is the Class Ia ribonucleotide reductase and the agent inhibits the Class Ia ribonucleotide reductase through selective binding to the binding site that is unique to the quaternary isoform having the lesser activity. In the case of the Class Ia ribonucleotide reductase, on the basis of the published literature, the morpheein having lesser activity is predicted to be a tetramer, for which a structure is not yet available.

In certain embodiments, said multimeric protein is GDP-mannose dehydrogenase and the agent inhibits GDP-mannose dehydrogenase through selective binding to the binding site that is unique to the quaternary isoform having the lesser activity. The existing tetrameric crystal structure of GDP-mannose dehydrogenase [18] is predicted to be the inactive form because biochemical data predicts that the active form is a hexamer [19].

In certain embodiments, said multimeric protein is histidine containing phosphocarrier protein kinase/phophatase and the agent inhibits through selective binding to the binding site that is unique to the quaternary isoform having the lesser activity. In this case the hexameric form, for which there is a crystal structure, is predicted to have phosphatase activity and be inactive for the kinase activity [20]. Thus trapping the hexamer would trap the form less active for the kinase activity.

In certain embodiments, said multimeric protein is mammalian CoA transferase and the agent inhibits mammalian CoA transferase through selective binding to the binding site that is unique to the quaternary isoform having the lesser activity. Mammalian CoA transferase is reported to exist in both dimeric and tetrameric forms, which are separated by a large kinetic barrier [21]. It remains unclear if the tetrameric form is of equal activity or if there is a rapid reequilibration to the active dimeric form in the presence of substrate.

In certain embodiments, said multimeric protein is purine nucleoside phosphorylase and the agent inhibits purine nucleoside phosphorylase through selective binding to the binding site that is unique to the quaternary isoform having the lesser activity. Current data suggests that the morpheeins of purine nucleoside phosphorylase are dimers, trimers, and two different hexamers [22,23], but data is insufficient to propose which are inactive forms. In certain embodiments, said multimeric protein is a peroxiredoxin and the agent inhibits the peroxiredoxin through selective binding to the binding site that is unique to the quaternary isoform having the lesser activity. The quaternary isoforms of the peroxiredoxins appear to consist of a dimer that cannot form multimers, a dimer that can form multimers, and the decamer of the latter dimer [24,25]. The inactive morpheein is proposed to be the dimer that can form decamers.

Also provided is a composition comprising an inhibitor adapted to inhibit formation of an active form of a multimeric porphobilinogen synthase having a first number of monomers by binding to a less active form of the multimeric porphobilinogen synthase having a second number of monomers, wherein the first number of monomers is higher than the second number of monomers.

In certain embodiments, the multimeric porphobilinogen synthase is derived from bacteria, archaea, or eucarya, provided that the octameric porphobilinogen synthase contains an allosteric magnesium binding site. In one variant of this embodiment, the multimeric porphobilinogen synthase contains a catalytic zinc binding site.

In certain embodiments, the multimeric porphobilinogen synthase does not contain the allosteric magnesium binding site and does not contain the catalytic zinc binding site.

In certain embodiments, said less active form is a hexamer. In certain embodiments, said less active form is a dimer. In certain embodiments, the active form of a multimeric porphobilinogen synthase is an octamer.

In certain embodiments, the inhibitor replaces a metal ion and thereby binds at a metal ion binding site. In certain embodiments, the metal ion is zinc and/or magnesium.

In certain embodiments, the inhibitor binds at an active site.

In certain embodiments, the inhibitor is not a metal cation.

In certain embodiments, the inhibitor is adapted to inhibit formation of the active form of the multimeric porphobilinogen synthase, said active form is an octameric porphobilinogen synthase by binding to a hug-disabling domain of the less active form of the multimeric porphobilinogen synthase containing less than eight monomers.

In certain embodiments, the inhibitor is adapted to inhibit formation of the active form of the multimeric porphobilinogen synthase by binding at a site other than an active site and/or metal ion binding site.

In certain embodiments, the inhibitor is adapted to inhibit formation of the active form of the multimeric porphobilinogen synthase by a mechanism other than removing a metal ion.

In certain embodiments, the composition further comprises a delivery medium, said delivery medium is a member selected from the group consisting of a pharmaceutically-acceptable medium, an orally-acceptable carrier, an antibacterial medium, and a herbicidally-effective medium.

Advantageously, the composition is effective to inhibit or prevent formation of the active form of the multimeric porphobilinogen synthase and thereby inhibiting or preventing development or growth of bacteria, archaea, and/or eucarya. In one variant of this embodiment, the composition is effective to cure or prevent a disease caused by contacting bacteria, archaea, and/or eucarya. In one variant of this embodiment, the composition is at least one of a drug, a toothpaste, a soap, a disinfectant, an anti-biofilm composition, and a herbicide.

In certain embodiments, the composition is effective to inhibit or prevent formation of the active form of the multimeric porphobilinogen synthase and thereby inhibiting or preventing development or growth of bacteria, archaea, and/or eucarya. In one variant of this embodiment, the composition is effective to cure or prevent a disease caused by contacting bacteria, archaea, and/or eucarya. In one variant of this embodiment, the composition is at least one of a drug, a toothpaste, a soap, and a disinfectant.

Further provided is a herbicide resistant plant adapted to be transgenic for a multimeric porphobilinogen synthase that substantially exist in a multimeric form of a hugging dimer. In certain embodiments, the multimeric porphobilinogen synthase is derived from a human. In certain embodiments, the multimeric porphobilinogen synthase contains no allosteric magnesium binding site.

Further provided is a composition comprising an inhibitor adapted to bind to a multimeric porphobilinogen synthase that does not require zinc for catalytic function.

Also provided is a method of affecting a multimeric protein, the method comprising: providing said multimeric protein comprising an assembly having a plurality of units, wherein each of said units comprises a first complementary surface and a second complementary surface and wherein the first complementary surface of one unit is associated with the second complementary surface of another unit, provided that the assembly is at least one of different quaternary isoforms on a condition that (1) a structure of said units determines a structure of said different quaternary isoforms, (2) said units are in an equilibrium and (3) the structure of said different quaternary isoforms influences a function of said multimeric protein; providing the composition of the invention comprising the agent, wherein the agent is adapted to affect the equilibrium by binding to a binding site on the assembly; and contacting the assembly with the agent, wherein the agent affects the equilibrium by binding to the binding site and thereby affecting said multimeric protein. In certain embodiments of the method, affecting said multimeric protein comprises affecting a formation of a quaternary isoform. In certain embodiments of the method, affecting said multimeric protein comprises affecting a function of said multimeric protein.

In certain embodiments of the method, the units include a monomer, a dimer, a trimer, a tetramer, a hexamer, and an octamer. For proteins other than PBGS, the units could be also pentamers, heptamers, nonomers, decamers, etc.

In certain embodiments of the method, the agent is adapted to affect a function of said multimeric protein.

In certain embodiments of the method, the function of said multimeric protein is an activity and wherein affecting is at least one of inhibiting or activating.

In certain embodiments of the method, the agent is bound to at least one of a quaternary isoform having a lesser activity or a quaternary isoform having a greater activity.

In certain embodiments of the method, the agent is bound to the quaternary isoform having a greater activity.

In certain embodiments of the method, said multimeric protein is a member selected from the group consisting of porphobilinogen synthase, Class Ia ribonucleotide reductase, GDP-mannose dehydrogenase, histidine containing phosphocarrier protein kinase/phophatase, mammalian CoA transferase, purine nucleoside phosphorylase, and peroxiredoxins.

In certain embodiments of the method, said multimeric protein is porphobilinogen synthase comprising eight porphobilinogen synthase monomers.

In certain embodiments of the method, said multimeric protein is the Class Ia ribonucleotide reductase and the agent inhibits the Class Ia ribonucleotide reductase through selective binding to the binding site that is unique to the quaternary isoform having the lesser activity.

In certain embodiments of the method, said multimeric protein is the GDP-mannose dehydrogenase and the agent inhibits the GDP-mannose dehydrogenase through selective binding to the binding site that is unique to the quaternary isoform having the lesser activity.

In certain embodiments of the method, said multimeric protein is the histidine containing phosphocarrier protein kinase/phophatase and the agent inhibits the histidine containing phosphocarrier protein kinase/phophatase through selective binding to the binding site that is unique to the quaternary isoform having the lesser activity.

In certain embodiments of the method, said multimeric protein is mammalian CoA transferase and the agent inhibits the mammalian CoA transferase through selective binding to the binding site that is unique to the quaternary isoform having the lesser activity.

In certain embodiments of the method, said multimeric protein is urine nucleoside phosphorylase and the agent inhibits the urine nucleoside phosphorylase through selective binding to the binding site that is unique to the quaternary isoform having the lesser activity.

In certain embodiments of the method, said multimeric protein is peroxiredoxins and the agent inhibits peroxiredoxins through selective binding to the binding site that is unique to the quaternary isoform having the lesser activity.

Further provided is a method of modulating a physiological activity in a cell, a tissue or an organism, the method comprising: providing the cell, the tissue or the organism, wherein the cell, the tissue or the organism comprise a multimeric protein comprising an assembly having a plurality of units, wherein each of the units comprises a first complementary surface and a second complementary surface and wherein the first complementary surface of one unit is associated with the second complementary surface of another unit, provided that the assembly is at least one of different quaternary isoforms on a condition that (1) a structure of said units determines a structure of said different quaternary isoforms, (2) said units are in an equilibrium and (3) the structure of said different quaternary isoforms influences a function of the multimeric protein; and providing to the cell, the tissue or the organism the composition of the invention comprising the agent, wherein the agent is adapted to affect the equilibrium by binding to the binding site on the unit and thereby affecting the formation of a quaternary isoform and thereby modulating the physiological activity.

Further provided is a method of inhibiting a multimeric porphobilinogen synthase from forming an active form, the method comprising: applying the composition of the invention to the multimeric porphobilinogen synthase; associating the composition with the less active form; inhibiting the less active form from assembling into the active form and thereby inhibiting the multimeric porphobilinogen synthase from forming the active form.

Further provided is a method for manipulating growth or development of a plant comprising applying the composition of the invention which is a herbicide to the plant, wherein the plant is herbicide resistant and is adapted to be transgenic for a multimeric porphobilinogen synthase that substantially exist in a multimeric form of a hugging dimer. In one variant of the method, the multimeric porphobilinogen synthase contains no allosteric magnesium binding site.

Further provided is a method of making an antibacterial surface, the method comprising: (1) providing the composition of the invention wherein the composition is effective to inhibit or prevent formation of the active form of the multimeric porphobilinogen synthase and thereby inhibiting or preventing development or growth of bacteria, archaea, and/or eucarya, provided that the active form of the multimeric porphobilinogen synthase contains an allosteric magnesium binding site and the composition is at least one of a drug, a toothpaste, a soap, a disinfectant, an anti-biofilm composition, and a herbicide; (2) providing a surface-forming matrix; and (3) combining the composition with the surface-forming matrix and thereby making the antibacterial surface. In one variant of the method, the antibacterial surface is adapted to prevent or inhibit a formation of a biofilm.

BRIEF DESCRIPTION OF SEVERAL VIEWS OF THE DRAWINGS

The invention will be described in conjunction with the following drawings in which like reference numerals designate like elements and wherein:

FIG. 2 (prior art) shows the assembly of octameric human PBGS (PDB code 1e51) using ribbon representation. To the left is the hugging dimer; in the middle is the tetramer (same orientation as the hugging dimer), and on the right is a top down view of the octamer. For each dimer, one monomer is light gray and the other is dark gray.

FIG. 2 illustrates the differential assembly of octameric and hexameric human PBGS.

FIG. 15A represents an alignment of active site metal binding residues for the PBGS sequences of Eukaryota and Archaea, which were obtained from GenBank and other web-searchable genomes available as of April 2002.

FIGS. 15B and 15C represents an alignment of active site metal binding residues for the PBGS sequences of Eubacteria, which were obtained from GenBank and other web-searchable genomes available as of April 2002.

FIG. 18B shows the subunit interfaces of human PBGS octamer (left) relative to the hexamer (right). The first dimer is illustrated using space fill (gray and black) and the remaining subunits are shown in a strand representation. The black bordered white arrow shows the locations comparable to the allosteric magnesium in FIG. 18A. This binding site is present in the octamer and absent in the hexamer.

FIG. 25A is a graph demonstrating porphobilinogen formation during the equilibrium dialysis of Pools I and II (as per FIG. 17A) against buffer containing ALA. (◇) Pool II, pH 7.0; (Δ) Pool I, pH 7.0; (□) Pool II, pH 9.0. (○) Pool I, pH 9.0.

FIG. 25B is a picture of native electrophoresis gels of WT+F12L Pool I and Pool II during dialysis at 37 C in the presence and absence of ALA at various times. In the absence of ALA the percentage of octamer and hexamer remain unchanged. In the presence of ALA, the equilibrium of all Pools shifts toward the octamer.

FIG. 25C is a graph demonstrating densitometric analysis of the native gel data shown in FIG. 25B. (■) Pool II, pH 9.0; (▲) Pool I, pH 7.0; (●) Pool I, pH 9.0. The lines are the best fit to a single rate exponential equation.

FIG. 26A is a picture of gels obtained in native gel electrophoresis of the Pools before dialysis, after 24 hours of dialysis against ALA at pH 7, and after chromatographic separation on the Mono-Q column.

FIG. 30 illustrates two orientations of the crystal structure of *Lactobacillus casei* HPrK/P, in the hexameric assembly (ribbons in white), complexed with the HPr protein of *Bacillus subtilis* (ribbons in gray). The tryptophan illustrated using the space filling representation (dark gray) is the only tryptophan in HPrK/P of both *L. casei* and *B. subtilus*. The putative drug-binding site is illustrated with an arrow.

DETAILED DESCRIPTION OF THE INVENTION

The present invention was prompted by the inventor's studies relating to the basic science of tetrapyrrole biosynthesis.

Figure 1:
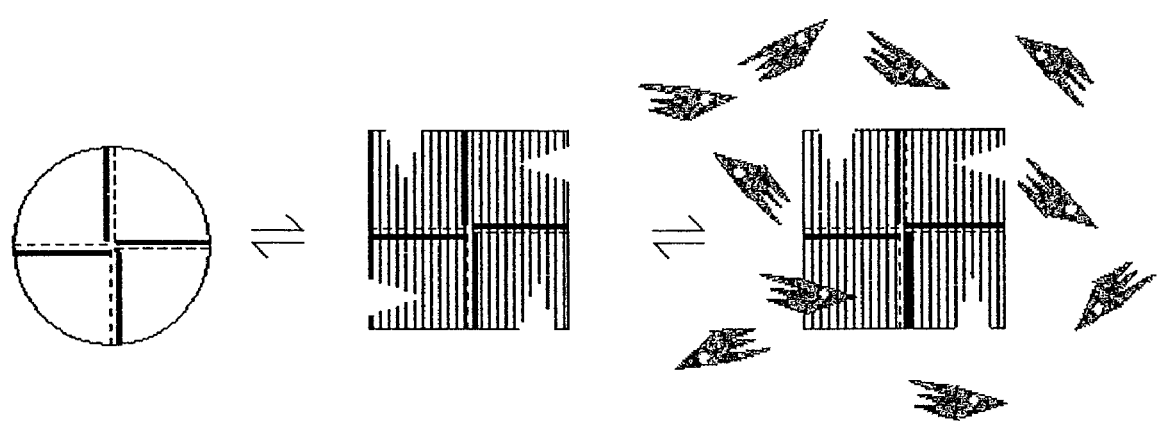
FIG. 1 (prior art) is a classic model for allosteric regulation of protein function. An equilibrium of allosteric states (ON state and OFF state) is illustrated. The allosteric regulators (objects in a shape of a granite fish) can bind to the square tetramer and pull the equilibrium in that direction; oligomer dissociation is not an obligatory part of the equilibration process. This classic model presumes that the stoichiometry of the quaternary assembly of the allosteric protein is constant between the ON state and the OFF state. In this figure, both are tetramers.
Figure 3A:
FIG. 3A (prior art) shows a stereo diagram of one dimer of *E. coli* PBGS, where the protein subunits are shown as ribbon diagram and colored black and light gray. The active site zinc ions are shown as gray spheres, and the allosteric magnesium ions are shown as black spheres. Active site ligands are not illustrated.
Figure 3B:
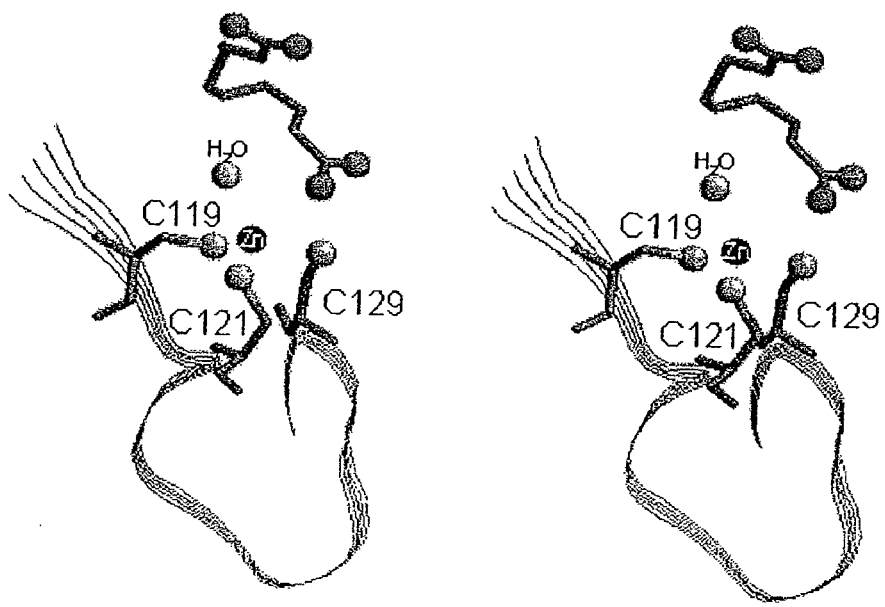
FIG. 3B (prior art) shows a stereo diagram of the structural details of the active site zinc of *E. coli* PBGS. The cysteine ligands are labeled and the cysteine sulfur atoms are shown as white balls. The water is labeled. The active site ligand 4,7-DOSA is shown in gray, with oxygen atoms as balls.
Figure 3C:
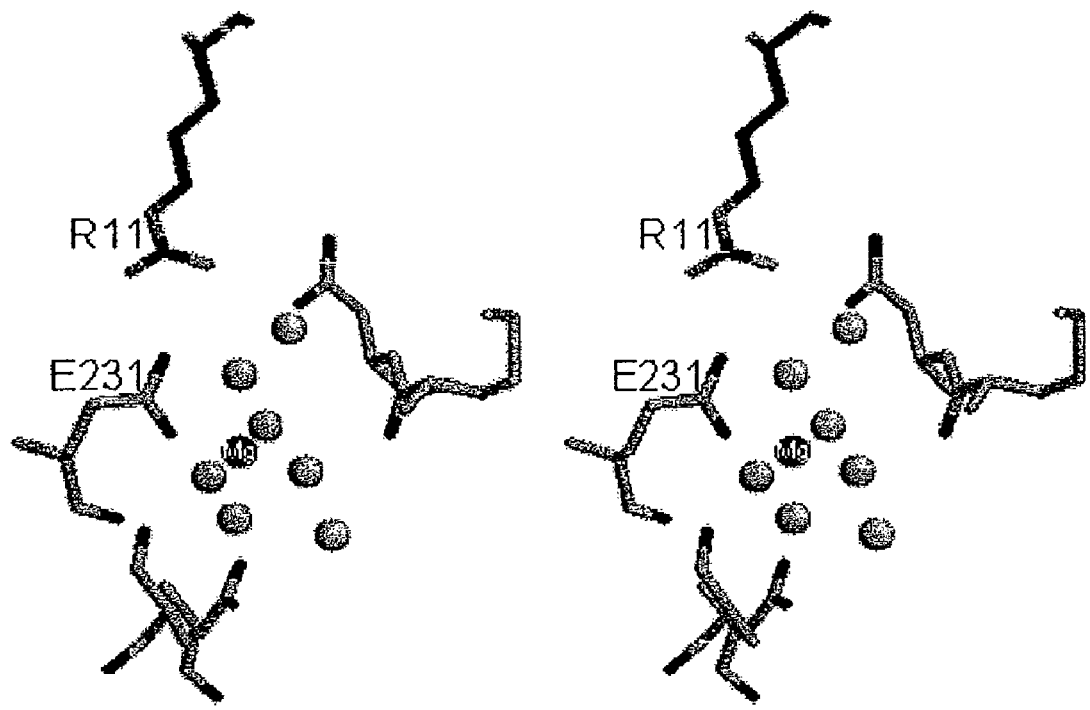
FIG. 3C (prior art) shows a stereo diagram of the structural details of the allosteric magnesium binding site of *E. coli* PBGS. The white balls indicate water molecules, which form an extended ligation network between the magnesium and oxygen and nitrogen atoms of neighboring residues. The amino acids involved in this network are shown as stick diagrams, with carbons colored light or dark according to the chains of FIG. 3A. Oxygen or nitrogen atoms that are involved in the ligation network are shown in a contrasting shade. The labeled amino acid E231 is the only amino acid in the first coordination sphere of the magnesium. R11 derives from the N-terminal arm of the neighboring subunit of the hugging dimer shown in FIG. 3A.
Figure 6:
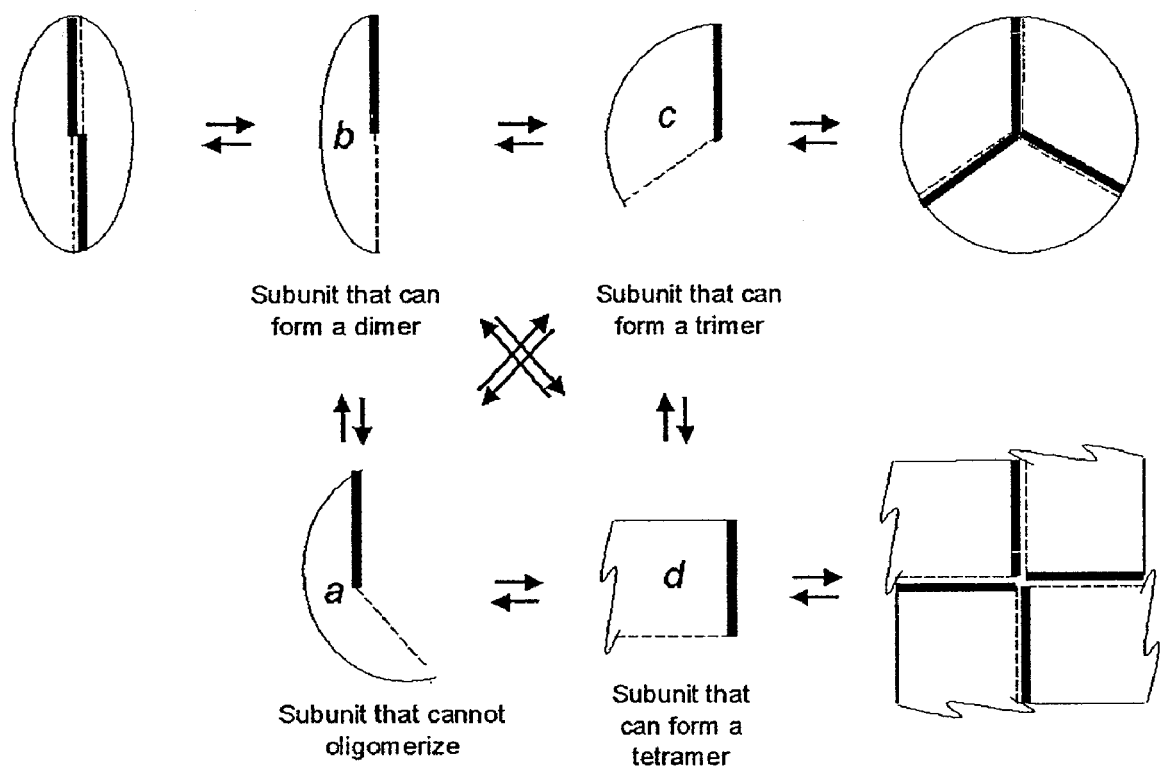
FIG. 6 is a 2-D schematic representation of the morpheein concept of an equilibrium ensemble of protein oligomers—Different conformations of a protein monomer are represented by different shapes (labeled a-d); each shape has one surface that is a dashed line and one surface that is a thick line. For oligomeric assembly, the rule of engagement between any two monomers is the association of the dashed line with the thick line. Four possible alternative conformations are shown for the monomer and each of these conformations dictates a different quaternary structure. Conformation (a) cannot oligomerize because it is not geometrically possible to satisfy the rule of engagement in two dimensions. Conformation (b) can completely satisfy the rule of engagement by forming a dimer after which oligomerization is complete. Conformation (c) can completely satisfy the rule of engagement by forming a trimer. Conformation (d) can completely satisfy the rule of engagement by forming a tetramer. Within this framework, the dimerization of a protein involves an equilibrium between three species. These are the monomer conformation that cannot form a dimer (a), the monomer conformation that can form a dimer (b), and the dimer (of b).
Figure 7:
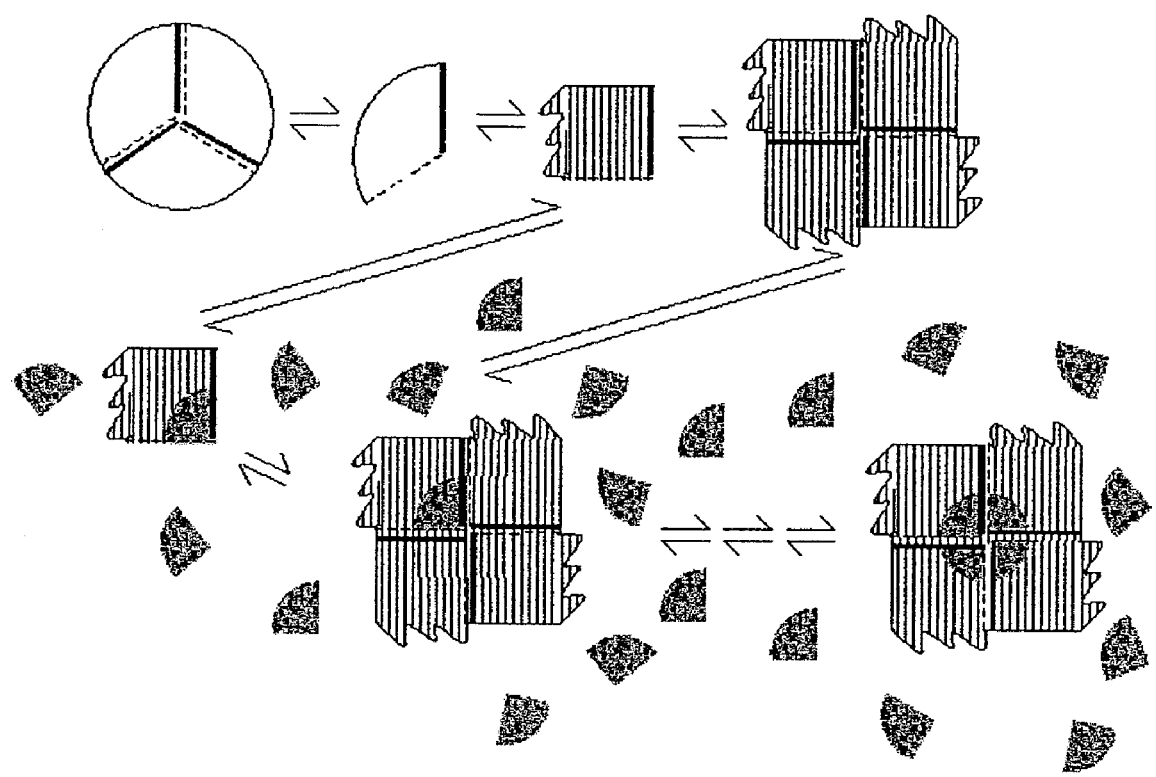
FIG. 7 illustrates the alternate representation of allosteric regulation as an equilibrium of morpheeins. The defining characteristics of this MORPHEEIN MODEL OF ALLOSTERIC REGULATION are that 1) the structure of the monomer dictates alternate stoichiometries for the oligomers (round trimer, square tetramer) and 2) there is a requisite dissociation and reassociation of fundamental units. The granite substance represents the allosteric regulator, which functions to draw the equilibrium toward the square forms by acting as a wedge and inhibiting the interconversion of monomeric forms. In the morpheein representation the change in oligomeric state is more complex than a simple association/dissociation phenomenon. A morpheein equilibrium involves a dramatic change in the conformation of the (at least partially dissociated) monomeric unit. The morpheein concept provides a novel structural paradigm for allosteric regulation, which is fundamentally different from that which is illustrated in FIG. 1.

The unexpected behavior of the enzyme porphobilinogen synthase led the inventor to propose that this, and perhaps also other, proteins could defy the Anfinsen paradigm (one protein one structure) [1] and could exist as more than one physiologically relevant quaternary assembly where each quaternary assembly was the natural outcome of an alternate conformation for the monomeric unit. These alternate quaternary assemblies are given the name morpheeins. A two dimensional schematic representation of morpheeins as alternate quaternary assemblies of homo-oligomeric proteins is shown in FIG. 6. The morpheeins of PBGS, the structures of which are described in detail below, and the inventor's knowledge that some PBGS are subject to allosteric regulation, led to the proposal of the morpheein model of allosteric regulation of protein function, which is illustrated in FIG. 7, and is fundamentally different from all previously proposed models for allosterism (as illustrated in FIG. 1). The morpheein model for allosteric regulation requires that the oligomeric protein must dramatically rearrange as part of the allosteric transition from the ON state to (or from) the OFF state.

Figure 8:
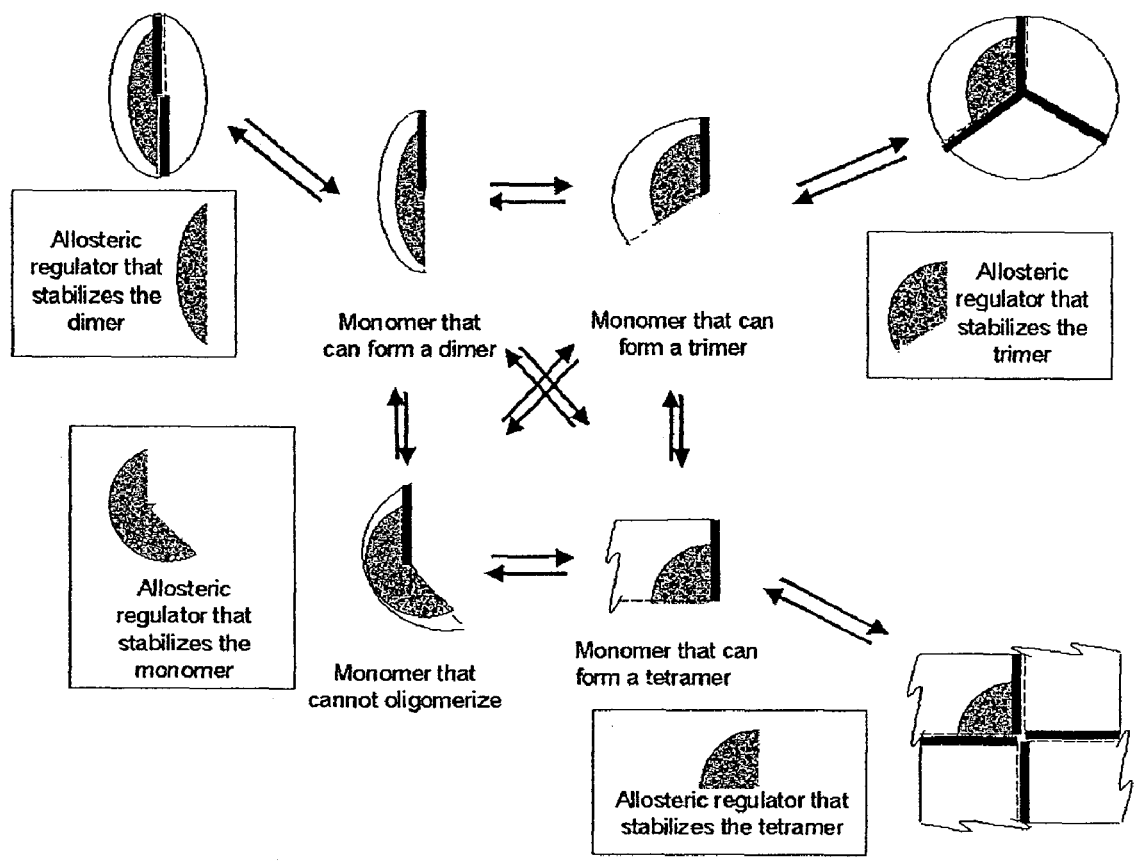
FIG. 8 is a two-dimensional schematic representation of the equilibrium between units and oligomers involving an allosteric regulator (agent). The allosteric regulator is shown as a filled gray shape bound to either a unit or to a multimeric protein. The allosteric regulator is capable of perturbing the equilibrium between oligomeric states. This figure illustrates wedges that will shift the equilibria illustrated in FIG. 6.

This invention provides a novel way to think about how different oligomerization states, such as those involved in signaling and cell cycle control, can up-regulate or down-regulate pathways. In accordance with the invention, the activity of any protein whose allosteric regulation can be defined by an equilibrium among "morpheeins" can be modulated by agents (e.g., small molecules) that bind to the unique surface features of one or another of these morpheeins and thus shift the equilibrium of quaternary forms, as illustrated in FIG. 8. Because the binding sites for these agents can be surface pockets that are peculiar to a specific morpheein shape, they are not generally expected to contain phylogenetically conserved sequences, thus allowing species specificity. Porphobilinogen synthase is presented as the prototype morpheein system subject to allosteric regulation and the most specific embodiments of the invention are related to inhibition of porphobilinogen synthase through stabilization of one or more less active (OFF state) morpheeins.

According to certain embodiments of the invention, tetrapyrrole biosynthesis can be modulated by modulating the equilibrium among the morpheeins of PBGS. According to certain embodiments of the invention, inhibitor molecules can be discovered that will preferentially interact with the unique surface components of the PBGS hexamer and displace the distribution of morpheeins toward the hexameric form (which in the case of plant and some bacterial PBGS is believed to be the inactive form).

Advantageously, the invention provides a composition comprising an agent adapted to affect a multimeric protein by binding to a binding site of said multimeric protein and thereby affecting an equilibrium of units, wherein said multimeric protein comprises an assembly having a plurality of said units, wherein each of said units comprises a first complementary surface and a second complementary surface and wherein the first complementary surface of one unit is associated with the second complementary surface of another unit, provided that the assembly is at least one of different quaternary isoforms on a condition that in said multimeric protein (1) a structure of each of said units determines a structure of said different quaternary isoforms, (2) said units are in the equilibrium and (3) the structure of said different quaternary isoforms influences a function of the multimeric protein. The composition of the invention can be used for inhibiting or preventing development or growth of bacteria, archaea, and/or eucarya in a host organism. For example, the composition of the invention can be used in form of a drug, a toothpaste, a soap, a disinfectant, an anti-biofilm composition, and a herbicide. The invention provides guidance to selection of a target organism and influencing it to achieve a desired effect.

The unit of the multimeric protein can be, for example, a monomer, a dimer, a trimer, a tetramer, a hexamer, and an octamer. In certain embodiments, affecting said multimeric protein comprises affecting a formation of a quaternary isoform. In certain embodiments, affecting said multimeric protein comprises affecting the function of said multimeric protein. A non-limiting example of a function of said multimeric protein is an activity and wherein "affecting" is at least one of inhibiting or activating. As described further below, depending on the application, the agent can be bound to at least one of a quaternary isoform having a lesser activity or a quaternary isoform having a greater activity, thus inhibiting or activating the multimeric protein.

Exemplary multimeric proteins are porphobilinogen synthase and a ribonucleotide reductases, such as Class Ia ribonucleotide reductase (highly regulated enzymes responsible for balancing the deoxyribonucleotides that are required for DNA replication).

The following five systems have been identified as potential morpheein systems. The first is *Pseudomonas aeruginosa* GDP-Mannose dehydrogenase, which is a key regulatory enzyme in the biosynthesis of alginate, the polysaccharide that encapsulates the human pathogen *P. aeruginosa*, thus helping to create a protective biofilm. The second is *Bacillus subtilis* HPr (histidine containing phosphocarrier protein), kinase/phosphatase (HPrK/P) of most gram-positive (and some gram negative) bacteria, which is involved in the regulation of carbon catabolite repression/activation. Regulation of this enzyme allows bacteria to adapt rapidly to environmental changes in carbon sources. The third is mammalian CoA transferase, which is a mitochondrial enzyme essential for the metabolism of ketone bodies. The fourth is purine nucleoside phosphorylase (PNP) enzymes, which play a key role in the purine salvage pathway and are reported to have a variety of oligomeric stoichiometries. The fifth is the family of peroxiredoxins, which area phylogenetically diverse family of proteins that act as antioxidants and in the regulation of cell signaling pathways, apoptosis, and cellular differentiation.

Thus, in certain embodiments, the agent is an inhibitor bound to the quaternary isoform having the lesser activity and wherein the quaternary isoform contains less than eight porphobilinogen synthase monomers. Similarly, when the multimeric protein is the Class Ia ribonucleotide reductase or another morpheein system, the agent inhibits the Class Ia ribonucleotide reductases through selective binding to the binding site that is unique to a less active quaternary isoform.

The invention will now be described using PBGS as an example of a multimeric protein. Thus, the invention provides a composition comprising an inhibitor adapted to inhibit formation of an active form of a multimeric porphobilinogen synthase having a first number of monomers by binding to a less active form of the multimeric porphobilinogen synthase having a second number of monomers, wherein the first number of monomers is higher than the second number of monomers.

Figure 9:
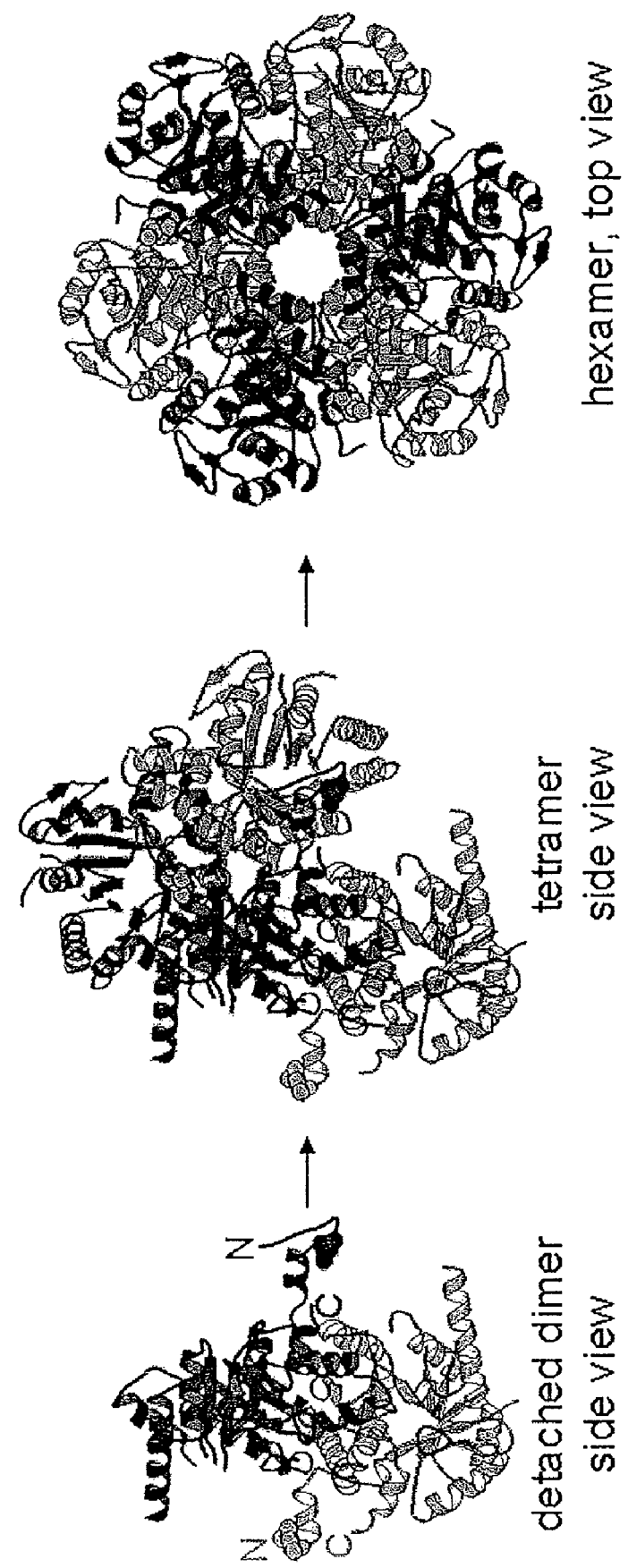
FIG. 9 shows the assembly of hexameric human PBGS variant F12L (PDB code 1PV8). To the left is the detached dimer; in the middle is the tetramer (same orientation as the detached dimer), and on the right is a top down view of the hexamer. For each dimer, one monomer is light gray and the other is dark gray. A comparison of FIG. 9

The inventor has discovered that PBGS can exist in at least two alternate quaternary structures, octamer and hexamer. The multimeric PBGS having a lesser number of monomers of PBGS is also encompassed by this invention. Previously, only the octameric form was known to exist. In both forms, the monomer contains an α8β8 barrel comprised of the C-terminal 300 amino acids, wherein the center of the α8β8 barrel contains the active site. A variable length N-terminal portion of the subunit forms an extended arm structure that is involved in extensive inter-subunit interactions in both oligomeric forms, i.e., octamer and hexamer. A major difference between the two quaternary structures is the conformation of the N-terminal arm. FIG. 2 shows the assembly of octameric PBGS as a tetramer of hugging dimers. FIG. 9 shows the assembly of hexameric PBGS as a trimer of detached dimers.

In certain embodiments, the multimeric porphobilinogen synthase is derived from bacteria, archaea, or eucarya, provided that the octameric porphobilinogen synthase contains an allosteric magnesium binding site. In one variant of this embodiment, the multimeric porphobilinogen synthase contains a catalytic zinc binding site.

Figure 4:
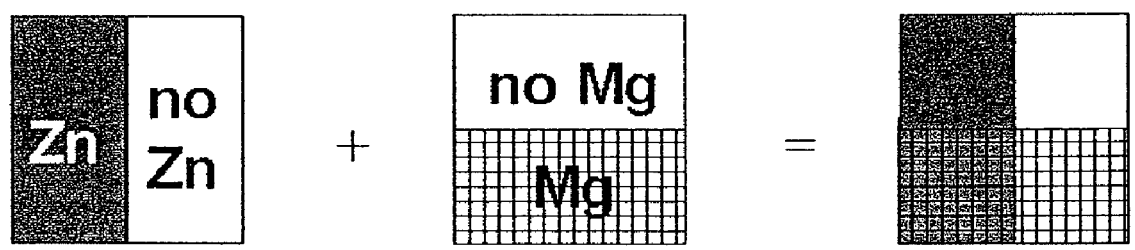
FIG. 4 shows a schematic classification of PBGS according to the independently segregating criteria of the presence of active site zinc (dark gray area, far left), and the absence of active site Zn (white area, left box), the presence of allosteric magnesium (Mg) (checkered area, middle box), the absence of allosteric Mg (white area, middle box). The resulting matrix (far right) consists of four quadrants, wherein the northwest quadrant (QNW) represents +Zn/−Mg, the northeast quadrant (QNE) represents −Zn/−Mg, the southwest quadrant (QSW) represents +Zn/+Mg, and the southeast quadrant (QSE) represents −Zn/+Mg.
Figure 5:
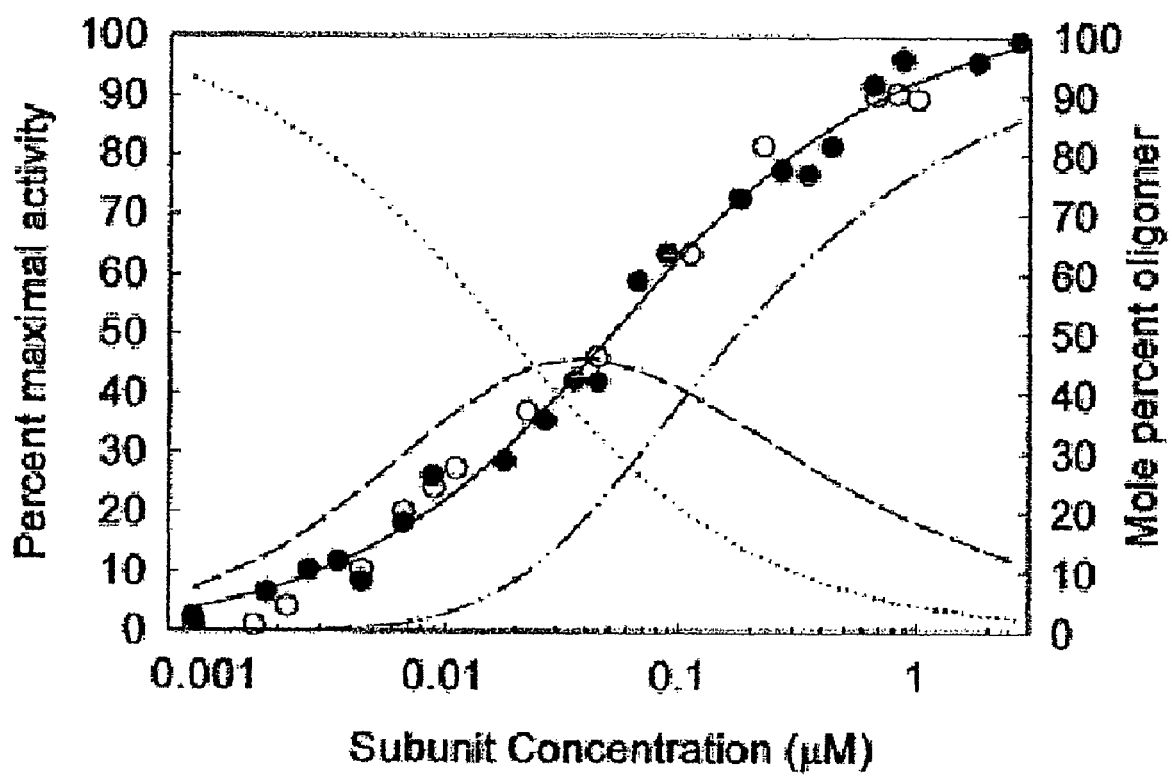
FIG. 5 (prior art) (taken directly from reference [13]) shows the combined data on the protein concentration dependence of PBGS from *P. sativum* (common garden pea, open circles) and *B. japonicum* PBGS (filled circles). The solid line is a simple hyperbolic fit to the data. The other lines depict the mole percent of various oligomers according to a published interpretation of the data wherein the octamer dissociates to tetramers and dimers. The model presumed that the dimer (a dotted line) is inactive, half of the asymmetric units of the tetramer (a dashed line) are active, and all the asymmetric units of the octamer (a dash-dot line) are active.
Figure 10:
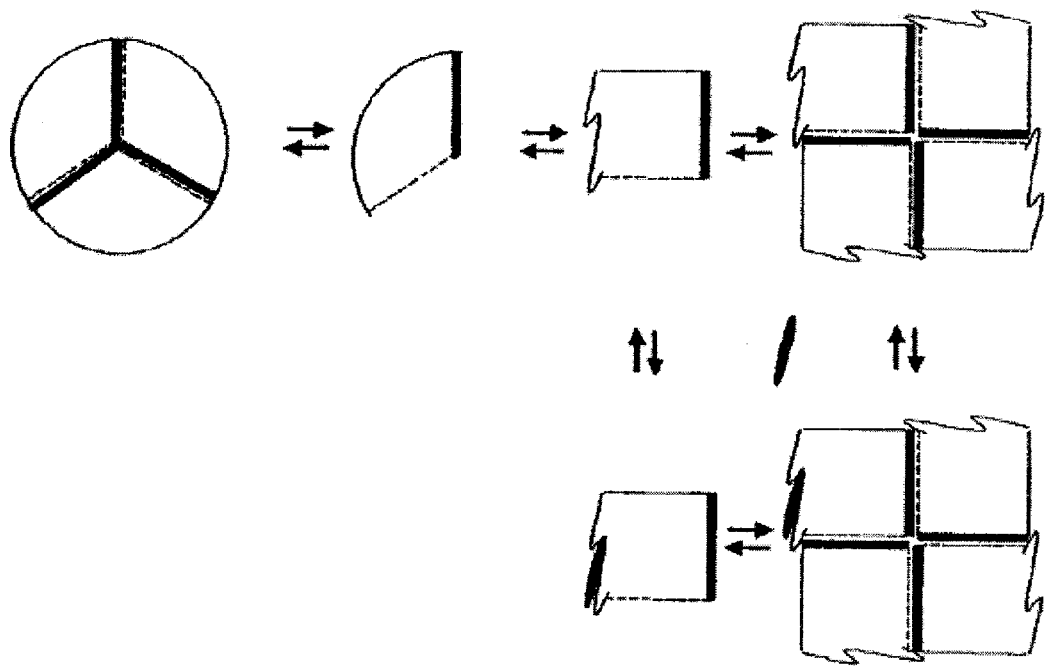
FIG. 10 is a two-dimensional schematic representation of the equilibrium between two isoforms of a protein demonstrating that an agent that is capable of affecting a function of the protein has a binding site on one form of a unit but not on another. In each case, the rules for multimerization are to juxtapose one thick line with one dashed line.
Figure 11:
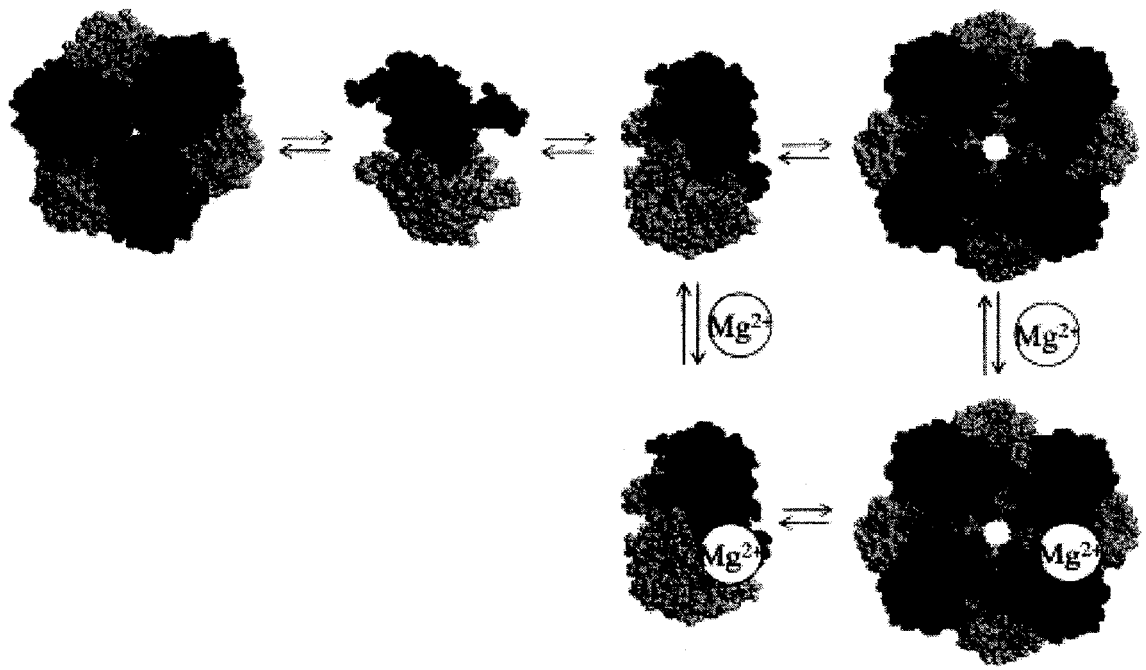
FIG. 11 uses space filling representations to illustrate the equilibrium of PBGS morpheeins, which are (from left to right) the hexamer, the detached dimer, the hugging dimer, and the octamer. The lower portion of the figure illustrates how magnesium stabilizes the morpheeins made up of hugging dimers by stabilizing the arm-to-side-of-barrel interface.
Figure 12:
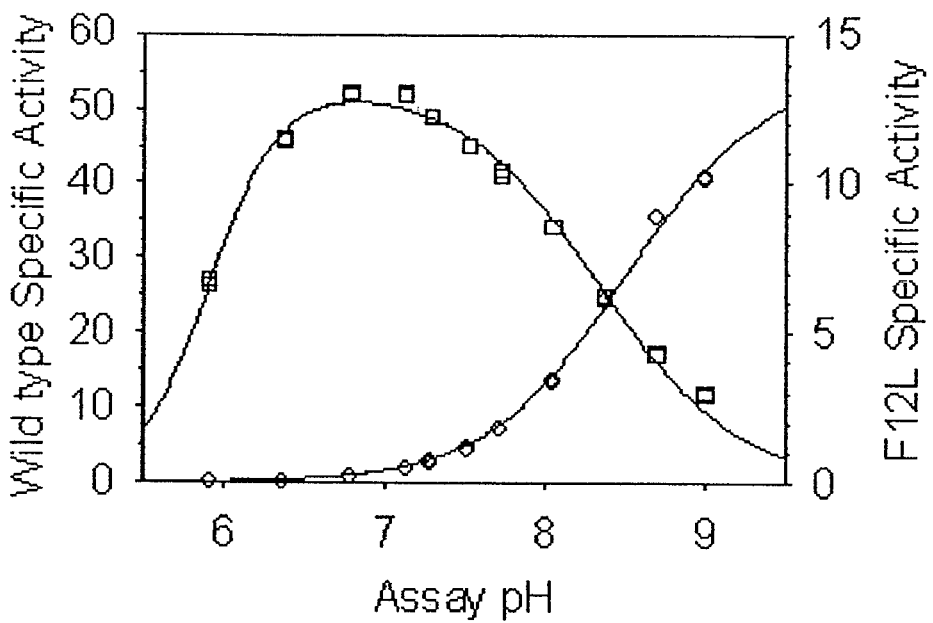
FIG. 12 shows the functional difference between human PBGS WT (open squares) and F12L (open diamonds) in terms of their pH activity profiles.
Figure 14:
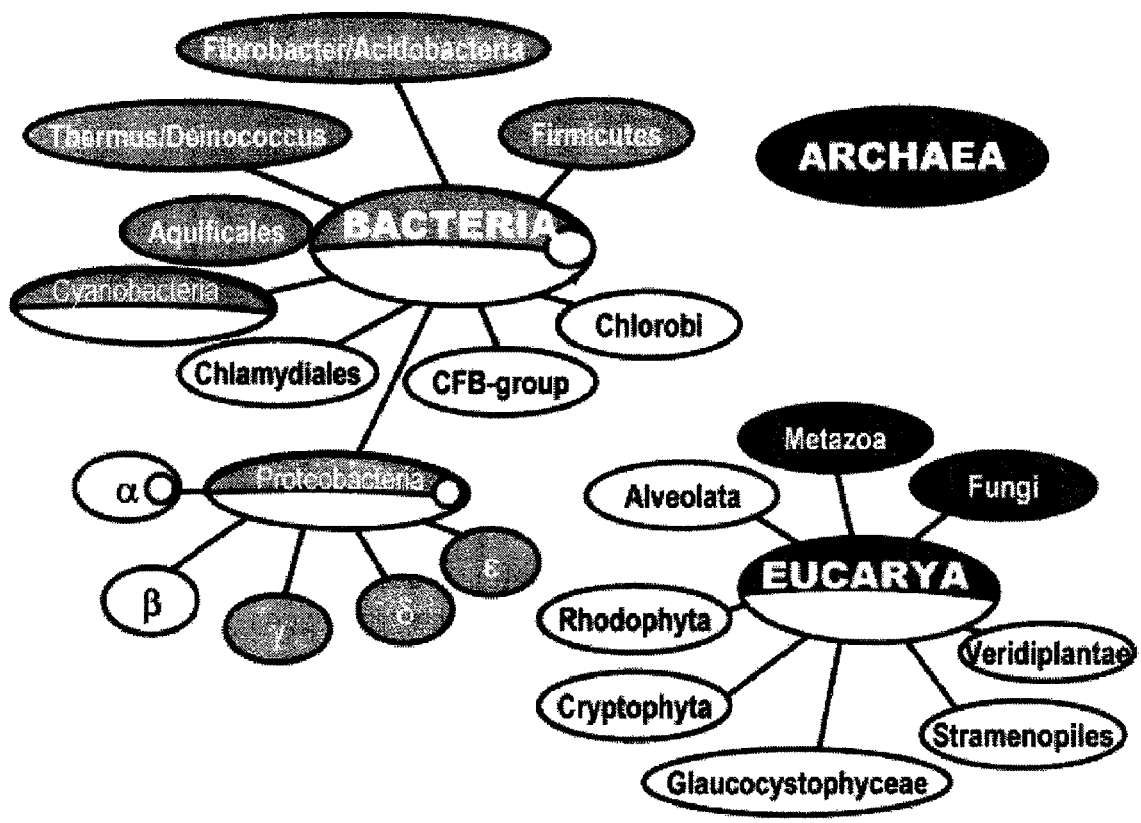
FIG. 14 is a classification of sources for PBGS including bacteria, archaea, and eucarya, wherein distribution of metal binding properties of PBGS is coded in accordance with FIG. 4. From the inventor's experience with PBGS from various sources, the organisms with the white background (checkered or not) are expected to rapidly equilibrate between morpheein forms and thus be susceptible to the inhibitors of this invention.
Figure 16A:
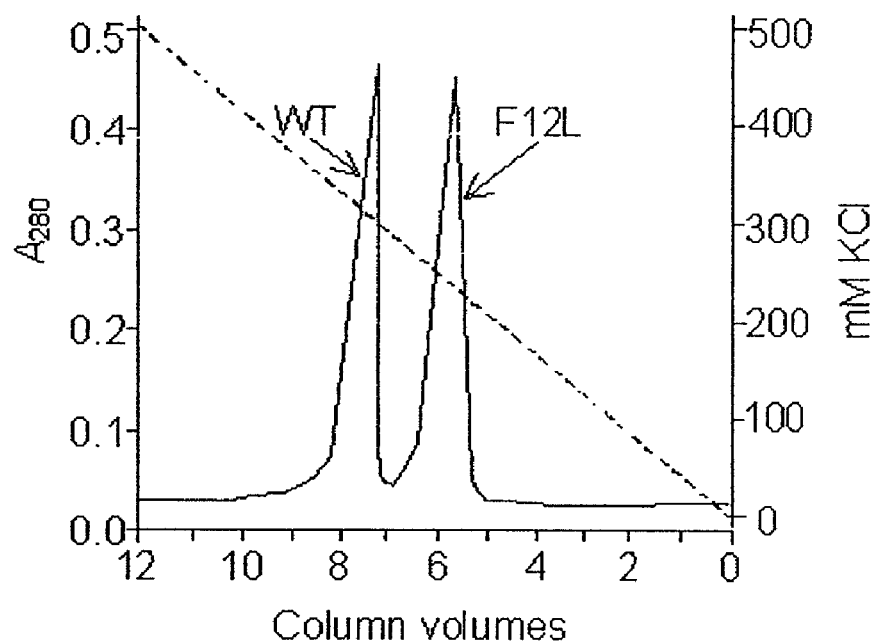
FIG. 16A shows the chromatographic separation of wild type human (WT) PBGS and F12L on a mono-Q column using a salt gradient (dashed line).
Figure 16B:
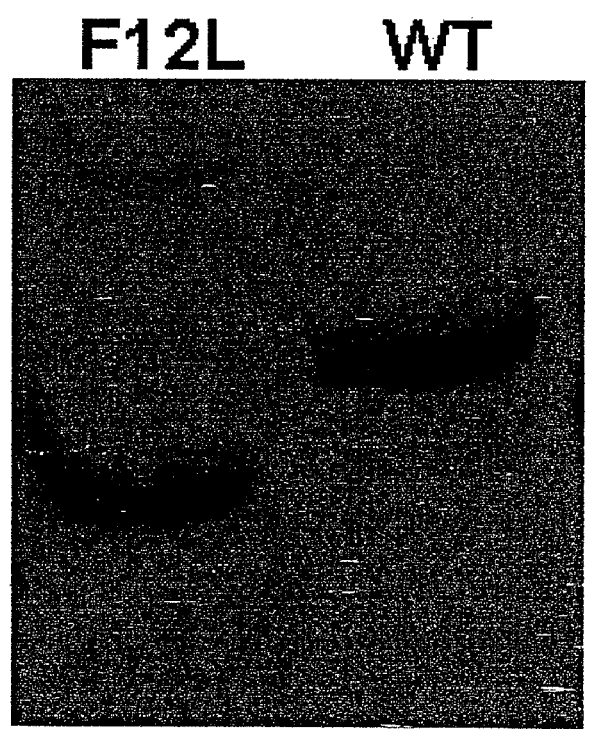
FIG. 16B shows the differential mobility of wild type (WT) human PBGS and F12L on 12.5% polyacrylamide native gel electrophoresis.

Porphobilinogen Synthase as an Example of Morpheeins:

The following describes the discovery that PBGS can exist in alternate quaternary states, which are called herein "morpheeins" (FIGS. 2, 6, 9), that morpheeins can be a structural basis for allosteric regulation (FIGS. 7, 8, 10), and that the interconversion of these states forms the structural basis for allosteric regulation of this PBGS in some species (FIGS. 11, 14). The well known quaternary state for PBGS is the octamer made up of hugging dimers (FIG. 2). Also known was that some PBGS, particularly those in the QSE of FIG. 4, exist as equilibrium of quaternary forms as shown by a protein concentration dependence to the specific activity (FIG. 5). The protein concentration dependence to the specific activity indicates that a maximally active oligomer can dissociate or reassociate into smaller less active forms. It was previously believed that the smaller, less active forms, were also multiplicities of hugging dimers (modeled in FIG. 5). Observation and characterization of a stable oligomer of detached dimers was made possible by the fact that PBGS in the QNW do not readily equilibrate between quaternary isoforms. Hence the F12L mutation of human PBGS allowed the inventor to study a stable form of the hexamer and to establish that it was the hexameric property (and not the specific F12L mutation) that dictated the dramatically different functional properties of F12L relative to wild type human PBGS. F12L is a naturally occurring rare allele for human PBGS [26,27]. Described in EXAMPLE 1 below are studies of human PBGS (both wild type and F12L) that were heterologously expressed in *E. coli* and purified by conventional techniques. The different physical and kinetic properties of wild type and F12L are illustrated in FIG. 12, Table 1, and FIGS. 16A and 16B.

The data presented on wild type human PBGS, the F12L variant, and the WT+F12L heteromers definitively establishes that the kinetic differences between the wild type protein and the F12L variant are primarily due to the difference in quaternary structure as described in detail in EXAMPLE 2 below. Further work on other select human PBGS mutants (R240A, T23P, and T23P/F12L) confirm that the kinetics of the hexamer are like the kinetics of F12L and that the kinetics of the octamer are like that of the wild type protein.

The interconversion of human PBGS morpheeins during turnover (catalytic activity) was hypothesized based on the physical and kinetic characteristics of the heteromeric WT+F12L oligomers, as illustrated in FIGS. 17A-D and Table 3, as described in detail in EXAMPLE 2 below. The disproportionation of these hetero-oligomers during extended turnover proves that the morpheeins of human PBGS can exist in a dynamic equilibrium, as illustrated in EXAMPLE 3.

In light of the structures of octameric vs. hexameric human PBGS, a hypothesis can be formulated concerning the dramatic difference in pH optimum for these two forms of PBGS. The chemistry of the PBGS catalyzed reaction requires the formation of at least two Schiff base intermediates [28]. Formation of the carbinolamine precursors to these Schiff bases requires that the participating amino groups are uncharged, or that the local pH is above the $pK_a$ of the amino groups. One significant structural difference between hexameric and octameric PBGS is the degree of order found in the amino acids that comprise the active site lid. The crystal structure of hexameric PBGS F12L is lacking in density from most of the residues that make up the active site lid, thus implying that the hexamer structure destabilizes the closed lid configuration. In the absence of a closed lid to isolate the active site from bulk solvent, the PBGS catalyzed reaction cannot proceed until the external pH is above the $pK_a$ of the amino groups that participate in Schiff base formation. Hence, the hexameric structure is proposed to exhibit activity only when the external pH is sufficiently basic to facilitate Schiff base formation. The high $K_m$ can also be attributed to destabilization of the active site lid since crystal structures of the PBGS octamer show stabilizing interactions between residues on the lid and the substrate molecule that determines the Km value. The current results provide a novel approach to understanding the regulation of PBGS function. As described below, the insight provided from identification of a PBGS hexamer has considerable significance for rethinking the allosteric regulation of PBGS activity in non-human species.

Figure 18A:
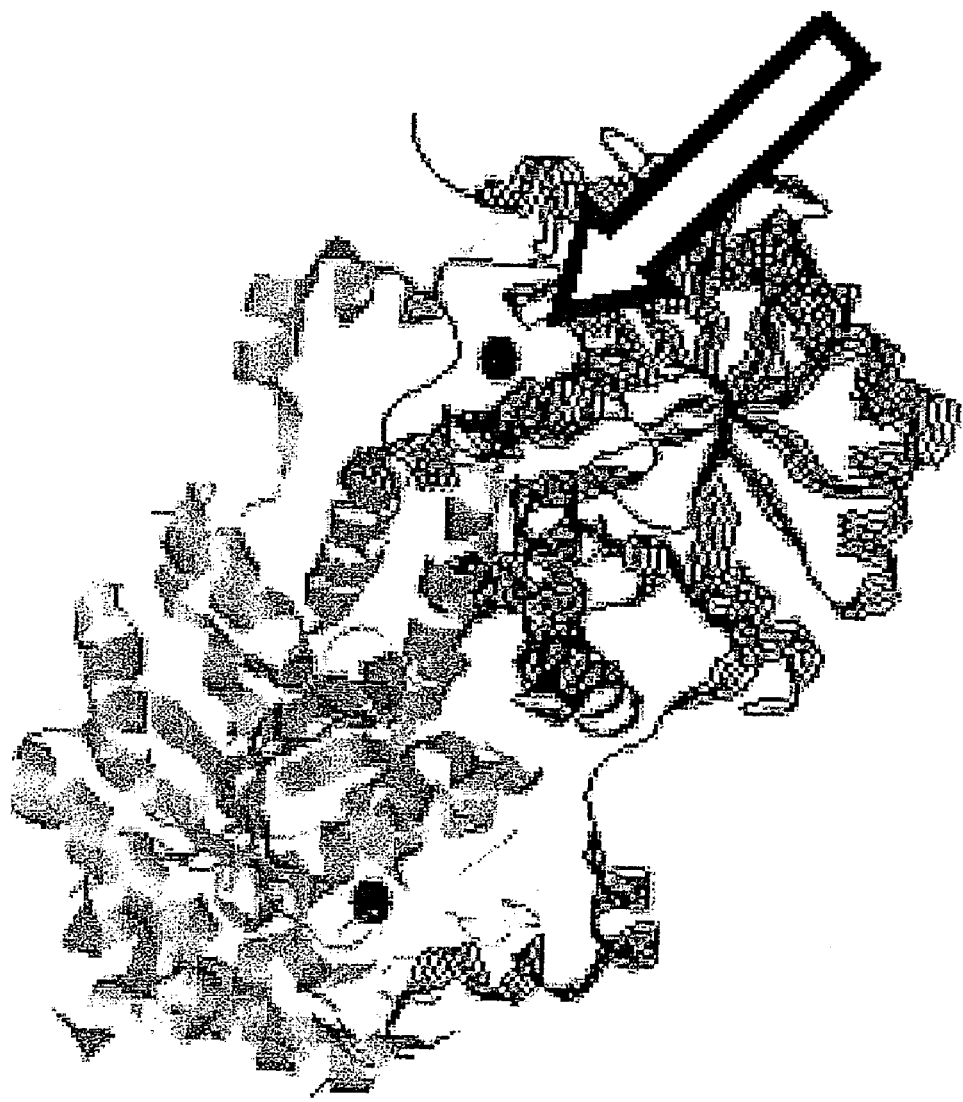
FIG. 18A shows a ribbon diagram representation of the crystal structure of the hugging dimer of E. coli PBGS; the arrow indicates the location of the allosteric magnesium.
Figure 19A:
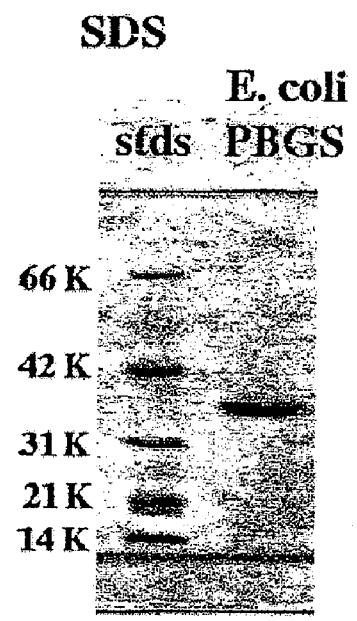
FIG. 19A shows an SDS gel of purified E. coli PBGS.
Figure 19B:
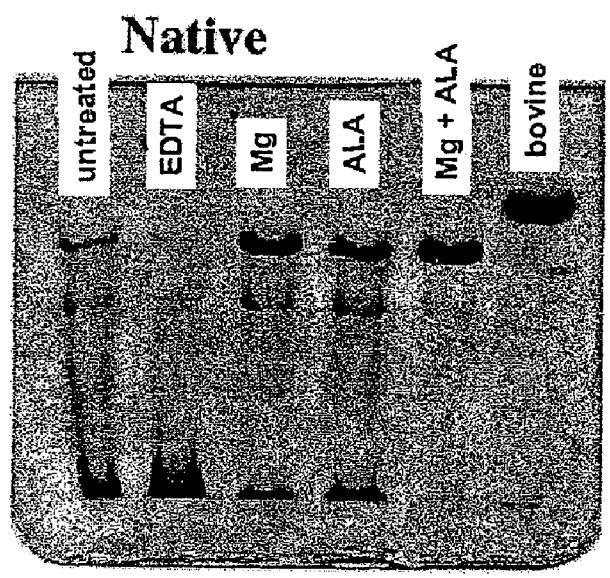
FIG. 19B shows a native gel of E. coli PBGS (12.5% acrylamide). Untreated protein is shown in the far left lane. The bands have mobility consistent with (top to bottom) octamer, hexamer, tetramer, and dimer. The following lanes shows that addition of the magnesium chelator EDTA, magnesium, ALA, or magnesium plus ALA can shift the equilibrium of E. coli PBGS morpheeins in the native gel environment. Removal of magnesium by EDTA favors the dimer. Addition of excess magnesium or the substrate ALA or both favors formation of the octamer. The far right lane shows bovine PBGS, which like human PBGS runs as a single band. The octamer of bovine PBGS has a different charge than the octamer of E. coli PBGS and thus runs at a different mobility on the gel.

Allosteric Regulation of PBGS can be Attributed to the Octamer to Hexamer Equilibrium:

Comparison of the PBGS octamer and hexamer reveals a basis for allosteric regulation of PBGS. Despite the fact that all the obvious components of the PBGS active site are contained in the monomer, most PBGS proteins contain a binding site for an allosteric magnesium that is located at the arm-to-barrel interface of the hugging dimer [11,29]. The position of the allosteric magnesium is seen in the crystal structures of both *Pseudomonas aeruginosa* [29] and *E. coli* PBGS [30], as illustrated for the latter in FIG. 18A. FIG. 18A shows the hugging dimer (light ribbon, dark strand) with the allosteric magnesium as black balls, one of which is illustrated with a large white-on-black arrow. The structures of yeast and human PBGS show that the guanidinium group of an arginine resides in the place of the allosteric magnesium as illustrated previously [9]. This is Arg240 of human PBGS. If one presumes that all PBGS can exist in the hexameric state under appropriate conditions, then the position of the allosteric magnesium is pertinent to a hexamer-octamer transition because this metal binding site is present in the octamer (made up of hugging dimers) and absent in the hexamer (made up of detached dimers). FIG. 18B shows the three subunit to subunit interfaces in the PBGS octamer. The black-on-white arrow shows the barrel-to-barrel interface, which is common to both octameric and hexameric PBGS assemblies. The dots-on-black arrow shows the arm-to-base-of-barrel interaction, which is also common to both octameric and hexameric PBGS assemblies. The white-on-black arrow, which is analogous to the allosteric magnesium binding site, shows the arm to barrel interaction that is present in the octamer (hugging dimer) and absent in the hexamer (detached dimer). Consistent with the notion that the allosteric magnesium mediates a hexamer-octamer equilibrium is the effect of magnesium on the kinetic parameters of *E. coli* PBGS. In this case, the addition of the allosteric magnesium causes the $K_m$ value to decrease from ~2 mM to ~200 μM [31], which is remarkably reminiscent of the difference between the $K_m$ values of the hexameric and octameric forms of human PBGS (Table 1). Also of note is the inventor's prior observation that homogeneously pure *E. coli* PBGS shows multiple bands during native gel electrophoresis, that the mobility of these bands is consistent with the molecular size of octamer, hexamer, tetramer and dimer, and that addition of magnesium favors the largest (octameric) form [31] (reproduced in FIG. 19). Also of note is the recent finding that the human PBGS variant R240A purifies ~80% as the hexamer and 20% as the octamer, and that the latter oligomer is unstable and rearranges to the hexamer with time.

Observation of Protein Concentration-Dependent Specific Activity is One of the Diagnostic Tools for the Presence of an Equilibrium of Morpheeins Interconversion of PBGS between hexamer and octamer is proposed as the mechanism responsible for the protein concentration-dependent specific activity of PBGS from some species. To date, the inventor has characterized four different PBGS that contain the allosteric magnesium. The enzymes are from the species *E. coli* (a γ-proteobacter), *B. japonicum* (an α-proteobacter), *P. aeruginosa* (a γ-proteobacter), and *Pisum sativum* (a green plant). The last three are different from human PBGS in that they do not use an active site catalytic zinc [11] and they also share the unusual property of protein concentration dependent specific activity [13,14,32] (see FIG. 5). The latter property indicates that a maximally active oligomer can dissociate into less active or inactive smaller forms. Published mathematical models, as illustrated in FIG. 5, have considered maximally active octamers dissociating into less active or inactive tetramers and/or dimers [13,14].

Figure 20A:
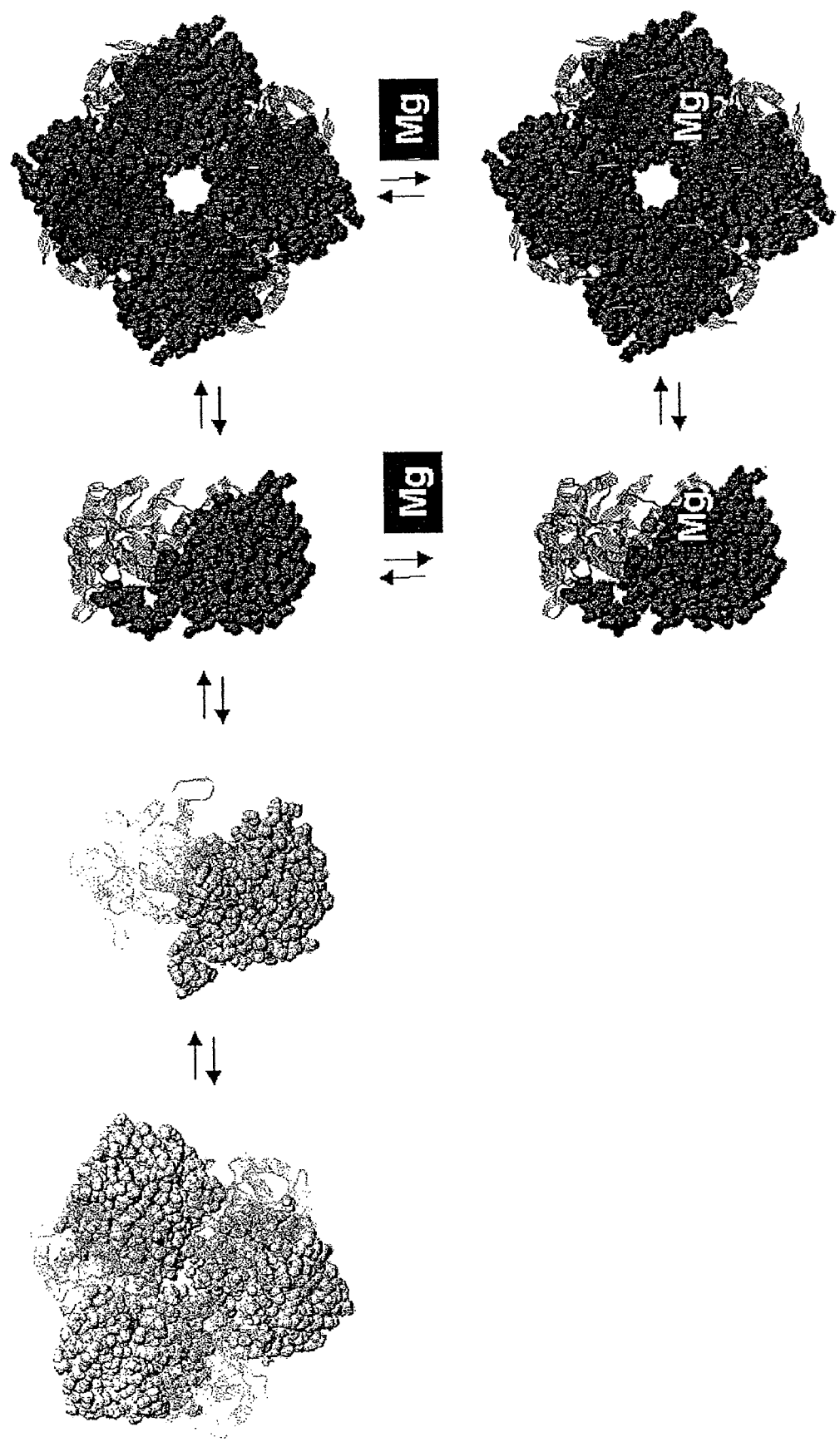
FIG. 20A shows a schematic of the equilibrium of pea PBGS morpheeins, using darker shades for the hugging dimer forms and lighter shades for the detached dimer forms. This figure utilizes models of pea PBGS.
Figure 20B:
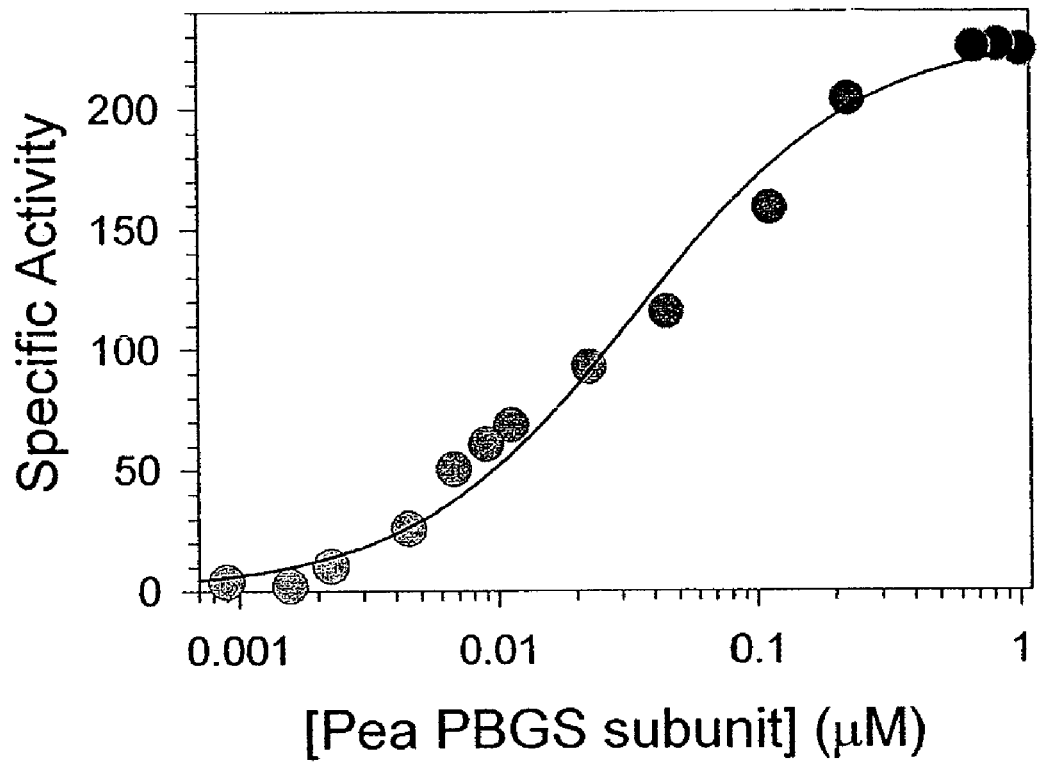
FIG. 20B shows the protein concentration dependence of pea PBGS, coloring the data points according to the interpretation that low activity corresponds to the detached dimer forms and high activity corresponds to the hugging dimer forms (as per FIG. 20A).
Figure 20C:
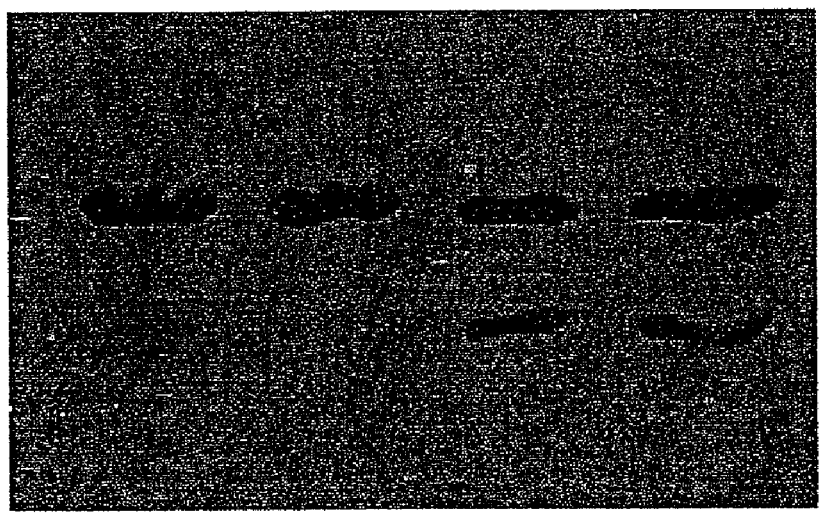
FIG. 20C shows a native gel illustrating the effect of EDTA on the equilibrium of octameric and hexameric pea PBGS. As per FIG. 20A, removal of magnesium by EDTA destabilizes the hugging dimer forms.

The hexameric structure of human PBGS variant F12L leads the inventor to believe that the protein concentration dependence of plant and certain bacterial PBGS is rather due to an equilibrium between a less active hexameric form and a more active octameric form, as illustrated in FIGS. 20A and 20B. The existence of such an equilibrium is supported by sedimentation equilibrium studies on pea PBGS. Because magnesium is integral to the difference between the hugging-dimer and the alternative detached-dimer, this ion is believed to favor formation of the hugging-dimer and, hence, the octamer. FIG. 20C illustrates that removal of magnesium from pea PBGS disfavors the largest form in favor of a smaller form, where the mobility of the two forms is consistent with that of octamer and hexamer. In the model, the hexamer is a putative storage form of the PBGS protein because it is less active at physiologic pH and is characterized by a $K_m$ value that is well above the physiological concentration of ALA. By contrast, the octamer is active at physiological pH and has a $K_m$ value that is in the proper range of ALA concentrations during active tetrapyrrole biosynthesis.

Together, these studies support the belief that there is a role for PBGS in the complex control of chlorophyll biosynthesis [33-35]. One documented occurrence during the greening of plants is a dramatic increase in the magnesium concentration in the chloroplast from <1 mM to >10 mM [36]. The Kd for the allosteric magnesium of pea PBGS is physiologically reasonable at 2.5 mM [13]. One can imagine that an inactive hexameric storage form allows rapid activation of PBGS as part of a cascade of biochemical changes that accompanies the greening process. Several gel filtration studies on the quaternary structure of plant and algae PBGS concluded that the oligomer was a hexamer [37], but these studies preceded determination of the crystal structure of the octamer and they did not consider that an octamer-hexamer equilibrium might exist. Literature support for the existence of interconvertible quaternary forms of PBGS separable by anion exchange chromatography can be found in an early report on PBGS from *Chlorella regularis* [38], but again these investigators were reporting on an unusual phenomenon and did not indicate any premonition of the existence of morpheeins.

Hexameric human PBGS reveals a novel structural paradigm for allosteric regulation of protein function and is the first example of a protein that can exist as morpheeins.

Characterization of the human PBGS variant F12L reveals that this point mutation causes a dramatic change in the structure and function of PBGS. This mutation can serve as a precedent for a single amino acid change resulting in significant changes in protein behavior during evolution. The F12L mutation destabilizes the PBGS octamer and leads to formation of hexamers. The structural transition between octamer and hexamer must proceed through an unprecedented equilibrium containing two different dimer structures. The allosteric magnesium, present in most PBGS has a binding site in the octamer, but not in the hexamer. Native gel data indicate that removal of the allosteric magnesium favors formation of the hexamer over the octamer (see FIG. 20C). The octamer-hexamer transition defines a novel mechanism for metal ion-dependent allosteric regulation of protein function.

This invention describes inhibition of protein function through stabilization of the inactive morpheein of PBGS and/or any other protein that might be regulated by the interconversion of morpheeins. In order to decipher molecules that will selectively bind to and stabilize the hexameric form of PBGS, the inventor is taking the following approach. Only those PBGS in QSE (see FIGS. 4 and 14) are currently being considered as targets because these PBGS have been shown to be active as octamers but they exhibit the protein concentration dependent specific activity phenomenon. The target molecule is one that will selectively bind to the "arm pit" of the hexamer as illustrated by the balls in FIG. 13. The inventor is taking an "in silico" approach of searching molecular libraries for molecules that will bind to the hexameric form of PBGS from the target organisms.

A similar approach can be used for other proteins that can be regulated by the interconversion of morpheeins. It is necessary to have a crystal structure of the less active morpheein, or model thereof, and the localization of a unique surface binding pocket on this target morpheein that is not present on the active morpheein. In some cases it will be required to have crystal structures representative of both the active and inactive morpheeins in order to localize a unique binding pocket. In other case, it may be possible to consider the structure of the inactive morpheein in conjunction with biochemical or biophysical data on the active morpheein to predict the unique surface binding pocket. Examples 5 and 6 describe the proposed unique surface binding pocket for GMD and for HPrP/K.

Homology Model Building for Target Hexameric PBGS

As of 2005, the only existing crystal structure on which the inventor bases a model of target hexameric PBGS is that of human PBGS clinical variant F12L, PDB code 1PV8 [39] Unfortunately, the crystal structure of F12L shows significant disorder, which limits its use as the sole foundation for homology model building. However, comparison of human PBGS octameric and hexameric structures (PDB codes 1E51 and 1PV8) show near identity for the ~300 amino acids that comprise a TIM-like alpha, beta-barrel domain. For human PBGS, the difference between octamer and hexamer lies in the structure of the 24 amino terminal amino acids and various regions that are more disordered in the hexamer [39]. Hence, one can use a higher quality crystal structure of a PBGS octamer for homology model building the alpha, beta-barrel domain of target PBGS. The chosen structure is PDB code 1GZG [40] describes a highly ordered, high resolution crystal structures of Pseudomonas aeruginosa PBGS, itself a target for inhibitors that would "trap" the PBGS hexamer. A hexameric form of P. aeruginosa PBGS was built using various capacities of Swiss-PDB Viewer (www.expasy.ch/spdbv/mainpage.html) and other programs. To build the P. aeruginosa PBGS hexamer, the N-terminal arms were removed from the structure file for the 1GZG dimer. The resulting alpha, beta-barrel domains (residues 32-335) were successively overlaid upon the three dimers of hexameric 1PV8 to create a hexameric assembly of P. aeruginosa PBGS alpha, beta-barrels. There is no significant sequence identity between the N-terminal arms of human and P. aeruginosa PBGS, but there is a conserved alpha-helix in the structure of the N-terminal arm. Hence, a structure alignment of octameric forms of human PBGS and P. aeruginosa PBGS was used to determine the proper sequence alignment for this alpha-helical segment. This information was used to spatially position the amino acids 22-29 of P. aeruginosa PBGS in the hexamer. The program Loopy [41] was used to model amino acids 29-32, so as to connect the N-terminal alpha-helix to the alpha, beta-barrel domain of each subunit. Finally, the remaining N-terminal amino acids, which are present in file 1PV8, were built onto the P. aeruginosa PBGS structure using phi, psi, and omega angle information for the corresponding amino acids of hexameric human PBGS. Due to disorder in some of the N-terminus of the human PBGS hexamer (1PV8), the hexamer model for P. aeruginosa PBGS is missing residues 1-9 of subunits A, C, and E as well as residues 1-11 of subunits B, D, and F. The hexameric P. aeruginosa PBGS was the foundation structure for building a model of hexameric pea PBGS using well established published methods as has been done before [16].

Figure 21:
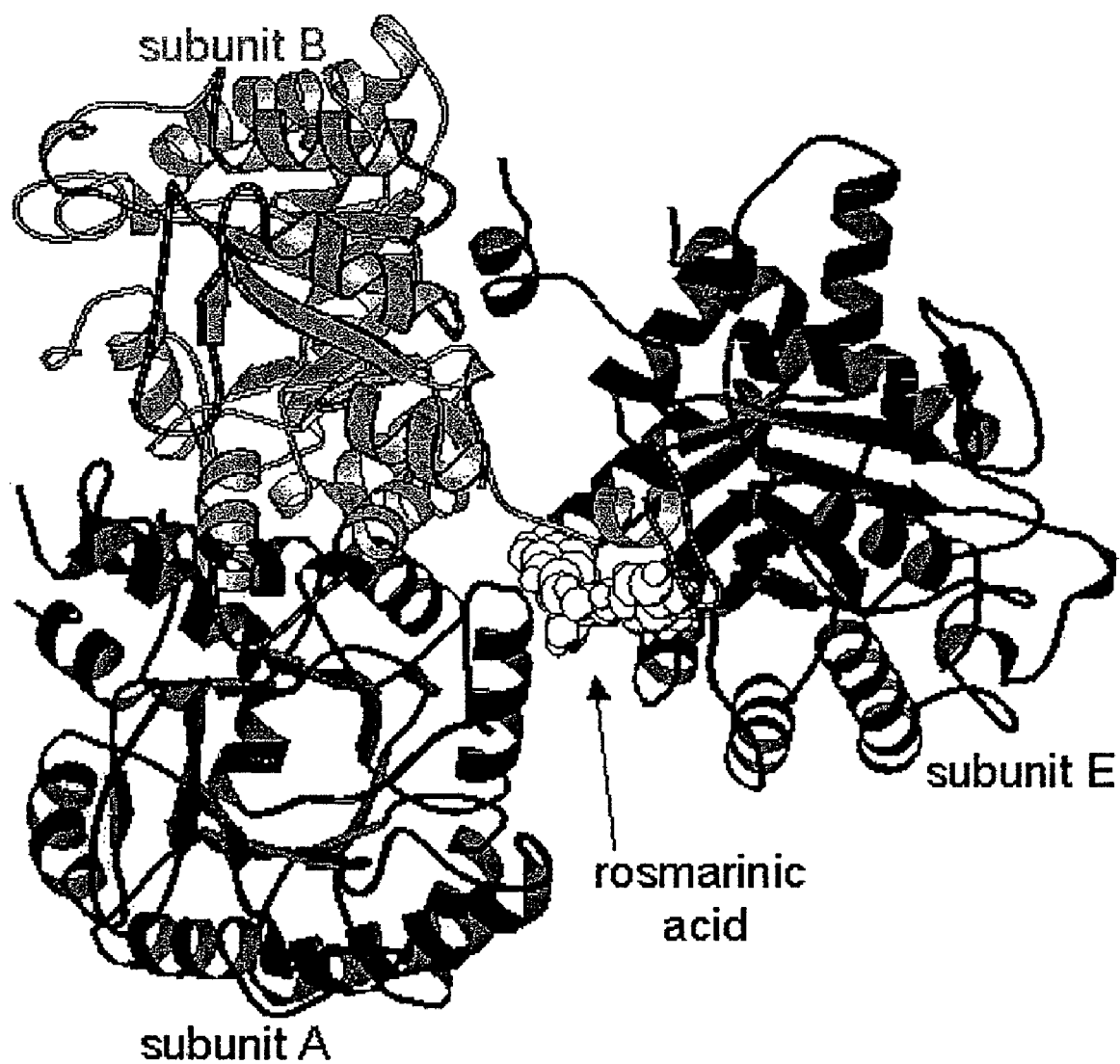
FIG. 21 shows three subunits of the model of the hexameric morpheein of pea PBGS. Rosmarinic acid is shown docked into the putative drug (one example of this invention) binding site.

In searching for molecules that will preferentially bind to hexameric PBGS, the following was discovered. Analysis of the hexamer of PBGS shows that the putative "inhibitor" binding site (also referred to as the arm-pit) contains elements of the three subunits A, B, and E. Subunits A and B comprise the already defined "detached dimer", where the bottom subunit (subunit A, FIG. 21) is typically depicted such that the reader is looking directly into the active site, which is in the center of the alpha, beta-barrel. Subunit B shares a barrel-to-barrel interface with subunit A. Subunit E shares a mutual interaction with subunit B wherein the N-terminal arm of one subunit is nested into the base of the alpha-beta-barrel of the other subunit. The arm-pit of the trimer shown was used as the "binding site" in a computational search of small molecules. The process of using a computational approach to fit small molecules into this site is called docking. The docking program that was used is Glide [42,43], which holds the protein as a rigid body and allows the small molecules to sample many conformations in search of the best complement (shape, charge) to the binding site. This process is called docking. FIG. 21 shows the docked inhibitor, rosmarinic acid, described below. In this docking result, rosmarinic acid has direct interactions with all three subunits shown in FIG. 21.

A variety of "Small Molecule" molecular libraries was used, which have been assembled by the collaborator George Markham, and the docking process attempts to discover molecules that will trap PBGS in the hexameric form. Initial library screening focused on metabolites and natural products. To date, out of a molecular library of ~1,000,000 molecules, ~30,000 have been screened for molecules that will bind to the "arm pit" of the hexameric model of pea PBGS. Several molecules with high docking scores were purchased and tested for whether they would inhibit pea PBGS; the best results were with the natural product rosmarinic acid.

The following concepts and definitions are provided in order to aid those skilled in the art in understanding the detailed description of the present invention.

The term "promoter" or "promoter region" refers to a nucleic acid sequence usually found upstream (5') to a coding sequence that controls expression of the coding sequence by controlling production of messenger RNA (mRNA) by providing the recognition site for RNA polymerase or other factors necessary for start of transcription at the correct site. As contemplated herein, a promoter or promoter region includes variations of promoters derived by means of ligation to various regulatory sequences, random or controlled mutagenesis, and addition or duplication of enhancer sequences. The promoter region disclosed herein, and biologically functional equivalents thereof, are responsible for driving the transcription of coding sequences under their control when introduced into a host as part of a suitable recombinant vector, as demonstrated by its ability to produce mRNA.

"Regeneration" refers to the process of growing a plant from a plant cell (e.g., plant protoplast or explant).

"Transformation" refers to a process of introducing an exogenous nucleic acid sequence (e.g., a vector, recombinant nucleic acid molecule) into a cell or protoplast in which that exogenous nucleic acid is incorporated into a chromosome or is capable of autonomous replication.

A "transformed cell" is a cell whose DNA has been altered by the introduction of an exogenous nucleic acid molecule into that cell.

The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression.

The phrase "DNA segment heterologous to the promoter region" means that the coding DNA segment does not exist in nature in the same gene with the promoter to which it is now attached.

The term "encoding DNA" refers to chromosomal DNA, plasmid DNA, cDNA, or synthetic DNA that encodes any of the enzymes discussed herein.

The term "genome" as it applies to bacteria encompasses both the chromosome and plasmids within a bacterial host cell. Encoding DNAs of the present invention introduced into bacterial host cells can therefore be either chromosomally integrated or plasmid-localized. The term "genome" as it applies to plant cells encompasses not only chromosomal DNA found within the nucleus, but organelle DNA found within subcellular components of the cell. DNAs of the present invention introduced into plant cells can therefore be either chromosomally integrated or organelle-localized.

The term "herbicide" refers to a chemical substance used to kill or suppress the growth of plants, plant cells, plant seeds, or plant tissues.

The term "inhibitor" refers to a chemical substance that inactivates the enzymatic activity of a protein such as a biosynthetic enzyme, receptor, signal transduction protein, structural gene product, or transport protein that is essential to the growth or survival of the organism. In the context of the instant invention, an inhibitor is a chemical substance that inactivates the enzymatic activity of porphobilinogen synthase. The term "herbicide" is used herein to define an inhibitor when applied to plants, plant cells, plant seeds, or plant tissues.

The terms "microbe" or "microorganism" refer to algae, bacteria, archae, fungi, and protozoa.

"Overexpression" refers to the expression of a polypeptide or protein encoded by a DNA introduced into a host cell, wherein said polypeptide or protein is either not normally present in the host cell, or wherein said polypeptide or protein is present in said host cell at a higher level than that normally expressed from the endogenous gene encoding said polypeptide or protein.

The term "plant" refers to any plant or part of a plant at any stage of development. Therein are also included cuttings, cell or tissue cultures and seeds. As used in conjunction with the present invention, the term "plant tissue" includes, but is not limited to, whole plants, plant cells, plant organs, plant seeds, protoplasts, callus, cell cultures, and any groups of plant cells organized into structural and/or functional units.

The term "plastid" refers to the class of plant cell organelles that includes amyloplasts, chloroplasts, chromoplasts, elaioplasts, eoplasts, etioplasts, leucoplasts, and proplastids. These organelles are self-replicating and contain what is commonly referred to as the "chloroplast genome," a circular DNA molecule that ranges in size from about 120 kb to about 217 kb, depending upon the plant species, and which usually contains an inverted repeat region.

The term "tolerance/resistance" refers to the ability to continue normal growth or function when exposed to an inhibitor or herbicide.

The term "transformation" refers to a process for introducing heterologous DNA into a cell, tissue, or plant. Transformed cells, tissues, or plants are understood to encompass not only the end product of a transformation process, but also transgenic progeny thereof.

The "oral composition" is a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral composition may be a single phase oral composition or may be a combination of two or more oral compositions.

The term "orally-acceptable carrier" as used herein means a suitable vehicle, which can be used to apply the present compositions to the oral cavity in a safe and effective manner. Such vehicle may include materials such as fluoride ion sources, additional anticalculus agents, buffers, other abrasive materials, peroxide sources, alkali metal bicarbonate salts, thickening materials, humectants, water, surfactants, titanium dioxide, flavor system, sweetening agents, xylitol, coloring agents, and mixtures thereof.

Morpheeins Concept:

The term "morpheeins" is used in this disclosure by the inventor to describe different quaternary isoforms of a protein, which are described in detail below. Morpheeins of a given protein are in equilibrium with each other, and in some cases morpheeins can form the basis for allosteric regulation. In the case of plant and some bacterial PBGS, the stimulus for transition between morpheeins is the allosteric regulator, i.e., an agent (e.g., magnesium).

One dogma of modern biochemistry is that the three dimensional structure of a protein is a direct consequence of the amino acid sequence of that protein. Consequently, it is taught that one protein sequence makes one native structure. The discovery of prions challenges the one structure concept, but not if one believes these to be "misfolded". The current invention draws on a new discovery, that of morpheeins, which are alternate protein quaternary structures that are a physiologically relevant consequence of a conformational change in the monomeric unit. In the case of morpheeins, the alternate native states are close in energy to each other, but each state dictates a different finite quaternary multiplicity, as illustrated schematically in FIG. 6.

The morpheeins of a given protein have partial differences in secondary and tertiary structure, and these differences dictate a difference in quaternary structure. In certain aspects, morpheeins are like prions; one protein sequence that can undergo a conformational change which results in an altered quaternary structure (aggregation state). However, in other aspects, morpheeins are unlike prions in that the oligomer is of finite multiplicity and the quaternary structure change is reversible, non-pathologic, and part of a normal physiologic control process.

In FIG. 6, the fundamental structural unit is monomeric and the association of any two units is driven by the placement of a dashed line adjacent to a thick line. This is the rule of assembly. FIG. 6 is a two dimensional illustration of the concept that the multiplicity of the assembly is directed by the shape of the fundamental structural unit (shown as a monomer) and the rule of assembly. In FIG. 6, there are four different shapes for the fundamental unit. The monomeric pac-man-like shape in the lower left cannot come together with itself in a way that places the dashed line adjacent to the thick line, this monomer cannot oligomerize. The half-oval monomer shape is capable of coming together with itself to form a dimer. Once the dimer is formed, all of the dashed lines are adjacent to all of the thick lines and oligomerization stops at the dimer. The pie-wedge shape can come together with itself in the same fashion, but three units are needed in order to have all the dashed lines adjacent to all the thick lines. Thus, the pie-wedge monomer is destined to multimerize into a trimer. Finally, following the same logic, the square monomer form is destined to form a tetrameric assembly.

Working within the morpheein concept, each multimer has different physiologically relevant functional characteristics, such as different $K_m$ and $V_{max}$ values. For instance, one multimer might be the allosteric "ON state" with high enzymatic activity and another multimer might be the allosteric "OFF state" with low activity. Alternatively, the function of the different oligomers might be a result of differences in the molecular surface of the oligomer. For instance, the rounded surface of the trimer in FIG. 6 would interact with different receptors or binding partners than the oval surface of the dimer or the pointed surface of the tetramer. These molecular surface differences could dictate the cellular localization for the complex. FIG. 8 is a two dimensional schematic of agents that can stabilize one or the other of the morpheein assemblies in FIG. 6.

Figure 24:
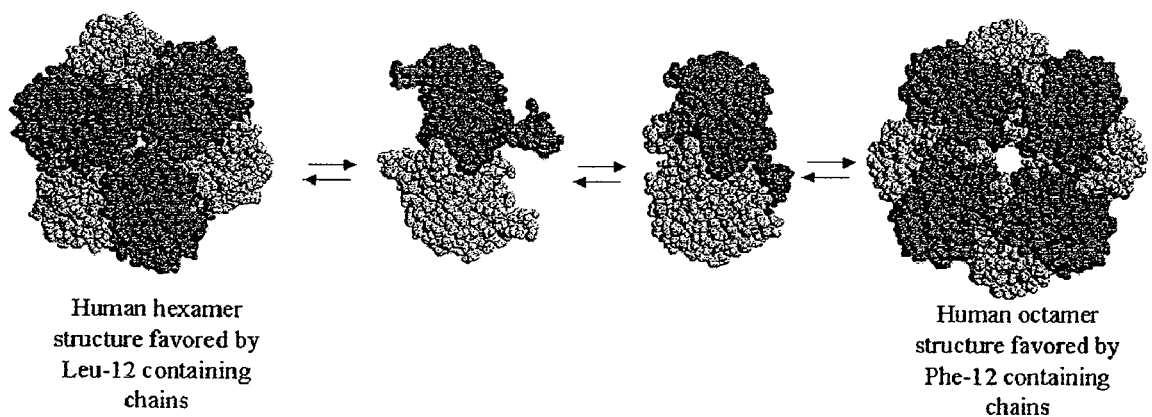
FIG. 24 shows the interconversion of human PBGS octamer and hexamer. The interconversion and disproportionation of human PBGS hexamer and octamer is proposed to proceed through a dissociation of the oligomers to their component dimers, interconversion of the dimeric forms, and a reassociation of the oligomers. The disproportionation reaction shown in FIGS. 25-27 prove this reaction occurs.

One example of morpheeins is the porphobilinogen synthase (PBGS) system where discovery of the alternate quaternary assemblies arose from characterization of the naturally occurring human PBGS variant F12L, which was found to have very different catalytic properties relative to the wild type (predominantly) octameric protein. The assembly of hexameric PBGS is illustrated in FIG. 9, and is dramatically different from the assembly of the PBGS octamer (FIG. 2). Fortunately, there is a vast phylogenetic variation in the amino acid sequence of the N-terminal arm segment of PBGS. This sequence variation provides a significant phylogenetic variation in the rate with which the alternate quaternary isoforms of PBGS will interchange. In human PBGS, particularly in the absence of turnover, the rate of interconversion of the quaternary isoforms is so slow as to be unmeasurable, thus providing us with the ability to observe stable crystal structures of the octameric and hexameric forms of the human protein. The discovery of the two forms of human PBGS is the first concrete example of morpheeins and is described in detail in EXAMPLE 1. EXAMPLE 1 describes the discovery of the hexameric structure for F12L, and its unique properties. EXAMPLE 2 describes experiments demonstrating that the quaternary structure, rather than the specific mutation is responsible for the unusual properties of F12L. EXAMPLE 3 describes experiments demonstrating that the octameric and hexameric morpheeins of human PBGS can exist in a dynamic equilibrium, thus proving that morpheein equilibria, such as are illustrated in FIG. 6 and FIG. 24, can exist.

The inventor's prior knowledge of the allosteric effect of magnesium binding on some PBGS and on the location of the allosteric magnesium binding site suggested that for some PBGS, the quaternary structure equilibrium between octameric and hexameric PBGS forms the structural basis for the phenomenon of allosterism. This lead to the formulation of the morpheein model for allosteric regulation (FIG. 7), which is fundamentally different from classic models for allosterism.

Allosterism is a general concept wherein the activity of an enzyme is affected by the binding of an allosteric regulator molecule to a binding site on the protein that is not the catalytic site. Most models of allosteric regulation propose that the active and the inactive state are oligomers of the same multiplicity, that these two forms are in equilibrium with each other, and that binding of an allosteric regulator molecule can shift this equilibrium (see FIG. 1). In some cases, this classic model is well supported or even proven by X-ray crystal structures of the ON and OFF states. In general however, there is insufficient structural information (three dimensional X-ray crystal structures for instance) in order to allow an understanding of where the allosteric regulator binds, how the ON and OFF states differ from each other, or why one form is more active than the other. The inventor's recent discovery of two different quaternary forms of PBGS allows one to examine these forms and to deduce a rational explanation for the allosteric regulation of the PBGS of some organisms by magnesium. Moreover, the observation of alternate quaternary forms of PBGS leads to a general description of the concept of morpheeins as a regulatory mechanism for protein function and the description of agents that can trap one or another of the morpheein forms such as to direct protein function. This is the morpheein model for allosteric regulation, as illustrated in FIG. 7. FIG. 10 illustrates this concept using, for example, the tetramer and trimer shown in FIG. 7, but adds a "splinter" to illustrate the allosteric regulator that can only bind to the tetramer. Binding of the splinter perturbs the quaternary structure equilibrium and draws the system toward the tetrameric form. FIG. 8 illustrates the concept of agents (shown as "wedges") that can trap a desired quaternary state of the protein and thus act to draw the equilibrium toward that state. Thus, these agents, which will perturb the quaternary structure equilibrium of morpheeins, can inhibit or activate the protein. In one embodiment of the invention, the agent is an inhibitor, which traps the inactive form and therefore prevents formation of the active form. In one embodiment, the protein is PBGS, the inactive form is a hexamer and the active form is an octamer. A non-limiting example of the inhibitor is a rosemarinic acid or a derivative thereof. In another embodiment of the invention, the agent is an activator, which traps the active form of the protein.

Accordingly, in this the invention, a general mechanism for allosteric regulation using morpheeins (quaternary structure isoforms) is proposed. In this mechanism, the monomeric structures are different in some aspect of their secondary/tertiary structure, and these differences dictate an assembly into one or the other morpheein. This morpheein utilizing allosteric mechanism is illustrated schematically in FIG. 7.

FIG. 10 is a two dimensional representation of the equilibrium between two forms of a protein (morpheeins). A unit (e.g., a monomer) of one form (shown herein as a square) contains four different surfaces, which are a line, a thick line, a dashed line, and a squiggly line. The complementary surfaces that naturally associate are illustrated herein as the thick line with the dashed line. This association defines the rule of engagement between the units. When the subunit association potential of the square is satisfied (in another words when all thick lines are associated with all dashed lines), the optimal resulting assembly is a tetramer. Thus, the oligomeric assembly is dictated by the structure of the monomer and the rule of engagement. As shown in FIG. 10, the square structure can associate with a "splinter", which is a schematic representation of an agent (e.g., an allosteric regulator molecule); association of the square monomer and the square tetramer with the splinter affect a function of the multimeric protein, for example, in the case of plant and some bacterial PBGS, magnesium provides stability to these forms of the protein.

The square unit is in equilibrium with another structure, which shares some, but not all of its secondary and tertiary structure and consequently shares only some of the surface characteristics. The alternate unit is illustrated in FIG. 10 as a "segment". This monomer contains the surfaces depicted by the thick line and the dashed line; the rule of engagement between these surfaces is the same as for the square unit. Consequently, following this rule of engagement, the alternate unit assembles into a trimer. It is important that the trimeric structure and its individual components do not contain the binding site for the allosteric regulator molecule (the splinter). Since the splinter stabilizes the square and its oligomer, the presence of the splinter will pull the equilibrium of quaternary structures toward the square and its oligomers.

The observation of hexameric PBGS provided the first example of how quaternary structure can serve as a structural basis for allosteric regulation of protein function. In PBGS from photosynthetic organisms and some bacteria, a protein concentration dependence of the specific activity provides evidence for an equilibration between a fully active (presumably octameric) form and an inactive (presumably hexameric) form (See FIGS. 5, 20A and 20B).

FIG. 10 is a schematic description of the behavior of PBGS, which is better illustrated using space filling diagrams in FIG. 11. In the case of PBGS, the square in FIG. 10 is the hugging dimer and the segment in FIG. 10 is the detached dimer. In each case, the structures share some, but not all surface characteristics and the rule of engagement between surfaces is to a first approximation shared between the two alternate structures. In the case of PBGS, the differences in oligomeric structure translate to different functional characteristics, such as the pH rate profiles illustrated in FIG. 12 and the $K_m$ and $V_{max}$ values illustrated in Table 1. It is reasonable to assume that different quaternary structures of other proteins also translate to different functional characteristics. It is well known that dimerization of receptors is associated with signal transduction. What has not been appreciated prior to this invention is that the structures of the monomer within the dimer structure may not be the same as the structures of the monomer when they are not in the dimer structure.

Figure 13:
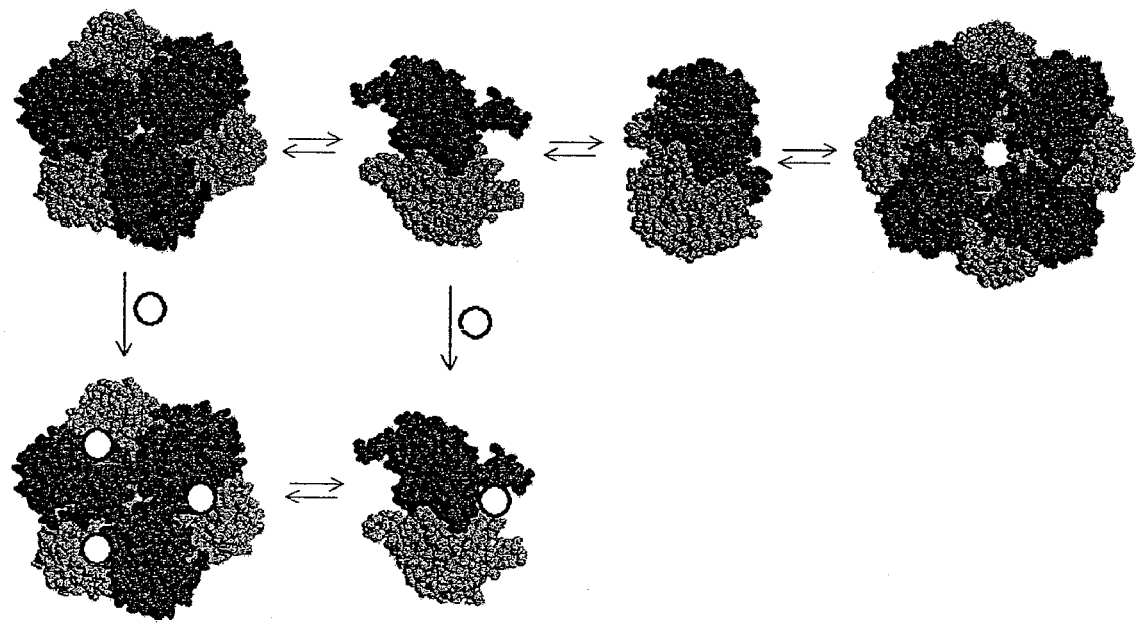
FIG. 13 shows a schematic representation of an embodiment of the inventive inhibition process, wherein an inhibitor of the invention (represented by circles) binds to one or more domains of the dimeric or hexameric PBGS to inhibit the formation of the octamer, stabilize bound forms and shift equilibrium. In this case, the inhibitor is a circle that binds to the arm-pit of the hugging dimer/hexamer forms.

FIG. 11 illustrates how Mg serves as an allosteric activator of PBGS from some species, FIG. 13 illustrates an agent that would serve as an inhibitor of PBGS through stabilization of the less active hexameric form. This schematic agent, illustrated as a ball that would fit into the arm-pit of the detached dimer, is an illustration of an agent of this invention.

Another non-limiting example of a protein which contains morpheeins is a Class Ia ribonucleotide reductase. The recent model put forth for allosteric regulation of Class Ia ribonucleotide reductase describes an equilibrium between a tetramer and a hexamer [44]. In this case, the model is schematic only and authors do not have protein structures that define the differences in the putative morpheeins. However, ribonucleotide reductase is essential for de novo DNA biosynthesis, the Class Ia enzymes are found in all eucaryotes, and inhibition of de novo DNA biosynthesis is a rational approach to cancer chemotherapy. Thus, affecting a function of Class Ia ribonucleotide reductases (e.g., the inhibition) can be achieved through selective binding of an effector to a surface that is unique to the less active morpheein.

Although PBGS is the first example for which crystal structures are available for both of the two alternate quaternary forms, there are other systems described in the literature for which the morpheein concept appears to be applicable. As metastable states, it is not surprising that morpheeins have not previously been seen as alternate crystal structures of the same protein. Clues to the existence of morpheeins in homo-oligomeric enzymes come from kinetic phenomena such as a protein concentration dependence to an enzyme's specific activity, from non-Michaelis behavior that fits to a double hyperbolic equation, from kinetic hysteresis, from dependence of activity upon the order of addition of reaction components, or from various protein sizing methods that suggest more than one quaternary isoform. None of these characteristics is in itself diagnostic of a morpheein equilibrium.

Figure 28:
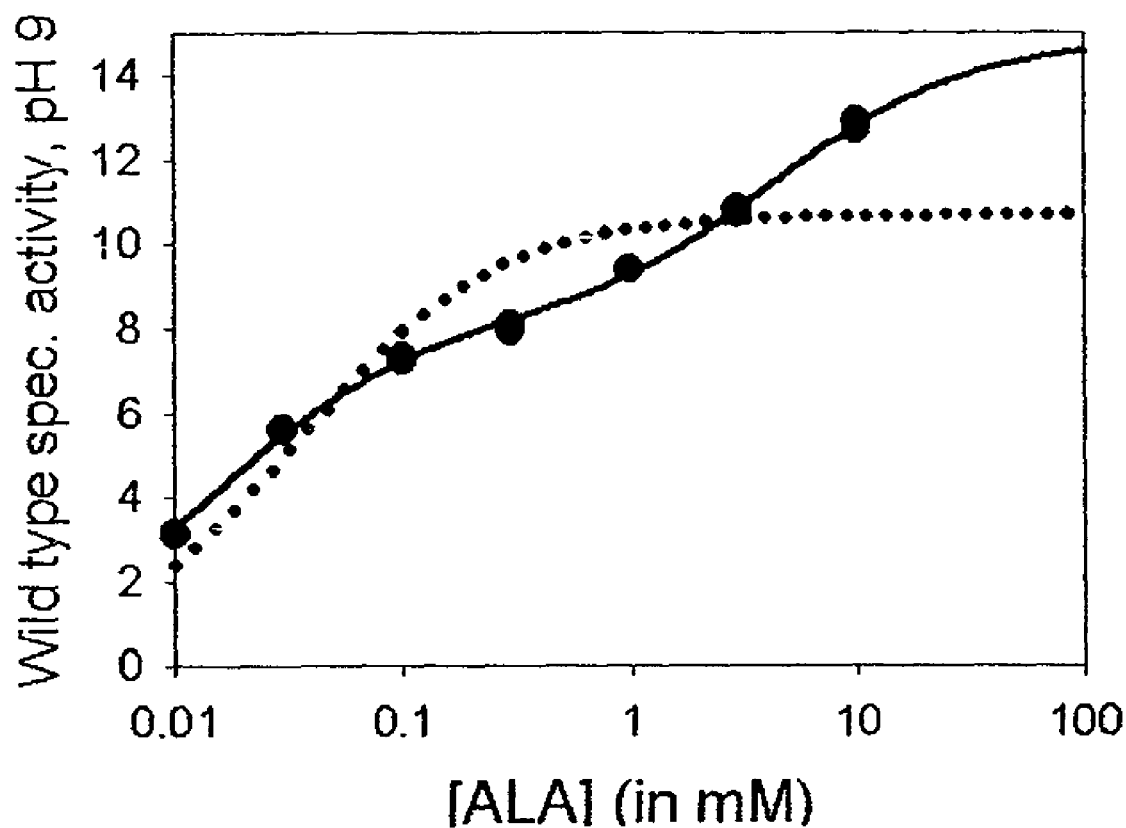
FIG. 28 illustrates the dependence of wild type human PBGS activity on the concentration of the substrate ALA at pH 9. The dotted line is the fit to the single hyperbolic Michaelis Menton equation. The solid line is the fit to a double hyperbolic equation, indicative of catalysis by two morpheeins, one with a low $K_m$ value and one with a high $K_m$ value.

The multimetic protein of the invention should have at least one characteristic such as a protein concentration dependent specific activity or an ability to separate into different assemblies by e.g., ion-exchange chromatography, native gel electrophoresis; analytical ultracentrifugation, size-exclusion chromatography (on the basis of size); To demonstrate the equilibrium, kinetic studies can be conducted to show, e.g., $K_m$ and $V_{max}$; activity as a function of substrate concentration fit to MM equation; morpheeins will not fit well to a hyperbolic curve but rather a double hyperbolic curve, as seen for wild type human PBGS at pH 9 as illustrated in FIG. 28. Non-limiting example of a function of the multimeric protein is an enzymatic activity and an ability to interact with other molecules such as, for example, an ability to bind a different protein. The function can be inhibited or enhanced (or activated). Monitoring of changes in the function can be conducted by, for example, monitoring kinetic parameters $K_m$ and V, as a skilled artesian would appreciate. In certain embodiments of the invention, inhibition of a protein function is through stabilization of a less active morpheein.

In certain embodiments, the agent is adapted to affect a function of the multimeric protein. Non-limiting examples of the function of the multimeric protein is an activity and wherein affecting is at least one of inhibiting or activating. In certain embodiments, the agent is associated with the quaternary isoform having a lesser activity. In certain embodiments, the agent is bound to the quaternary isoform having a greater activity. A non-limiting example of an agent inhibiting octameric PBGS is described further below.

The octameric form of PBGS binds to substrate in a physiologically relevant concentration range and is active at physiological pH. The octamer is composed of four hugging dimers, where the arms of one subunit hug the barrel of an adjacent subunit with which there are strong barrel-to-barrel interactions (see FIG. 2).

TABLE 1

Kinetic parameters at pH 7 and pH 9 for wild type human PBGS as an example of an octameric PBGS and the human PBGS variant F12L as an example of the hexameric PBGS morpheein

|  | pH | $K_{m1}$ | $V_{max1}$ | $K_{m2}$ | $V_{max2}$ |
| --- | --- | --- | --- | --- | --- |
| F12L | 7 | 17.7 ± 1.1 | 1.14 ± 0.05 |  |  |
| hexamer | 9 | 4.6 ± 0.1 | 18.2 ± 0.02 |  |  |
| wild type | 7 | 0.25 ± 0.01 | 55.5 ± 0.2 |  |  |
| octamer | 9 | 0.015 ± 0.001 | 8.16 ± 0.13 | 4.46 ± 0.80[a] | 6.67 ± 0.36[a] |

[a]At pH 9 the wild type human PBGS shows some propensity to form the hexamer (see below and FIG. 28).

The newly discovered hexameric form of PBGS is proposed to be an essential component of the regulation of tetrapyrrole biosynthesis in a subset of organisms, including plants and some pathogenic bacteria, but not including humans, animals or fungi. The hexameric form is substantially inactive under physiological conditions. In particular, the hexamer cannot bind substrate in the physiologically relevant concentration range because its $K_m$ value is at least two orders of magnitude larger than the $K_m$ of the octamer. The hexamer is composed of three detached dimers, where the N-terminal arms do not interact with the adjacent subunit with which there are strong barrel-to-barrel contacts (see FIG. 9).

The transition between the hexameric form and the octameric form involves a significant change in the protein structure, which is a dramatic reorientation of the N-terminal arm relative to the α8β8-barrell. Certain embodiments of the invention relate to the inhibition of the structural change from a hexamer to an octamer (as illustrated in FIG. 13) to inhibit the activation of PBGS and tetrapyrrole biosynthesis in plants and/or bacteria. Since the inhibition mechanism is effective for plants and bacteria, but not animals, the invention provides a novel approach to bacteriostatic, antibiotic and herbicide applications.

Thus, in certain embodiments, the invention comprises an inhibitor of the hexamer-to-octamer transition for those PBGS that are physiologically regulated by magnesium. The inhibitor can be a known or novel compound. The inhibitor is effective at inhibiting tetrapyrrole biosynthesis in plants and bacterial pathogens at that point in their growth and development where the hexamer-to-octamer transition is physiologically significant. Inhibition of the quaternary structure transition from hexameric PBGS to octameric PBGS is a novel target for the development of antibiotics and herbicides.

Determining which PBGS Proteins are Targets:

There is a phylogenetic variation in PBGS proteins where some have an allosteric magnesium and others do not. The PBGS that have the allosteric magnesium are comprised of the archaea, all the bacteria with the exception of the genus *Rhodobacter*, and all of the photosynthetic eucarya (e.g., green plants) [11] (FIGS. 4 and 14). Another more recent exception appears to be the malaria parasite *Plasmodium falciparum* [45]. Based on the inventor's previously determined crystal structure for *E. coli* PBGS and the structure of hexameric PBGS disclosed herein, it appears that the role of the allosteric magnesium is to induce a structural change between the low activity hexamer and the high activity octamer (see FIGS. 11 and 20C). The hexamer-octamer transition for Mg acting on PBGS is a novel structural paradigm for allosteric regulation of protein function.

An inhibitor that stabilizes a hexamer will be most effective against a subset of PBGS that contain the allosteric magnesium but do not contain the active site zinc (i.e., PBGS within QSE, see FIG. 4). These are the photosynthetic eucaryotes and a subset of bacteria, including pathogens such as *Pseudomonas aeruginosa*. These PBGS proteins elicit the property of protein concentration dependent specific activity, which indicates an interconversion between large active quaternary forms and smaller less active quaternary forms (see FIG. 5, 20A and 20B). Also seen for NE quadrant, where the active form for at least one species is a hexamer [15].

Figure 15A:
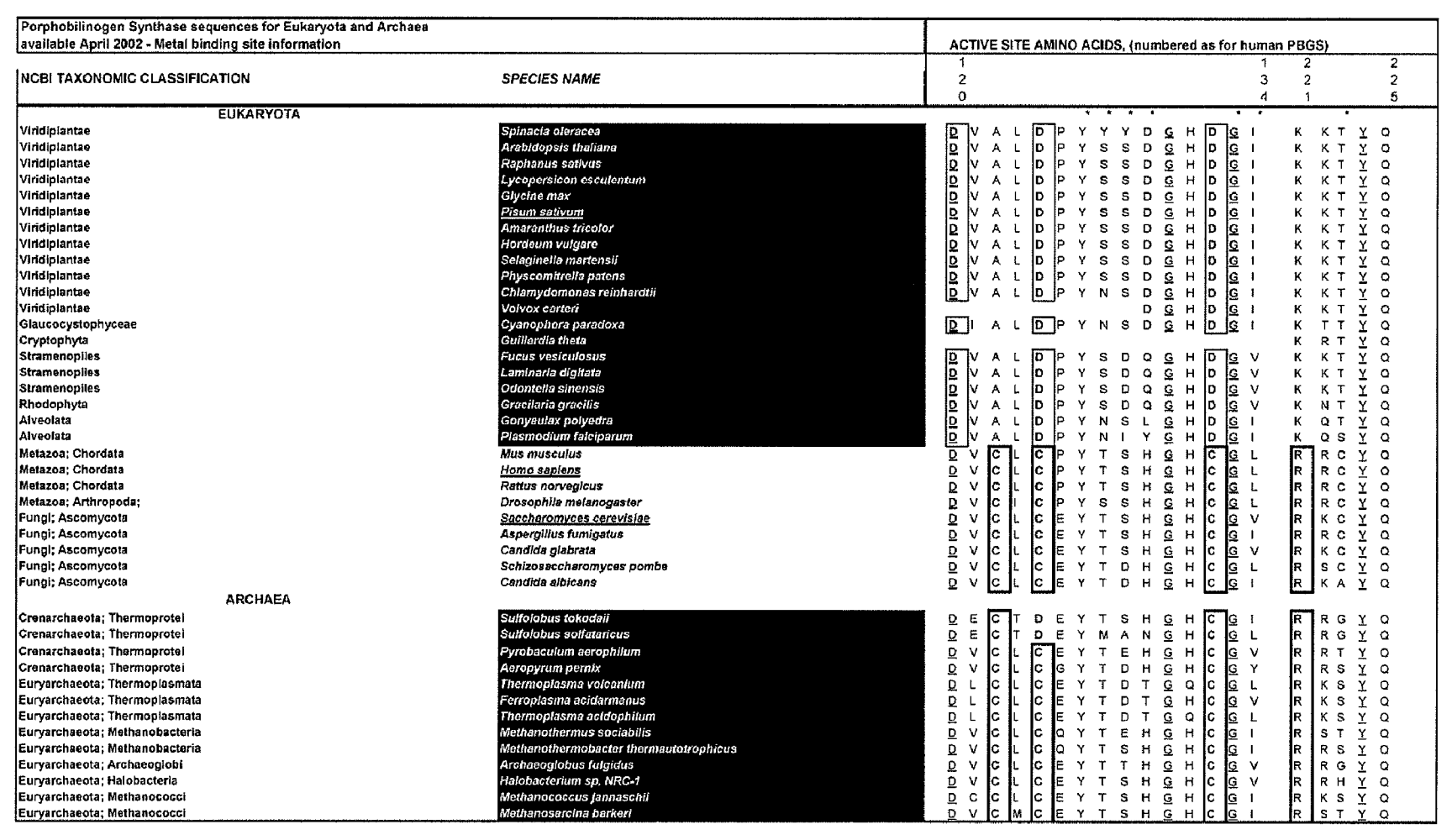
Figure 15B:
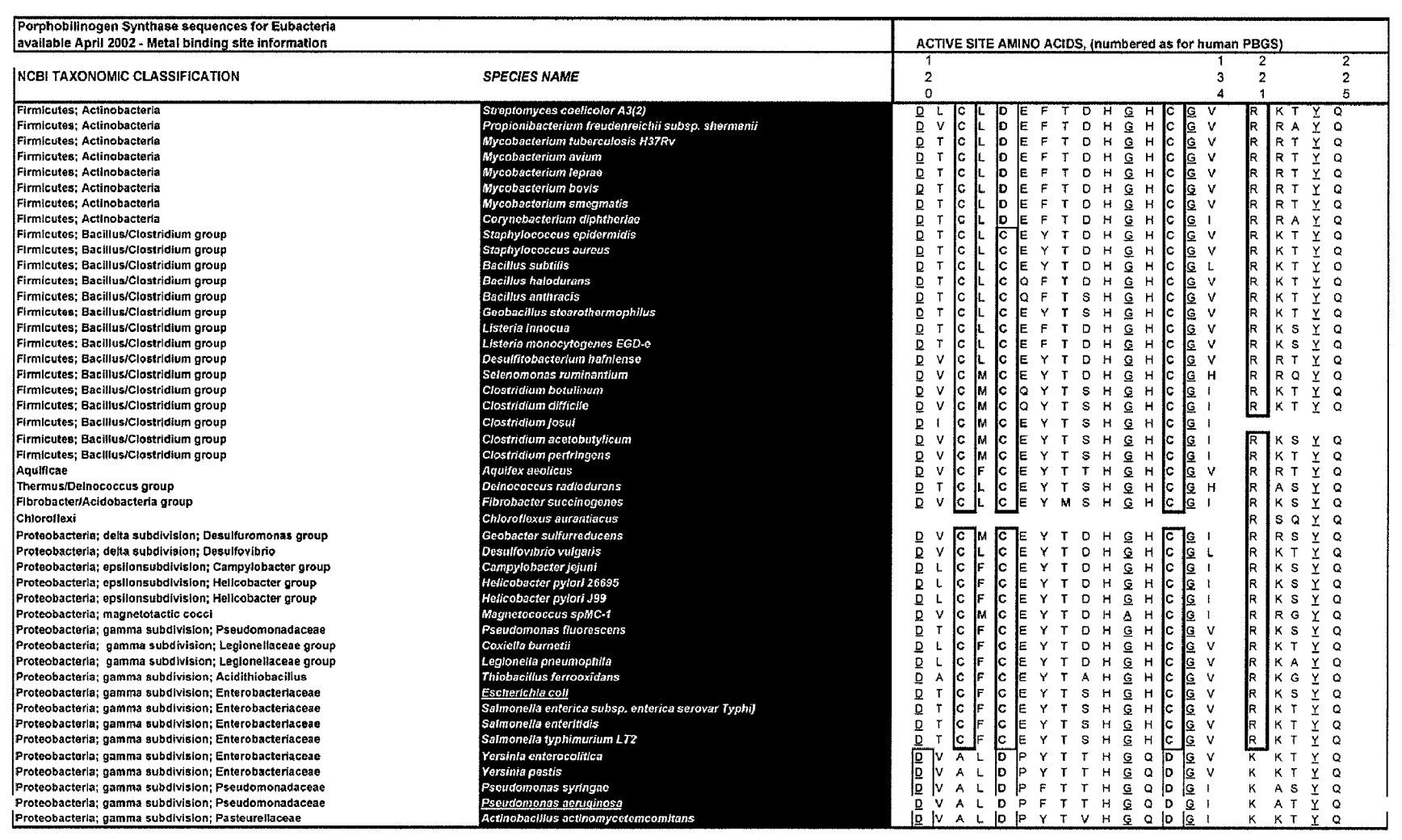
Figure 15C:
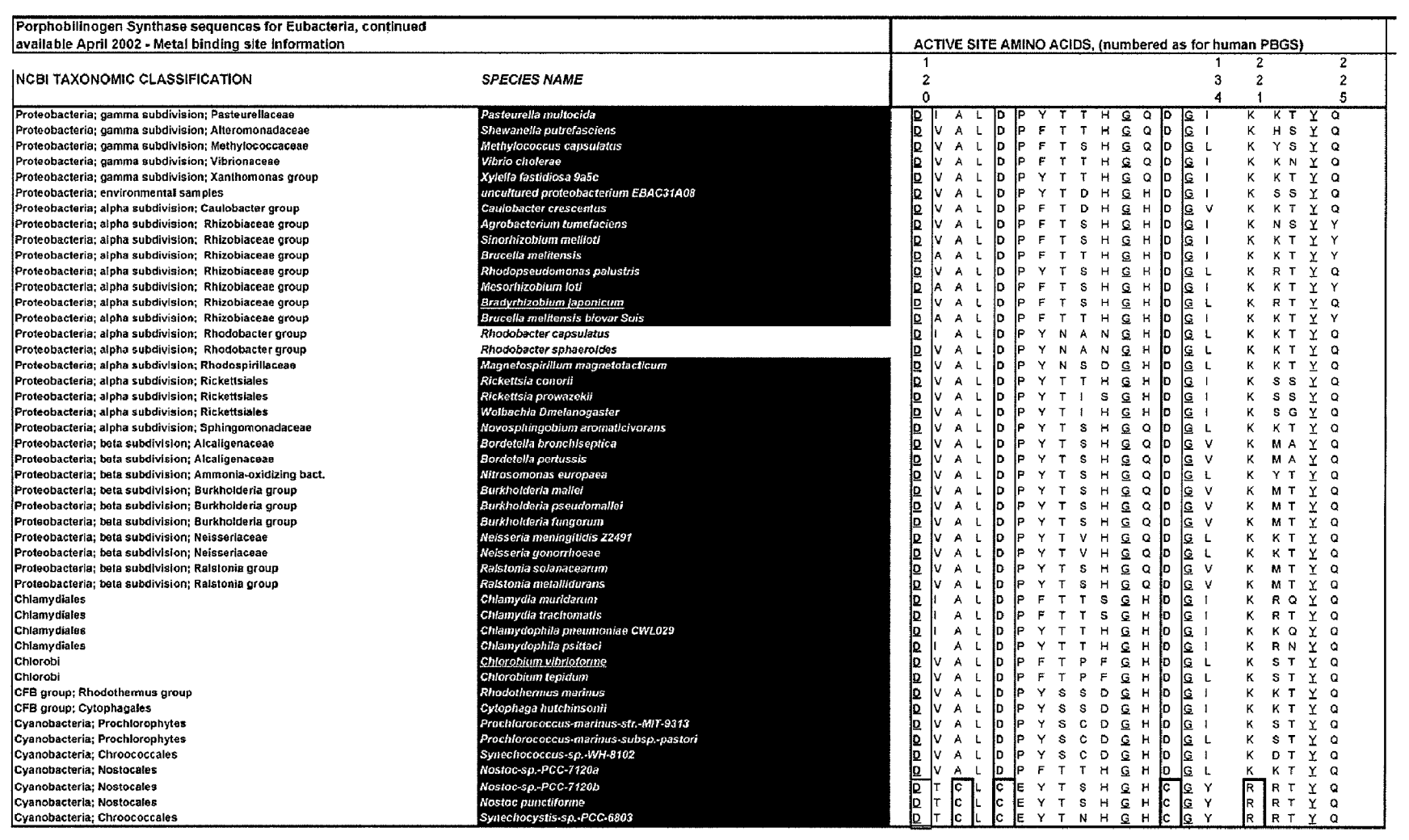

Thus, in certain preferred embodiments, the inhibitor of the invention is effective to inhibit the formation of octameric PBGS derived from bacteria, archaea, or eucarya, provided that the octameric PBGS contains an allosteric magnesium binding site. A non-limiting list of sources of the octameric PBGS, which can be inhibited by the composition of the invention, is shown in FIG. 14, which is a classification of organisms including bacteria, archaea and eucarya. FIGS. 15A and 15B and 15C represent an alignment of active site metal binding residues for the PBGS sequences obtained from GenBank and other web-searchable genomes available as of April 2002. The assignment of an organism into one of the four quadrants of FIG. 4 is based on the sequence information presented in FIGS. 15A-C. The presence of the active site zinc binding site is indicated by a cysteine rich cluster (positions 122, 124, and 132 of human PBGS) in association with an arginine residue on the active site lid (position 221 of human PBGS). Species that do not have the cysteine rich active site zinc binding cluster, contain instead an aspartic acid rich region and the active site lid residue is a lysine.

In certain embodiments of the invention, the inhibitor replaces a metal ion and thereby binds at a metal ion binding site, preferably, the metal ion is zinc or magnesium. In certain embodiments of the invention, the inhibitor binds at an active site. The inhibitor can bind anywhere, but the binding site must stabilize one quaternary structure. Binding is preferable to a site that is present in one morpheein but not the other.

Inhibitors of the invention can be identified using the following protocol. First, a model is provided for a hexameric form of a PBGS that contains the allosteric magnesium but does not contain the active site zinc. Example 4 describes the method used to build a model for a hexamer of *Pseudomonas aeruginosa* PBGS, which can serve as a template for more routine building of other hexameric PBGS proteins such as *Rhodobacter capsulatus* [15]. The initial model can, e.g., be one of pea PBGS. Second, small molecule databases are screened in silico for molecules that will fit into a hug-disabling domain adjacent to the N-terminal portion of the subunit. Some small molecule databases are available online [46] and others are being built in-house at Fox Chase Cancer Center. The hug-disabling domain is at least one area of the detached dimer on which binding of the inhibitor inhibits the arms of the dimer from hugging the barrel of that dimer which is necessary to form the active octamer. See FIG. 13, wherein circles represent inhibitors. A likely site of a hug-disabling domain is underneath the joint at which a hugging arm joins the body of the subunit (i.e., at the "arm-pit"). Theoretically suitable molecules will be empirically tested in vitro by determining their effect on the protein concentration dependent specific activity of pea PBGS, which is available using an artificial gene construct. Those molecules that inhibit the specific activity of the protein in a protein concentration dependent fashion are good inhibitor candidates (see FIG. 5).

Inhibitors of the invention can be identified for other morpheein targets using a similar in silico screening approach provided that a crystal structure or model structure can be prepared for the inactive quaternary isoforms of the target protein.

The following method will allow identifying inhibitors that will bind anywhere, not necessarily in the hug-disabling domain on PBGS to inhibit octamer formation. A functional assay for specific activity of PBGS will be used first to select potential inhibitors from available molecules that are identified in the computational screen, e.g., substances that are not harmful to humans. After potential inhibitors are selected, they will be further screened for affecting specific activity based on protein concentration. This traditional screening for inhibitors does not have any special propensity to select inhibitors that bind in a morpheein specific fashion.

Accordingly, this invention provides a method of affecting a multimeric protein, the method comprising: providing said multimeric protein comprising an assembly having a plurality of units, wherein each of said units comprises a first complementary surface and a second complementary surface and wherein the first complementary surface of one unit is associated with the second complementary surface of another unit, provided that the assembly is at least one of different quaternary isoforms on a condition that (1) a structure of said units determines a structure of said different quaternary isoforms, (2) said units are in an equilibrium and (3) the structure of said different quaternary isoforms influences a function of said multimeric protein; providing the composition of the invention comprising the agent, wherein the agent is adapted to affect the equilibrium by binding to a binding site on the assembly; and contacting the assembly with the agent, wherein the agent affects the equilibrium by binding to the binding site and thereby affecting said multimeric protein. In certain embodiments of the method, affecting said multimeric protein comprises affecting a formation of a quaternary isoform. In certain embodiments of the method, affecting said multimeric protein comprises affecting a function of said multimeric protein.

Further provided is a method of inhibiting a multimeric porphobilinogen synthase from forming an active form, the method comprising: applying the composition of the invention to the multimeric porphobilinogen synthase; associating the composition with the less active form; inhibiting the less active form from assembling into the active form and thereby inhibiting the multimeric porphobilinogen synthase from forming the active form. A non-limiting example of the inhibitor is a rosmarinic acid or derivatives thereof, whose characterization as an inhibitor of pea PBGS is described in EXAMPLE 5.

A preferred application of the inventive composition is for inhibiting or preventing development or growth of bacteria, archaea, and/or eucarya in a human or an animal host. Other applications of the composition of the invention include prevention or inhibition of biofilms on various surfaces including teeth, pipes, tubing, ships, or generally any surfaces immersed in water/air mixtures wherein bacteria causing damage can be found. Thus, for example, the compositions of the invention can be effective to prevent or inhibit growth of barnacles on a surface of a ship.

Depending on the targeted organism, a composition of the invention can be used to prevent or inhibit damage caused by certain species. All plants are in QSE (see FIG. 4), as well as many protists. Examples of bacteria in QSE are in the Table 2, so these organisms are primary targets for applying the composition of the invention. Using Table 2 as a guide, various applications of the composition of the invention can be envisioned such as, for example, a drug, a toothpaste, a soap, a disinfectant, an anti-biofilm composition and, with application to plants, a herbicide.

TABLE 2

Bacteria with PBGS in the SE quadrant

| Species name | Potential Damage |
| --- | --- |
| Yersinia enterocolitica | Food borne gastroenteritis |
| Yersinia pestis | Plague |
| Pseudomonas syringae | Plant pathogen (tomatoes) |
| Pseudomonas aeruginosa | Opportunistic human pathogen of compromised tissues. Notorious for antibiotic resistance |
| Actinobacillus actinomycetemcomitans | Periodontal disease |
| Pasturella multocida | Infective agent in animal bite wounds |
| Shewenella putrefasciens | Oil pipeline corrosion, fish spoilage |
| Methylococcus capsulatus | Uses methane as carbon source |
| Vibrio cholerae | Cholera - severe diarrhea |

TABLE 2-continued

Bacteria with PBGS in the SE quadrant

| Species name | Potential Damage |
| --- | --- |
| Xylella fastidiosa | Pierces disease in plants (e.g. grapes) |
| Caulobacter crescentus | Asymmetric cell division |
| Agrobacterium tumefaciens | Crown gall on rose and others like apple, pear, peach, cherry, etc. |
| Sinorhizobium meliloti | Nitrogen fixing bacteria for alfalfa |
| Brucella melitensis | Bacterial disease of domestic animals (sheep, goats). Malta fever in humans. |
| Rhodopseudomonas palustris | Purple non-sulfur phototropic bacterium. |
| Mesorhizobium loti | Biotech subject |
| Bradyrhizobium japonicum | Nitrogen fixation soybeans. |
| Brucella melitensis biovarsvis | Brucellosis - zoonotic disease |
| Magnetospirillum magnetotacticum | Forms magnetite |
| Rickettsia conorii | Mediterranean spotted fever |
| Rickettsia prowazekii | Epidemic typhus |
| Novosphingobium aromaticivorans | Food industry |
| Bordetella bromchseptica | Common in cats |
| Bordetella pertussis | Whooping cough |
| Nitrosomonas europaea | Auxotropic nitrifying bacteria |
| Burkholderia mallei | Glanders (horses); potential bioterrorism agent |
| Burkholderia pseudomallei | Melioidosis, Whitmore's disease, endemic in tropical climates |
| Burkholderia fungorum | "Group", human and plant pathogens and environmentally important bacteria |
| Neisseria meningitides | Bacterial meningitis |
| Neisseria gonorrhoeae | Gonorrhea |
| Ralstonia solanaccarum | Plant disease, "Southern wilt" |
| Ralstonia metallidurans | Heavy metal resistant |
| Chlamydia muridarum | Chlamydia - STD |
| Chlamydia trachomatis | Chlamydia - STD |
| Chlamydophila pneumoniae | 10% of pneumonia |
| Chlamydophila psittaci | Psittacosis (parrot fever) |
| Chlorobium vibrioforme | Green sulfur bacterium |
| Clorobium tepidum | Green sulfur bacterium |
| Rhodothermus marinus | Hermophillic halophillic bacterium |
| Cytophaga hutchinsonii | Digests crystalline cellulose |
| Shewanella oneidensis | Can turn soluble metals insoluble. Bioremediation |
| Vibrio vulnificus | Warm seawater infects open wounds |
| Vibrio parahaemolyticus | Warm seawater infects open wounds; diarrhea |
| Xanthomonas campestris | Plant pathogen |
| Xanthomonas axonopodis | Plant pathogen |
| Pirellula | Plant pathogen |
| Brown algae Fucus vesiculosus | Bladder wrack |

Advantageously, the composition of the present invention is effective to cure or prevent a disease caused by bacteria, archaea, and/or eucarya. The composition is effective to prevent formation of the multimeric PBGS (e.g., octameric PBGS or another active form having a lesser number of monomers) and thereby inhibit or prevent development or growth of bacteria, archaea, and/or eucarya. In certain embodiments, the multimeric PBGS contains an allosteric magnesium binding site. In one variant of this embodiment, the composition is effective to cure or prevent a disease caused by contacting bacteria, archaea, and/or eucarya. In yet another variant of this embodiment, the composition is at least one of a drug, a toothpaste, a soap, a disinfectant, an anti-biofilm composition, and a herbicide.

In certain embodiments, the composition does not contain the allosteric magnesium binding site and the catalytic zinc binding site. In one variant of this embodiment, the composition is effective to cure or prevent a disease caused by contacting bacteria, archaea, and/or eucarya. In yet another variant of this embodiment, the composition is at least one of a drug, a toothpaste, a soap, and a disinfectant.

Antibiotics, herbicides, and fungicides are often based on the inhibition of an essential pathway that is specific to the bacteria, plant, or fungus and that is not present in humans/animals. For example, 1) the penicillin class of antibiotics is directed against bacterial cell wall biosynthesis, and animal cells do not have cell walls, or 2) the herbicide glyphosate is directed against aromatic amino acid biosynthesis, and humans do not have this pathway, we must eat aromatic amino acids. As more is learned about the differences in sequence and structure for various proteins/enzymes, it becomes possible to target an essential pathway that is universally present in animals, plants, bacteria, and fungi. Such is the case for targeting the tetrapyrrole biosynthetic pathway through the inhibition of PBGS as the foundation for antimicrobials or herbicides. The phylogenetic variation in metal binding sites among the PBGS of various organisms provides sufficient structural differences for development of an inhibitory agent that will not be inhibitory toward human PBGS. In the case of PBGS, there are significant differences between organisms in the inherent ability of the PBGS to equilibrate between morpheein forms and in the amino acid sequence of the morpheein surfaces. In the case of the more general inhibition of protein function through the selective stabilization of one morpheein form, it may be the case that the target is a pathway that is not present in humans or it may be the case that the target simply has sufficient phylogenetic variation outside the active site that the surfaces of the morpheeins are very different. For instance, sequence conservation in proteins is highest in the region of shared function, as in an enzyme active site. Sequence conservation is not high in regions that are not involved in shared function. One can argue that protein surfaces are the most susceptible to evolutionary changes and the least likely to be conserved between an organism (e.g. human) and it pathogen.

In certain embodiments, the composition comprises a pharmaceutically-acceptable medium in addition to the agent. The expression "pharmaceutically-acceptable medium" denotes a medium, such as, for example, a solvent, that is able to deliver the inhibitor, as well as any other active agents in the composition, to the target organism in a relatively safe and effective manner. The medium itself need not have any pharmaceutical activity.

As used herein, "pharmaceutically-acceptable medium" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the inhibitor of the present invention, its use in therapeutic compositions is contemplated. Supplementary or additional active ingredients also can be incorporated into the compositions.

Solutions of the active ingredients as free base or pharmacologically acceptable salts can be prepared in water suitably mixed with a surfactant, such as, for example, hydroxypropylcellulose. Dispersions also can be prepared in glycerol, liquid polyethylene glycols, mixtures thereof and in oils. Under ordinary conditions of storage and use, these preparations contain a preservative to prevent growth of all microorganisms.

The compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The composition of the present invention is advantageously administered in the form of injectable compositions either as liquid solutions or suspensions; solid forms suitable for solution in, or suspension in liquid prior to injection also may be prepared. These preparations also may be emulsified. A typical composition for such purposes comprises a 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters, such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components in the pharmaceutical are adjusted according to well know parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

An effective amount of the therapeutic agent is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual.

Another application of the inventive composition is a herbicide, wherein the composition additionally comprises a herbicidally-effective medium. The expression "herbicidally-effective medium" denotes a medium, such as a solvent, that is able to deliver the inhibitor, as well as any other active agents in the composition, to the target organism. The medium itself need not have any herbicidal activity.

Guidance for applying antibacterial compositions on crops is provided as follows: since all photosynthetic eukaryotes fall in the QSE quadrant of FIG. 4, they are themselves targets for the inhibitors proposed in this invention. However, the arm-pit inhibitor binding site shown in FIG. 13 has significant phylogenetic variation between plants and bacteria. Hence, agents that would act as an antibacterial spray on crops would be those capable of binding to this site in the bacterial PBGS, but not in the plant PBGS.

Compositions of the present invention include both dilute compositions, which are ready for immediate use, and concentrated compositions, which require to be diluted before use, usually with water.

The solid compositions may be in the form of granules, or dusting powders wherein the active ingredient is mixed with a finely divided solid diluent, e.g. kaolin, bentonite, kieselguhr, dolomite, calcium carbonate, talc, powdered magnesia, Fuller's earth or gypsum or a combination thereof. They may also be in the form of dispersible powders or grains, comprising a wetting agent to facilitate the dispersion of the powder or grains in liquid. Solid compositions in the form of a powder may be applied as dusts.

Liquid compositions may comprise a solution, suspension, or dispersion of the active ingredients in water optionally containing a surface-active agent, or may comprise a solution or dispersion of the active ingredient in a water-immiscible organic solvent, which is dispersed as droplets in water. The herbicidal composition is suitable either for tank mixing to produce a dilute composition ready for immediate use or for the formation of a concentrate.

The solutions or dispersions may be prepared by dissolving the active ingredients in water or an organic solvent optionally containing wetting or dispersing agent(s) and then, when organic solvents are used, adding the mixture so obtained to water optionally containing wetting or dispersing agent(s). Suitable organic solvents include, for example, ethylene dichloride, isopropyl alcohol, propylene glycol, diacetone alcohol, toluene, kerosene, methylnaphthalene, xylene or trichloroethylene, or a combination thereof.

Other additives and adjuvants may also be present in compositions of the present invention. Examples include antifreeze agents such as ethylene glycol and propylene glycol; dyes; dispersants; theological agents; anti-foam agents such as silicone based agents; and humectants such as ethylene glycol.

Development of herbicide on this basis allows developing herbicide resistant crops by making these resistant crops transgenic (i.e., containing genetic material artificially transferred from another species) for a PBGS that is the top half of the four quadrants of FIG. 4, e.g., human PBGS.

Herbicide Resistant Plant

Further provided is a herbicide resistant plant adapted to be transgenic for a multimeric porphobilinogen synthase that substantially exist in a multimeric form of a hugging dimer. In certain embodiments, the multimeric porphobilinogen synthase is derived from a human. In certain embodiments, the multimeric porphobilinogen synthase contains no allosteric magnesium binding site. The following provides guidance to making the herbicide resistant plant adapted to be transgenic for a multimeric porphobilinogen synthase.

The expression in a plant of a gene that exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region, which adds polyadenylate nucleotides to the 3' end of the RNA. Transcription of DNA into mRNA is regulated by a region of DNA usually referred to as the promoter. The promoter region contains a sequence of bases that signals RNA polymerase to associate with the DNA and to initiate the transcription of mRNA using one of the DNA strands as a template to make a corresponding complimentary strand of mRNA. This mRNA is then used as a template for the production of the protein encoded therein by the cells protein biosynthetic machinery.

In the instant invention, the promoter chosen will have the desired tissue and developmental specificity. Therefore, promoter function should be optimized by selecting a promoter with the desired tissue expression capabilities and approximate promoter strength and selecting a transformant that produces the desired PBGS activity. This selection approach from the pool of transformants is routinely employed in expression of heterologous structural genes in plants because there is variation between transformants containing the same heterologous gene due to the site of gene insertion within the plant genome (commonly referred to as "positional effect"). In addition to promoters that are known to cause transcription (constitutively or tissue-specific) of DNA in plant cells, other promoters may be identified for use in the current invention by screening a plant cDNA library for genes that are selectively or preferably expressed during the time of interest and then isolating the promoter regions by methods known in the art.

In a preferred embodiment of the invention, the PBGS transgene is to be expressed in the chloroplast in response to light. More specifically, the PBGS transgene is transcribed into mRNA in the nucleus and the mRNA is translated into a precursor polypeptide (Chloroplast Transport Peptide (CTP)/PBGS) in the cytoplasm. The precursor polypeptide is then transported (imported) into the chloroplast. Several chloroplast light inducible promoters that are active in plant cells have been described in the literature. Examples of such promoters include the light-inducible promoter from the small subunit of ribulose-1,5-bisphosphate carboxylase (ss-RUBISCO), a very abundant plant polypeptide, the chlorophyll a/b binding protein gene promoters and the phytochrome promoter which has been utilized recently in a light-switchable promoter system [47]. Some of these promoters have been used to create various types of DNA constructs that have been expressed in plants; see, e.g., PCT publication WO 84/02913.

Other promoters that are known to or are found to cause transcription of DNA in plant cells in response to light can be used in the present invention. Such promoters may be obtained from a variety of sources such as plants and plant viruses and include, but are not limited to, the enhanced CaMV35S promoter and promoters isolated from plant genes such as small subunit of ribulose-1,5-biphosphate carboxylase (ssRUBISCO) genes. As described below, it is preferred that the particular promoter selected should be capable of causing sufficient expression to result in the production of an effective amount of PBGS enzyme to produce sufficient tetrapyrroles to sustain growth. In one embodiment, said promoter is leaky in order to provide tetrapyrroles necessary for the non-photosynthetic functions of the plant.

Plastid-Directed Expression of PBGS Activity

In a preferred embodiment of the invention, the PBGS gene is fused to a CTP, in order to target the PBGS protein to the plastid. As used hereinafter, chloroplast and plastid are intended to include the various forms of plastids including amyloplasts. Many plastid-localized proteins are expressed from nuclear genes as precursors and are targeted to the plastid by a CTP, which is removed during the import steps. Examples of such chloroplast proteins include the small subunit of ribulose-1,5-biphosphate carboxylase (ssRUBISCO, SSU), 5-enolpyruvateshikimate-3-phosphate synthase (EPSPS), ferredoxin, ferredoxin oxidoreductase, the light-harvesting-complex protein I and protein II, and thioredoxin F. The glyphosate-tolerant EPSP synthase plant gene also encodes a polypeptide which contains a CTP, which enables the EPSP synthase polypeptide to be transported into a chloroplast inside the plant cell [48]. It has been demonstrated that non-plastid proteins may be targeted to the chloroplast by use of protein fusions with a CTP and that a CTP sequence is sufficient to target a protein to the plastid. Those skilled in the art will also recognize that various other chimeric constructs can be made that utilize the functionality of a particular plastid transit peptide to import the PBGS enzyme into the plant cell plastid. The PBGS gene could also be targeted to the plastid by transformation of the gene into the chloroplast genome [49]. Generally chloroplast uptake signals such as the CTP are rich in Ser, Thr and small hydrophobic amino acid residues.

The RNA produced by a DNA construct of the present invention may also contain a 5' non-translated leader sequence. This sequence can be derived from the promoter selected to express the gene and can be specifically modified so as to increase translation of the mRNA. The 5' non-translated regions can also be obtained from viral RNAs, from suitable eukaryotic genes, or from a synthetic gene sequence. The present invention is not limited to constructs wherein the non-translated region is derived from the 5' non-translated sequence that accompanies the promoter sequence. Rather, the non-translated leader sequence can be derived from an unrelated promoter or coding sequence.

In monocots, an intron is preferably included in the gene construct to facilitate or enhance expression of the coding sequence. Examples of suitable introns include the HSP70 intron and the rice actin intron, both of which are known in the art. Another suitable intron is the castor bean catalase intron [50].

The 3' non-translated region of the chimeric plant gene contains a polyadenylation signal that functions in plants to cause the addition of polyadenylate nucleotides to the 3' end of the RNA. Examples of suitable 3' regions are (1) the 3' transcribed, non-translated regions containing the polyadenylation signal of Agrobacterium tumor-inducing (Ti) plasmid genes, such as the nopaline synthase (NOS) gene, and (2) plant genes like the soybean storage protein genes and the small subunit of the ribulose-1,5-bisphosphate carboxylase (ssRUBISCO) gene.

In developing the nucleic acid constructs of this invention, the various components of the construct or fragments thereof will normally be inserted into a convenient cloning vector, e.g., a plasmid that is capable of replication in a bacterial host, e.g., E. coli. Numerous vectors exist that have been described in the literature, many of which are commercially available. After each cloning, the cloning vector with the desired insert may be isolated and subjected to further manipulation, such as restriction digestion, insertion of new fragments or nucleotides, ligation, deletion, mutation, resection, etc. so as to tailor the components of the desired sequence. Once the construct has been completed, it may then be transferred to an appropriate vector for further manipulation in accordance with the manner of transformation of the host cell.

A recombinant DNA molecule of the invention typically includes a selectable marker so that transformed cells can be easily identified and selected from non-transformed cells.

Examples of such include, but are not limited to, a neomycin phosphotransferase (nptII) gene [51], which confers kanamycin resistance. Cells expressing the nptII gene can be selected using an appropriate antibiotic such as kanamycin or G418. Other commonly used selectable markers include the bar gene, which confers bialaphos resistance; a mutant EPSP synthase gene [52], which confers glyphosate resistance; a nitrilase gene, which confers resistance to bromoxynil [53]; a mutant acetolactate synthase gene (ALS), which confers imidazolinone or sulphonylurea resistance [54]; and a methotrexate resistant DHFR gene [55].

Plants that can be made to express the PBGS transgene include, but are not limited to, acacia, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassaya, cauliflower, celery, cherry, cilantro, citrus, clementines, coffee, corn, cotton, cucumber, Douglas fir, eggplant, endive, escarole, eucalyptus, fennel, figs, gourd, grape, grapefruit, honey dew, jicama, kiwifruit, lettuce, leeks, lemon, lime, Loblollypine, mango, melon, mushroom, nut, oat, oil seed rape, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, esunflower, sweet potato, sweetgum, tangerine, tea, tobacco, tomato, triticale, turf, a vine, watermelon, wheat, yams, and zucchini.

A PBGS gene can be inserted into the genome of a plant by any suitable method. Suitable plant transformation vectors include those derived from a Ti plasmid of Agrobacterium tumefaciens, as well as those disclosed, e.g., by [56-58] and EPO publication 120,516. In addition to plant transformation vectors derived from the Ti or root-inducing (R1) plasmids of Agrobacterium, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen. DNA may also be inserted into the chloroplast genome [49].

A plasmid expression vector suitable for the introduction of a PBGS gene in monocots using microprojectile bombardment is composed of the following: a CTP; a light inducible promoter; the PBGS gene; an intron that provides a splice site to facilitate expression of the gene, such as the Hsp70 intron [59]; and a 3' polyadenylation sequence such as the nopaline synthase 3' sequence (NOS 3'; [60]). This expression cassette may be assembled on high copy replicons suitable for the production of large quantities of DNA to be injected into the plant.

A particularly useful Agrobacterium-based plant transformation vector for use in transformation of dicotyledonous plants is plasmid vector pMON530 [61]. Plasmid pMON530 is a derivative of pMON505 prepared by transferring the 2.3 kb StuI-HindIII fragment of pMON316 [61] into pMON526. Plasmid pMON526 is a simple derivative of pMON505 in which the SmaI site is removed by digestion with XmaI, treatment with Klenow polymerase and ligation. Plasmid pMON530 retains all the properties of pMON505 and the CaMV35S-NOS expression cassette and now contains a unique cleavage site for SmaI between the promoter and polyadenylation signal.

Binary vector pMON505 is a derivative of pMON200 [61] in which the Ti plasmid homology region, LIH, has been replaced with a 3.8 kb HindIII to SmaI segment of the mini RK2 plasmid, pTJS75 [62]. This segment contains the RK2 origin of replication, oriV, and the origin of transfer, oriT, for conjugation into Agrobacterium using the tri-parental mating procedure [63]. Plasmid pMON505 retains all the important features of pMON200 including the synthetic multi-linker for insertion of desired DNA fragments, the chimeric NOS/NPTII'/NOS gene for kanamycin resistance in plant cells, the spectinomycin/streptomycin resistance determinant for selection in E. coli and A. tumefaciens, an intact nopaline synthase gene for facile scoring of transformants and inheritance in progeny, and a pBR322 origin of replication for ease in making large amounts of the vector in E. coli. Plasmid pMON505 contains a single T-DNA border derived from the right end of the pTiT37 nopaline-type T-DNA. Southern blot analyses have shown that plasmid pMON505 and any DNA that it carries are integrated into the plant genome, that is, the entire plasmid is the T-DNA that is inserted into the plant genome. One end of the integrated DNA is located between the right border sequence and the nopaline synthase gene and the other end is between the border sequence and the pBR322 sequences.

Another particularly useful Ti plasmid cassette vector is pMON17227. This vector is described in PCT Publication WO 92/04449 and contains a gene encoding an enzyme conferring glyphosate resistance (denominated CP4), which is an excellent selection marker gene for many plants, including potato and tomato. The gene is fused to the *Arabidopsis* EPSPS chloroplast transit peptide (CTP2) and expressed from the FMV promoter as described therein.

When adequate numbers of cells (or protoplasts) containing the PBGS gene are obtained, the cells (or protoplasts) are regenerated into whole plants. Choice of methodology for the regeneration step is not critical, with suitable protocols being available for hosts from Leguminosae (alfalfa, soybean, clover, etc.), Umbelliferae (carrot, celery, parsnip), Cruciferae (cabbage, radish, canola/rapeseed, etc.), Cucurbitaceae (melons and cucumber), Gramineae (wheat, barley, rice, maize, etc.), Solanaceae (potato, tobacco, tomato, peppers), various floral crops, such as sunflower, and nut-bearing trees, such as almonds, cashews, walnuts, and pecans. See, e.g., [64-68].

In one embodiment, the PBGS gene is derived from a species in which the PBGS enzyme does not comprise $Mg^{2+}$ but comprises $Zn^{2+}$. In a preferred embodiment, the species is yeast or human. In another preferred embodiment, a mutant PBGS gene is used to generate a transgenic plant. In a further embodiment, the PBGS gene is introduced into the plant genome by homologous recombination. The wild type human PBGS genomic DNA and full length cDNA which may be used to generate a transgenic plant are shown below:

```
Human PBGS gene (SEQ ID NO:1):[69]
cttacgcggtctgtgggagaccggagcgggagacagcggtgacaggagca gcggccgggagcccttaggaggcagacagagcctgcagccaatgcccca ggagccctcggttccaaccaactgatgcccctgtgcccactggcccacgc catgcagcccagtccgttctgcacagcggctacttccacccactacttc gggcctggcagacagccaccaccaccctcaatgcctccaacctcatctac cccatctttgtcacggatgttcctgatgacatacagcctatcaccagcct cccaggagtggccaggtatggtgtgaagcggctggaagagatgctgaggc ccttggtggaagagggcctacgctgtgtcttgatctttggcgtccccagc agagttcccaaggacgagcggggttccgcagctgactccgaggagtcccc agctattgaggcaatccatctgttgaggaagaccttccccaacctcctgg tggcctgtgatgtctgcctgtgtcccctacacctcccatggtcactgcggg ctcctgagtgaaaacggagcattccgggctgaggagagccgccagcggct ggctgaggtggcattggcgtatgccaaggcaggatgtcaggtggtagccc cgtcggacatgatggatggacgcgtggaagccatcaaagaggccctgatg gcacatggacttggcaacagggtatcggtgatgagctacagtgccaaatt tgcttcctgtttctatggcccttccgggatgcagctaagtcaagcccag cttttggggaccgccgctgctaccagctgcccctggagcacgaggcctg gctctccgagctgtggacccgggatgtacgggaaggagctgacatgctcat ggtgaagccgggaatgcctacctggacatcgtgcgggaggtaaaggaca agcaccctgacctccctctcgccgtgtaccacgtctctggagagtttgcc atgctgtggcatggagcccaggccggggcatttgatctcaaggctgccgt actggaggccatgactgccttccgcagagcaggtgctgacatcatcatca cctactacacaccgcagctgctgcagtggctgaaggaggaatgatggaga cagtgccaggcccaagaactagaactttaaaacgttcccggggcctcaga caagtgaaaaccaaagtaaatgctgcttttagaactgtgccctcatgccc tcttcctgctcacatgctagcggggcccagcagccctgggtggttttgcc agcatgctaactcttgtaactcgcagctgcatcctatgagctctcccaag cttccccgcccctccctgggtcagccgtgaggcccacctttgccaccct cagctctttcctctggtgtggcttcagcttgaaagcaacctggagtcggg ggcacagcctttgggggcctggctgggagagggtcttggagcattagggga agaagagagcagtgggatcttggggcctgagaagccttggaacgcttctg gcagcagagctgggtgtgggaatgaggcctagatcgatatccctgggtta gagttgaaatttgccgcaattccactggaaggcatttcccacgaggccag aggttgccaggctgcctgaggtctcctattctactctgaaccataaaccc agagaagaattactcattaaccagcataaatactgcctgaggatcaaaac tcagaggcaaagagggagttcctgactgctagaggtgccaccaccacaaa cacttttattcaggagatactttttgagaatctctgctctgttcctagg ttcagtgctgggtcctgggaatacagcaggacagacctcagcttatctct tcatagaaattatacaaagagaattggggagacagctaagaagaaaacaa agaaataaagcagttacaaattgtgataagtgctttgaaggaaagaaggg gtctgagacaacaacagggaagggcctctcttgaaacagtagttgggaa ggaggcagacatgcaccagtgatgtggtgacaggtgctctgaaggaggtc accaggacctgacctctttgaaggatcagaaaatacttccctgaaggact gacatttgagcctagacctgaagggtgagccatcaagctaagacaattgg ggaagagcattccaggggagagggaggagttgtgcaaaggccctggggctc cttctagctggaggaatgcaaggctagcttgtctggagcactgagaggat ggcctgaactgagtggagagagacagaccaggaccaaaccatgcagaggt caagggccacattcaccttttcagagtgactcaatcaaatttgtagtttg taaaagtattttaacagctctgcggcaaagtgcaaatgaaaagtcttgat ggcatggactggagcggggacagtggggatggagaaaggggaatggattg tggatgtgtttagaaggtagattcgatgtgaaggatgaatctggcttgac cttctgggtggctgatgggccatttactgagatggggcagcctggaagag gaacagaagcagggtcgggtggagggagaatactaaacttagcttgaga cattttgcaataaggaagctatatctagagtgcttatgtgactcacctaa ggccactcaacaagtttgtggcagaactggattagaactgcacagaaaac agccaagctgggatttgaacccatgtagtccaactccaaggcctctgccc ctaaccactgtgccataccacctcccaataatcaacagcaaaattatagg tctaacaatgttttatagacacccctccatttatgtgatgggtttgcatc ctgataaacccatcataagttgaaaatatgatcataagttgaaaatatga tcataagtcaaaaatgtatttaatatacctaacctaccaaacatcatagc
```

```
-continued
ttagcctagcctgccttaaacatgctcagaacacttacattagcctacag tgggcaaaactatccaacacaaaatctatattgtaataaagttgtaaaga attttgaataaaaattcaatatttgaaaaaaaaaaaaaaaaa Human PBGS cDNA (SEQ ID NO:2):[69]
gcagccaaagcccaggagccctaggttccaaccaactgatgccctgtg cccactggcccacgccatgcagcccagtccgttctgcacagcggctact tccacccactacttcgggcctggcagacagccaccaccaccctcaatgcc tccaacctcatctacccatctttgtcacggatgttcctgatgacataca gcctatcaccagcctcccaggagtggccaggtatggtgtgaagcggctgg aagagatgctgaggcccttggtggaagagggcctacgctgtgtcttgatc tttggcgtcccagcagagttcccaaggacgagcggggttccgcagctga ctccgaggagtccccagctattgaggcaatccatctgttgaggaagacct tccccaacctcctggtggcctgtgatgtctgcctgtgtccctacacctcc catggtcactgcgggctcctgagtgaaaacggagcattccgggctgagga gagccgccagcggctggctgaggtggcattggcgtatgccaaggcaggat gtcaggtggtagcccgtcggacatgatggatggacgcgtggaagccatc aaagaggccctgatggcacatggacttggcaacagggtatcggtgatgag ctacagtgccaaatttgcttcctgtttctatggcccttttccgggatgcag ctaagtcaagcccagcttttggggaccgccgctgctaccagctgcccct ggagcacgaggcctggctctccgagctgtggaccgggatgtacgggaagg agctgacatgctcatggtgaagccgggaatgccctacctggacatcgtgc gggaggtaaaggacaagcaccctgacctccctctcgccgtgtaccacgtc tctggagagtttgccatgctgtggcatggagcccaggccggggcatttga tctcaaggctgccgtactggaggccatgactgccttccgcagagcaggtg ctgacatcatcatcacctactacacaccgcagctgctgcagtggctgaag gaggaatgatggaggacagtgccaggcccaagaactagaactttcaaacg ttcccggggcctcagacaagtgacaaccaaagtaaatgctgcttttagaa ctgt Human PBGS amino acid sequence (SEQ ID NO:3):[69]
MQPQSVLHSGYFHPLLRAWQTATTTLNASNLIYPIFVTDVPDDIQPITSL

PGVARYGVKRLEEMLRPLVEEGLRCVLIFGVPSRVPKDERGSAADSEESP

AIEAIHLLRKTFPNLLVACDVCLCPYTSHGHCGLLSENGAFRAEESRQRL

AEVALAYAKAGCQVVAPSDMMDGRVEAIKEALMAHGLGNRVSVMSYSAKF

ASCFYGPFRDAAKSSPAFGDRRCYQLPPGARGLALRAVDRDVREGADMLM

VKPGMPYLDIVREVKDKHPDLPLAVYHVSGEFAMLWHGAQAGAFDLKAAV

LEAMTAFRRAGADIIITYYTPQLLQWLKEE
```

The compositions of the invention is suitable as antimicrobial active ingredients in personal care preparations, for example shampoos, bath additives, hair-care products, liquid and solid soaps (based on synthetic surfactants and salts of saturated and/or unsaturated fatty acids), lotions and creams, deodorants, other aqueous or alcoholic solutions, e.g. cleansing solutions for the skin, moist cleansing cloths, oils or powders. The invention therefore relates also to a personal care preparation comprising the composition of the invention and optionally cosmetically tolerable carriers or adjuvants as described in U.S. Pat. No. 6,689,372 to Holzl et al. The composition should be used in amounts effective to have the antimicrobial effect, i.e. inhibit or prevent microbial activity. Other constituents can be used, for example sequestering agents, colorings, perfume oils, thickening or solidifying (consistency regulator) agents, emollients, UV absorbers, skin-protective agents, antioxidants, additives that improve mechanical properties, such as dicarboxylic acids and/or Al, Zn, Ca and Mg salts of fatty acids, and optionally preservatives. Further, the invention provides a method of antimicrobial treatment of skin, mucosa or hair which comprises, contacting the surface of the skin, mucosa or hair of a person in need of said antimicrobial treatment with an antimicrobially effective amount of the compound of the invention.

The personal care preparation according to the invention may be formulated as a water-in-oil or oil-in-water emulsion, as an alcoholic or alcohol-containing formulation, as a vesicular dispersion of an ionic or non-ionic amphiphilic lipid, as a gel, a solid stick or as an aerosol formulation.

As a water-in-oil or oil-in-water emulsion, the cosmetically tolerable adjuvant contains, for example, from 5 to 50% of an oily phase, from 5 to 20% of an emulsifier and from 30 to 90% water. The oily phase may contain any oil suitable for cosmetic formulations, e.g. one or more hydrocarbon oils, a wax, a natural oil, a silicone oil, a fatty acid ester or a fatty alcohol. Preferred mono- or poly-ols are ethanol, isopropanol, propylene glycol, hexylene glycol, glycerol and sorbitol.

Cosmetic formulations according to the invention may be contained in a wide variety of cosmetic preparations as described in U.S. Pat. No. 6,689,372 to Holzl et al. Especially the following preparations, for example, come into consideration: skin-care preparations, e.g. skin-washing and cleansing preparations in the form of tablet-form or liquid soaps, soapless detergents or washing pastes; bath preparations, e.g. liquid (foam baths, milks, shower preparations) or solid bath preparations, e.g. bath cubes and bath salts; skin-care preparations, e.g. skin emulsions, multi-emulsions or skin oils; cosmetic personal care preparations, e.g. facial make-up in the form of day creams or powder creams, face powder (loose or pressed), rouge or cream make-up, eye-care preparations, e.g., eyeshadow preparations, mascara, eyeliner, eye creams or eye-fix creams; lip-care preparations, e.g., lipsticks, lip gloss, lip contour pencils, nail-care preparations, such as nail varnish, nail varnish removers, nail hardeners or cuticle removers; intimate hygiene preparations, e.g., intimate washing lotions or intimate sprays; foot-care preparations, e.g., foot baths, foot powders, foot creams or foot balsams, special deodorants and antiperspirants or callous-removing preparations; light-protective preparations, such as sun milks, lotions, creams and oils, sun blocks or tropicals, pre-tanning preparations or after-sun preparations; skin-tanning preparations, e.g., self-tanning creams; depigmenting preparations, e.g., preparations for bleaching the skin or skin-lightening preparations; insect-repellents, e.g., insect-repellent oils, lotions, sprays or sticks; deodorants, such as deodorant sprays, pump-action sprays, deodorant gels, sticks or roll-ons; antiperspirants, e.g., antiperspirant sticks, creams or roll-ons; preparations for cleansing and caring for blemished skin, e.g., soapless detergents (solid or liquid), peeling or scrub preparations or peeling masks; hair-removal preparations in chemical form (depilation), e.g., hair-removing powders, liquid hair-removing preparations, cream- or paste-form hair-removing preparations, hair-removing preparations in gel form or aerosol foams; shaving preparations, e.g., shaving soap, foaming shaving creams, non-foaming shaving creams, foams and gels, pre-shave preparations for dry shaving, aftershaves or after-shave lotions; fragrance preparations, e.g., fragrances (eau de cologne, eau de toilette, eau de parfum, parfum de toilette, perfume), perfume oils or cream perfumes; dental-care, denture-care and mouth-care preparations, e.g., toothpastes, gel tooth-pastes, tooth powders, mouthwash concentrates, anti-plaque mouthwashes, denture cleaners or denture fixatives; cosmetic hair-treatment preparations, e.g., hair-washing preparations in the form of shampoos and conditioners, hair-care preparations, e.g., pretreatment preparations, hair tonics, styling creams, styling gels, pomades, hair rinses, treatment packs, intensive hair treatments, hair-structuring preparations, e.g., hair-waving preparations for permanent waves (hot wave, mild wave, cold wave), hair-straightening preparations, liquid hair-setting preparations, foams, hairsprays, bleaching preparations; e.g., hydrogen peroxide solutions, lightening shampoos, bleaching creams, bleaching powders, bleaching pastes or oils, temporary, semi-permanent or permanent hair colourants, preparations containing self-oxidizing dyes, or natural hair colourants, such as henna or camomile.

The oral composition according to the invention may be, for example, in the form of a gel, a paste, a cream or an aqueous preparation (mouthwash).

The oral composition according to the invention may also comprise compounds that release fluoride ions which are effective against the formation of caries, for example inorganic fluoride salts, e.g. sodium, potassium, ammonium or calcium fluoride, or organic fluoride salts, e.g. amine fluorides, which are known under the trade name Olafluor.

The compositions of the invention are also suitable for the treatment of textile fibre materials. Such materials are undyed and dyed or printed fibre materials, e.g. of silk, wool, polyamide or polyurethanes, and especially cellulosic fibre materials of all kinds. Such fibre materials are, for example, natural cellulose fibres, such as cotton, linen, jute and hemp, as well as cellulose and regenerated cellulose. Preferred suitable textile fibre materials are made of cotton. The compositions of the invention can also be used in washing and cleaning formulations, e.g. in liquid or powder washing agents or softeners.

The compositions of the invention are also suitable for imparting anti-microbial properties to plastics, e.g., polyethylene, polypropylene, polyurethane, polyester, polyamide, polycarbonate, latex etc. Fields of use of compositions of the invention are, for example, floor coverings, plastics coatings, plastics container and packaging materials, kitchen and bathroom utensils (e.g., brushes, shower curtains, sponges, bathmats), latex filter materials (air and water filters), plastics articles used in the field of medicine, e.g. dressing materials, syringes, catheters etc., so-called "medical devices", gloves and mattresses.

Paper, for example, paper used for hygiene purposes, may also be provided with anti-microbial properties using the compositions according to the invention.

It is also possible for non-wovens, e.g. nappies/diapers, sanitary towels, panty liners, and cloths for hygiene and household uses, to be provided with antimicrobial properties in accordance with the invention.

The compositions can be used also in household and all-purpose cleaners for cleaning and disinfecting hard surfaces.

In addition to preserving cosmetic and household products, technical products, such as paper treatment liquors, printing thickeners of starch or of cellulose derivatives, surface-coatings and paints, can be preserved and provided with antimicrobial properties.

The compositions of the invention are also suitable for the antimicrobial treatment of wood and for the antimicrobial treatment of leather and the provision of leather with antimicrobial properties.

The compounds according to the invention are also suitable for the protection of cosmetic products and household products from microbial damage.

Further, the composition of the present invention can be used as an oral composition such as a dentifrice composition in association with an orally-acceptable carrier as described in U.S. Pat. No. 6,740,311 to White, Jr., et al. Non-limiting examples of such oral composition are toothpastes, tooth powders, prophylaxis pastes, lozenges, gums and the like suitable for humans and animals.

Further, the compositions of the invention can be used to prepare antimicrobial surfaces. Further provided is a method of making an antibacterial surface, the method comprising: (1) providing the composition of the invention wherein the composition is effective to inhibit or prevent formation of the active form of the multimeric porphobilinogen synthase and thereby inhibiting or preventing development or growth of bacteria, archaea, and/or eucarya, provided that the active form of the multimeric porphobilinogen synthase contains an allosteric magnesium binding site and the composition is at least one of a drug, a toothpaste, a soap, a disinfectant, an anti-biofilm composition, and a herbicide; (2) providing a surface-forming matrix; and (3) combining the composition with the surface-forming matrix and thereby making the antibacterial surface. In one variant of the method, the antibacterial surface is adapted to prevent or inhibit a formation of a biofim.

The term "a surface-forming matrix" as used herein includes polymers, biodegradable and non-biodegradabe, silicas, ceramics and combinations thereof for mixing, layering or otherwise associating the composition with the matrix. The composition can also be put on the top or a bottom surface of the matrix.

Further, this invention provides a method for manipulating growth or development of a plant comprising applying the composition of the invention in a form of a herbicide to the plant, wherein the plant is herbicide resistant and is adapted to be transgenic for a multimeric porphobilinogen synthase that substantially exist in a multimeric form of a hugging dimer. In one variant of the method, the multimeric porphobilinogen synthase contains no allosteric magnesium binding site.

The invention will be illustrated in more detail with reference to the following Examples, but it should be understood that the present invention is not deemed to be limited thereto.

EXAMPLES

Example 1

Discovery of the hexameric assembly of human PBGS variant F12L.

Protein Expression

The parent human PBGS is the well-characterized N59/C162A [70]. N59 corresponds to the more soluble of two co-dominant alleles encoding the PBGS protein. C162A is a benign mutation that removes the possibility of a slowly forming aberrant disulfide bond. The artificial gene for N59/C162A is called Wt below. The sense strand primer used for the QuikChange mutagenesis of Wt to the F12L variant was GGCTACCTCCACCCACTGCTTCGGGCC. Several constructs were prepared for the coexpression of Wt and F12L in E. coli. Both the order of the genes and the number of promoters were varied, but these variations did not affect the outcome. The construct containing Wt and F12L under the control of one promoter is described. Plasmid DNA containing Wt (pET3aWt) was digested with BamHI and NdeI to cut out Wt. The pET17b vector DNA was linearized by digestion with BamHI and NdeI and ligated with Wt such that the ATG start codon of Wt was 6 basepairs downstream of the ribosomal binding site encoded by the vector. The resultant plasmid was transformed into *E. coli* XL1 blue. Plasmid DNA (pET17bWt) was prepared and linearized with SpeI and Bpu1102I. Plasmid DNA containing the gene F12L (pET3aF12L) was digested with XbaI and Bpu1102I to produce a fragment containing the ribosomal binding site and the gene for F12L. The gene for F12L and the linearized pET17Wt vector were ligated such that the ribosomal binding site of the F12L gene was 35 base pairs downstream of the stop codon of Wt, and the terminator was 52 base pairs downstream of the stop codon for the F12L gene. Plasmid pET17bWtF12L was transformed into *E. coli* XL1blue, plasmid DNA was prepared and transformed into *E. coli* BLR (DE3) for protein expression as previously described [70].

Protein Purification

Figure 17A:
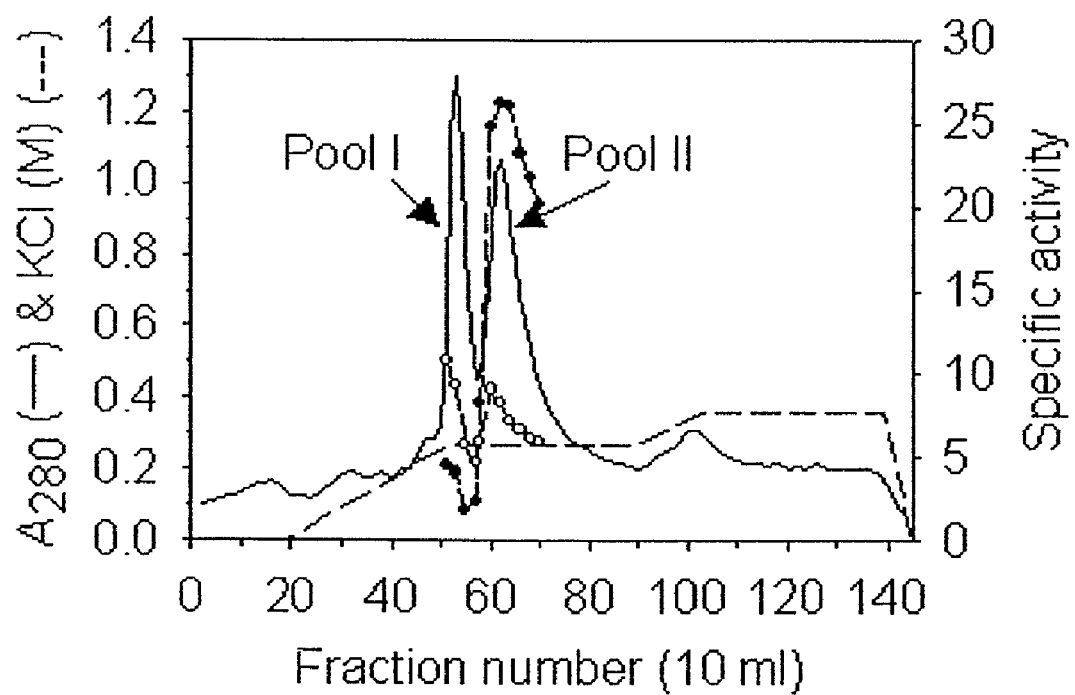
FIG. 17A shows the chromatographic separation of two peaks of heterologously expressed WT+F12L (both genes on the same mRNA) in on Q-Sepharose (KCl gradient (---), A280 (–)). Pool I contains hetero-hexamers and Pool II contains hetero-octamers.

The bulk of the protein purification procedure (cell disruption, ammonium sulfate fractionation, hydrophobic chromatography on Phenyl-Sepharose, anion exchange chromatography, and gel filtration chromatography on Sephacryl S-300) followed the procedures previously described [70] with the exception that a 70 ml Q-Sepharose column was used in place of the DEAE agarose column for the anion exchange step. The Q-Sepharose was run at room temperature using 30 mM potassium phosphate, pH 7.0, 10 mM 2-mercaptoethanol, 10 µM Zn(II), and employed a KCl gradient as shown in FIG. 17A. The gradient was controlled by a Rainin HPLC system run at a flow rate of 3 ml min$^{-1}$ and 10 ml fractions were collected.

Kinetic Characterization of the PBGS Variants was Used to Show that WT and F12L have Different Functional Characteristic:

All kinetic determinations were carried out in 0.1 M bis-tris propane, 10 mM 2-mercaptoethanol, 10 µM Zn. For the pH rate profiles, the reported pH reflects the assay pH after the addition of 10 mM ALA-HCl. For $K_m$ and $V_{max}$ determinations, concentrations of ALA were 10 µM, 30 µM, 100 µM, 300 µM, 1 mM, 3 mM, and 10 mM and were each done in duplicate. Variations in the concentration of ALA-HCl did not lead to variations in final pH because the stock 0.1 M ALA-HCl was diluted into 0.1 M HCl prior to addition of a constant volume to the assay mixture. All assays were at 37° C. for a fixed time using Ehrlich's reagent to determine porphobilinogen formed.

Analytical Ultracentrifugation:

Protein samples were dialyzed into 30 mM potassium phosphate, pH 7.5, 0.1 mM DTT, and 10 µM $ZnCl_2$ just prior to loading into the ultracentrifuge. Loading concentrations were 10.6 µM and 12.8 µM for wild type and F12L mutant enzyme, respectively. All sedimentation equilibrium experiments were carried out at 4° C. using a Beckman Optima XL-A analytical ultracentrifuge equipped with an An60 Ti rotor and using six-channel, 12-mm path length, charcoal-filled Epon centerpieces using quartz windows. Data were collected at three rotor speeds (8,000, 11,000, and 14,000 rpm) and represent the average of 20 scans using a scan step size of 0.001 cm. Temperature-corrected partial specific volumes and solution density were calculated using the Sednterp program [71]; the solution density was 1.00191 gm/mL and the partial specific volumes were 0.7394 and 0.7397 mL/gm for the wild type and mutant proteins respectively. Data were analyzed using the HID program from the Analytical Ultracentrifugation Facility at the University of Connecticut (Storrs, Conn.). Model analysis of the data ruled out a single species as the residuals from the fits were clearly nonrandom.

A Crystal Structure was Determined for F12L

F12L was dialyzed against 50 mM bis-tris propane, 10 mM βME, and 10 µM $ZnCl_2$. Crystals were formed using the sitting drop method, equal volume of F12L (4.0 mg ml-1) was mixed with the precipitant (0.4 M monoammonium hydrogen phosphate). ALA was added equimolar to the protein subunit concentration and crystals formed in 3-5 days. Diffraction data were collected at 100K on MAR345 image plate detector coupled with RU-200 rotating anode generator equipped with OSMIC optics and operated at 50 kV and 100 ma. Crystals were cryoprotected before freezing by transferring them at reservoir solutions containing 12%, 17%, 23% and 30% glycerol for 3 min in each solution. A few data sets were collected showing high degree of disorder and lack of any ligand in the active site area. Because of that, a crystal of F12L was soaked in 2 mM ALA, which was added to the first two cryoprotectant solutions and 0.2 mM $ZnCl_2$, which was added to the last two solutions in addition to ALA. The final data set consisted of 525 frames corresponding to 0.50 oscillation with exposure time 3.5 min per frame. Crystals belong to a hexagonal system, space group $P6_3$, unit cell parameters a=b=89.6 Å, c=153.2 Å. There are two molecules in the asymmetric unit. Diffraction data were reduced with the program package HKL2000, $R_{merge}(I)$=5.0% for 33,615 reflections for the 45-2.2 Å resolution range.

The structure was solved by molecular replacement with the AmoRe program package by using molecule A of human PBGS structure (pdb code 1E51) as an initial model. Refinement was carried out with program CNS. The final model included one dimer of F12L—molecule A (residues 11-82, 97-124, 140-169, 172-212, 222-330) and B (residues 3-82, 97-122, 140-169, 172-212, 226-328), one molecule of an intermediate product of the catalytic reaction bound in the active site of molecule A, 241 water molecules and two atoms of Zn which appear to have low occupancies. The crystallographic R-factor is 19.9%, R(free) is 28.6% for 2.2 Å resolution data, and the RMS deviations for bond lengths and bond angles are 0.18 Å and 2.0°, respectively. All residues belong to allowed conformation regions on the Ramachandran plot.

The Properties of Human PBGS Variant F12L

Human PBGS variant F12L is remarkably different from the wild type protein. Characterization of purified F12L confirmed that the catalytic activity is very low under conditions where wild type human PBGS is most active. However, F12L exhibits a remarkably altered pH rate profile and shows considerable activity at basic pH values (FIG. 12). The $K_m$ and $V_{max}$ values of F12L and wild type human PBGS were determined at pH 7, which is optimal for the wild type protein, and at pH 9, which is optimal for F12L; the results are presented in Table 1. F12L exhibits normal Michaelis-Menten kinetics with extraordinarily high $K_m$ values, well above physiological concentrations of the substrate 5-aminolevulinic acid (ALA). However, at pH 9 the $V_{max}$ of F12L is significantly higher than that of the wild type protein. Under conditions of optimal pH and in the presence of an optimal configuration of metal ions, wild type PBGS from all species characterized are reported to have $K_m$ values in the range of 100 µM [14,31,70,72], as is seen here for wild type human PBGS at pH 7. The kinetic behavior of wild type human PBGS at pH 9 did not exhibit standard Michaelis-Menten kinetics, the basis of which was not at first apparent. On cursory examination, the wild type protein appeared to exhibit an extreme negative cooperativity with a Hill coefficient on the order of 0.35. In fact, the best fit for the data was to a double hyperbolic equation, which was later appreciated to derive from catalysis by a mixture of quaternary isoforms (morpheeins, octamer and hexamer) where the two forms have very different Km values. This phenomenon is described in more detail below.

Further evidence for extraordinary differences between the F12L variant and the wild type protein came from variations in mobility during anion exchange chromatography (FIG. 16A) and during native gel electrophoresis (FIG. 16B), both of which suggest a difference in oligomeric structure. Separation on an anion exchange column generally reflects a different surface charge, which cannot be due to the replacement of neutral leucine for neutral phenylalanine. Separation of two species with identical charge/mass ratio by electrophoresis indicates either a different size or a different shape. Together, these differences suggested that F12L and wild type human PBGS exist in different oligomeric states.

When the wild type and mutant proteins were subjected to sedimentation equilibrium analysis using an analytical ultracentrifuge, the molecular weight for the wild type protein and F12L were found to be 244,000±8,900 and 197,900±6,500 Daltons, respectively. The former is midway between that expected for an octamer and a hexamer, while the latter is midway between that expected for a hexamer and a tetramer. In model analysis of the data, the wild type protein fit best to a three-state model of dimer, hexamer, and octamer at 7.6%, 51%, and 42% respectively, while F12L fit best to a two-state model of tetramer and hexamer at a ratio of 70% to 30%, with octamer absent. Hence the inventor undertook the determination of the crystal structure of human PBGS variant F12L.

The Crystal Structure of Human PBGS and the F12L Variant Show Remarkable Differences in the Structure of the Monomer, which Dictates a New Quaternary Isoform and Reveals the First Example of Morpheeins:

Seventeen previously determined crystal structures of PBGS [29,30,40,73-79] from fungi, metazoa, and bacteria reveal a common homo-octameric structure in which four dimers are related by a 90° rotation around a central axis (FIG. 2). PBGS is a member of the aldolase superfamily of TIM $\alpha/\beta$ barrel proteins [80]. In each subunit the catalytic core resides completely within the barrel and a 20+ amino acid N-terminal arm is involved in extensive subunit interactions. The sequence of the catalytic core is phylogenetically conserved, but that of the N-terminal arm is not. The PBGS dimer seen in the octamer (FIG. 2, left) involves highly conserved barrel-to-barrel contacts and the N-terminal arm of one subunit is hugging the barrel of the sister subunit. Hence, this has been referred to as the hugging dimer [9]. The side chain of amino acid 12 does not participate in the hugging interaction. Assembly of the tetramer, which is by addition of a second hugging dimer rotated 90° around the central axis (FIG. 2, middle), adds an additional reciprocal interaction between the arm of one subunit and the base of an $\alpha/\beta$ barrel from a neighboring dimer. The side chain of amino acid 12 participates in this subunit interaction. Addition of two more dimers, each rotated 90° around the central axis results in the octamer (FIG. 2, right). The octamer, rotated 90° toward the reader relative to the view of the dimer and tetramer, and gives a pinwheel representation. Prior to the determination of the crystal structure of F12L, it was presumed that all PBGS proteins shared the same homo-octameric structure [9]. However, for PBGS from green plants and some bacteria, there is kinetic evidence suggesting that the maximally active octamer can dissociate into smaller, less active, structural units [13,14]. This kinetic evidence is a protein concentration to the specific activity as illustrated in FIGS. 5 and 20B for pea PBGS.

Strikingly, the newly determined crystal structure of the F12L human PBGS allele (PDB Code 1PV8) reveals a quaternary structure that involves significant rearrangement of the N-terminal arm relative to the $\alpha/\beta$ barrel (FIG. 9). In this case, the dimer retains the aforementioned barrel-to-barrel contacts but the N-terminal arms are detached rather than hugging (FIG. 9, left). Assembly of the tetramer retains the aforementioned reciprocal interaction between the arm of one subunit and the base of an $\alpha/\beta$ barrel from a neighboring dimer. However, because the arm is jutting out, this association dictates a 120° rotation around the central axis. Hence, in the oligomeric structure there are three detached-dimers, each rotated 120° around a central axis to form a hexamer (FIG. 9, right, viewed in the pinwheel representation). The unprecedented structural transition from the octamer observed for wild type human PBGS to the hexamer observed for F12L is an outstanding example of how a small mutational change can have a profound effect on the structure and function of a protein and indicates how close in energy these two quaternary forms are. It is also clear from viewing these structures that any equilibration between octamer and hexamer must proceed through the interconversion of the hugging dimer and the detached dimer. This interconversion process is illustrated in FIG. 24.

The new structure of F12L (2.2 Å resolution) contains significant regions of disorder that impede a structural comparison of the active site relative to the previously deposited wild type human PBGS structure (PDB code 1E51, 2.83 Å resolution). Amino acid 12 does not interact directly with active site residues in either structure. Furthermore, for those amino acids observed in both structures, most are superimposable. Thus, to further probe the basis for the unusual kinetic properties of F12L (e.g., FIG. 12, Table 1), the inventor undertook coexpression of F12L and wild type human PBGS.

Example 2

This example describes experiments demonstrating that the quaternary structure, rather than the specific mutation is responsible for the unusual properties of F12L.

Figure 17B:
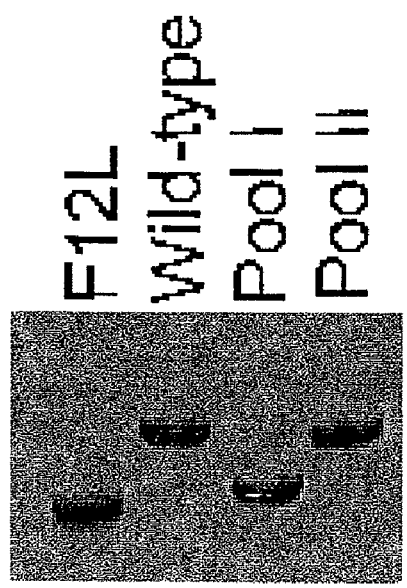
FIG. 17B shows the differential mobility of two pools of WT+F12L relative to wild type (WT) human PBGS and F12L on native gel electrophoresis.
Figure 17C:
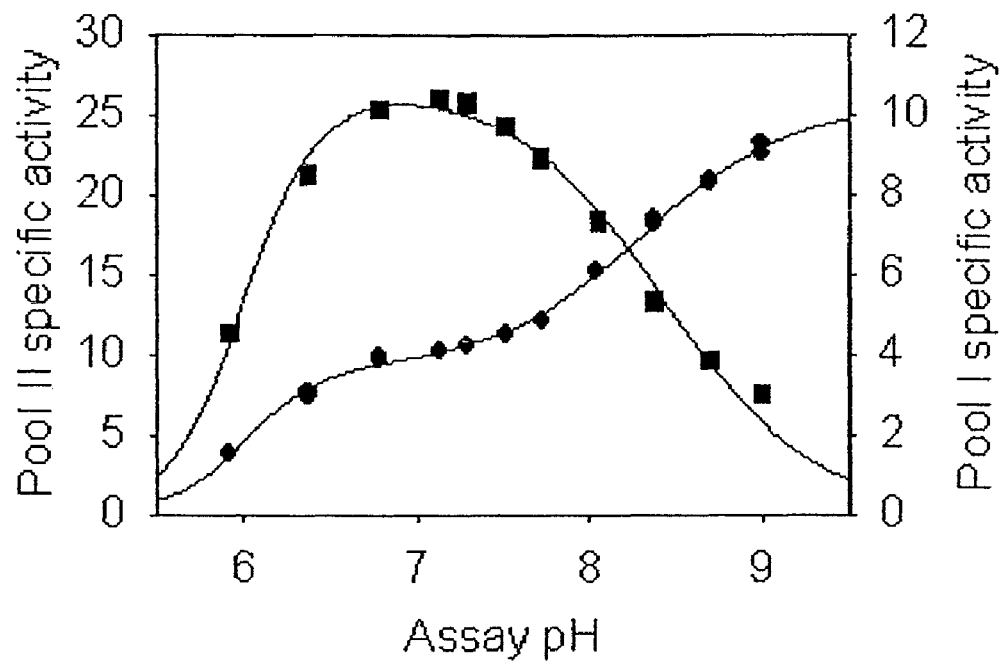
FIG. 17C shows the pH rate profiles for Pool I (●) and Pool II (■) of WT+F12L (as per FIG. 17A) following further purification on Sephacryl S300.

Coexpression of Wild Type Human PBGS and F12L Revealed that the Quaternary Structure is the Basis for the Kinetic Differences:

A coexpression system was prepared to produce both wild type human PBGS and the F12L variant in a 1:1 ratio from the same RNA message. Purification of the co-expressed protein, called WT+F12L, was found to yield two distinct peaks of PBGS protein on anion exchange chromatography (FIG. 17A). The peak to elute first (Pool I) runs comparably to F12L on a native gel, while the second peak (Pool II) runs comparably to wild type human PBGS (FIG. 17B). Pool I showed enhanced activity at pH 9 and Pool II showed enhanced activity at pH 7 (FIG. 17C). Both pools were individually subjected to analysis by mass spectroscopy following a tryptic digest and each was found to contain significant amounts of both the N-terminal 2010.2 Dalton Phe-containing peptide and the 1976.2 Dalton Leu-containing peptide, confirming that both pools contain heteromeric species. The percentage of each chain in the heteromeric pools was quantified by N-terminal sequencing to show that the Pool I contains 48.5% Phe and 51.5% Leu while Pool II contains 71.1% Phe and 28.3% Leu. These ratios were later found to vary with each purification, which was revealed to be through the disproportionation reaction illustrated in Example 3. These ratios do not obviously reveal what governs the quaternary structure of the heteromeric species. Pools I and II were further purified by gel filtration on Sephacryl S300, which reduced cross contamination of the heteromers. The pH rate profiles of the S300 purified Pools I and II are remarkably like F12L and wild type human PBGS, respectively (FIG. 17C). Based on the chromatographic, mass spectroscopy, and quantitative N-terminal sequencing data, it is concluded that Pool I is comprised of heterohexamers and that Pool II is comprised of heterooctamers. The pH rate profiles are found to be dominated more by the quaternary structure than by the amino acid composition at position 12.

Figure 17D:
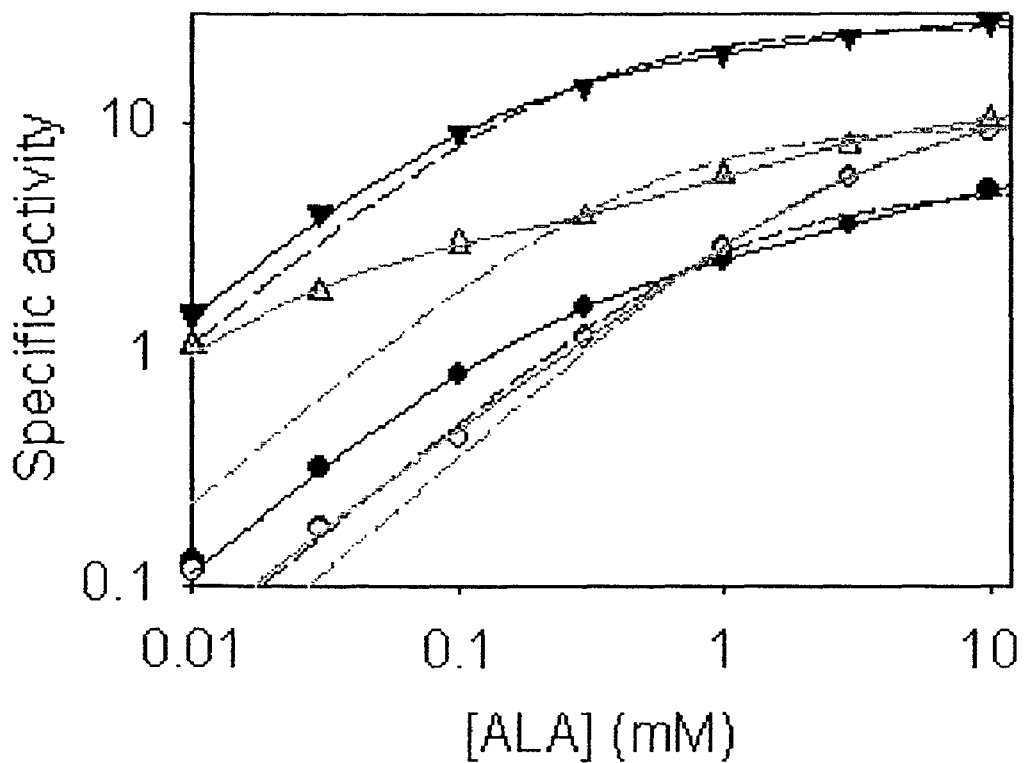
FIG. 17D shows a plot of activity versus concentration of ALA (10 μM-10 mM) for determining the $K_m$ and $V_{max}$ values for the S300 purified Pool I (circles) and Pool II (triangles) at pH 7 (filled) and pH 9 (open). The solid lines represent best fits of the data to the double hyperbolic equation (indicative of catalysis by a mixture of morpheeins). The dashed lines, each poor fits, show the results of fitting the data to a single hyperbolic equation.

The kinetic parameters $K_m$ and $V_{max}$ of the S300 purified pools were determined at pH 7 and at pH 9 (Table 3 contains data for hetero-hexamers (Pool I) initially at 70% Leu and 30% Phe and for hetero-octamers (Pool II) initially at 30% Leu and 70% Phe). The kinetic data do not follow a simple Michaelis-Menten relationship (hyperbolic fit), but can be attributed to catalysis by two different forms of the enzyme that have different $K_m$ and $V_{max}$ values (double hyperbolic fit) [81]. FIG. 17D shows activity as a function of substrate concentration; the kinetic data uniformly fit a model where hexameric and octameric forms of the enzyme exhibited high and low $K_m$ values, respectively. This double hyperbolic fit (solid lines) is far superior to the single hyperbolic fit (dashed lines). With the exception of the trace amount of octamer present for Pool I that is detected at pH 9, all the kinetic values are well determined (see Table 3). The data for wild type human PBGS at pH 9 also provided a superior fit to the octamer-hexamer model and this solution is included in Tables 1 and 3. The factors that govern equilibration of human PBGS heteromers under assay conditions remain to be elucidated.

Pool I and Pool II are the two pools of PBGS activity eluted from the Q-Sepharose column, as illustrated in FIG. 17A, and following further purification on a Sephacryl S-300 column. $K_{m1}$ and $K_{m2}$ (both mM) are interpreted as the $K_m$ for the octamer and hexamer, respectively.

The reported $V_{max}$ values (in units of μmoles h$^{-1}$ mg$^{-1}$) reflect the mole fraction of quaternary species under assay conditions, which remains to be determined. Fitted $K_m$ values are independent of the distribution of quaternary species.

Example 3

This example describes experiments demonstrating that the octameric and hexameric morpheeins of human PBGS can exist in a dynamic equilibrium, thus proving that morpheein equilibria, such as are illustrated in FIG. 24, can exist.

The kinetic behavior of oligomers described above led to the hypothesis that turnover facilitates the interconversion of the oligomeric structures. The experiments below demonstrate that the interactions of ligands at the enzyme active site promote the structural interconversion between human PBGS quaternary structure isoforms, favoring formation of the octamer. This observation illustrates that the assembly and disassembly of oligomeric proteins can be facilitated by the protein motions that accompany enzymatic catalysis.

Although the thermodynamic foundation for the preference of wild-type human PBGS and F12L to assemble into octamer and hexamer respectively remains unclear, the current study capitalizes on this differential preference to evaluate factors that effect the interconversion of quaternary structure isoforms of WT+F12L. The experiments below substantiate the hypothesis that the hetero-oligomers of human PBGS can interconvert, as shown in FIG. 24, upon addition of substrate. This is the first time such a dynamic structural rearrangement has been demonstrated. The current work exploits the different kinetic, chromatographic, and electrophoretic properties of the hexamers and octamers, and utilizes dynamic light scattering to determine the factors that catalyze the interconversion of PBGS quaternary structure isoforms.

PBGS from any organism has not been observed in a form smaller than the dimer. Thus heteromeric WT+F12L proteins are believed to be made up of stable dimers of three compositions, which are at position 12, Phe+Phe, Phe+Leu, and Leu+Leu. As some heterologously expressed human PBGS partitions to inclusion bodies, one cannot assume that the ratio of these dimers is 1:2:1 in the soluble isolated protein. However, because the homomeric Phe12 containing protein folds and assembles preferentially as the octamer and the homomeric Leu12 containing protein folds and assembles exclusively as the hexamer, one can propose that Phe+Phe

TABLE 3

Kinetic parameters of homomeric and heteromeric human PBGS.[a]

|  |  | F12L[b] | WT[b] | WT + F12L Pool I | WT + F12L Pool II |
|---|---|---|---|---|---|
| $K_{m1}$ | pH 7 |  | 0.25 ± 0.01 | 0.47 ± 0.07 | 0.19 ± 0.01 |
| $V_{max1}$ | pH 7 |  | 55.5 ± 0.2 | 2.98 ± 0.38 | 13.06 ± 0.40 |
| $K_{m2}$ | pH 7 | 17.7 ± 1.1 |  | 7.34 ± 1.53 | 5.05 ± 0.96 |
| $V_{max2}$ | pH 7 | 1.14 ± 0.05 |  | 6.60 ± 0.23 | 9.05 ± 0.37 |
| $K_{m1}$ | pH 9 |  | 0.015 ± 0.001[c] | 0.69 ± 0.15 | 0.05 ± 0.01 |
| $V_{max1}$ | pH 9 |  | 8.16 ± 0.13 | 2.99 ± 0.80 | 1.89 ± 0.25 |
| $K_{m2}$ | pH 9 | 4.6 ± 0.1 | 4.46 ± 0.80 | 4.17 ± 1.80 | 1.50 ± 0.24 |
| $V_{max2}$ | pH 9 | 18.2 ± 0.2 | 6.67 ± 0.36 | 2.74 ± 0.66 | 4.78 ± 0.19 |

[a]The $K_m$ and $V_{max}$ values were obtained by varying [ALA] from 3 μM-10 μM and were calculated by fitting the kinetic data to equation 1. $K_{m1}$ and $K_{m2}$ (both mM) are interpreted as the Km values for the octamer and hexamer, respectively. The reported Vmax values (μmol h$^{-1}$ mg$^{-1}$) reflect the mole fraction of quaternary species under assay condition.
[b]Data were taken from Table 1 and reference [39].
[c]A previous reported [39] $K_{m1}$ at pH 9 for WT was 0.35 ± 0.09; this was a misprint that represented the alternative fit of the kinetic data to the Hill equation.

dimers will preferentially assemble to the octamer and that Leu+Leu dimers will preferentially assemble to the hexamer. This is qualitatively consistent with the observed Phe:Leu ratio of the hetero-oligomers reported previously [39] and confirmed herein. Following this rationale, one can also propose that a dynamic re-equilibration of heteromeric oligomers (FIG. 24) would result in a disproportionation reaction that favors accumulation of Phe 12 in the octamer and Leu12 in the hexamer.

Equilibrium Dialysis Experiments

The dialysis buffer was 0.1 M BTP-HCl at desired pH values, 10 mM βME and 10 μM $ZnCl_2$. The reported pH values reflect the dialysis buffer pH after the addition of ALA (where included). Protein solutions (~200 μl at 3-7 mg/mL) were dialyzed in the presence or absence of ALA against 300 mL of buffer at 37° C. for 24 hours or longer under gentle agitation (50-60 μM) in an air shaker. Samples of the buffer were periodically withdrawn for determination of porphobilinogen concentration using Ehrlich's reagent (see above). Samples were also taken from the dialysis cassette at desired time points for native gel electrophoresis. Gels were then scanned and the fractional intensity of the protein bands at each time point was analyzed using SigmaGel™ Gel Analysis Software (Jandel Corporation).

Native Gel Electrophoresis

Native gel electrophoresis was done on a PhastGel system (Amersham Bioscience). Samples were prepared by mixing the protein solution with native gel running buffer (0.1 M Tris/HCl pH 8.8, 20% glycerol, 0.0025% Bromophenol Blue) to reach a final protein concentration of ~1 mg/mL. Four μl of each sample solution was loaded on homogeneous 12.5 polyacrylamide gel (Amersham Bioscience, 12.5% total acrylamide in separation zone, buffer 0.112 M acetate, 0.112 M Tris, pH 6.5). The gels were run with PhastGel native buffer strips (Amersham Bioscience, 0.88 M L-alanine, 0.25 M Tris, pH 8.8, made of 3% Agarose IEF). After separation, gels were developed on PhastGel system using Coomassie staining.

Light Scattering Measurements

The molecular weight change during substrate induced dynamic interconversion was monitored using a temperature-controlled DynoPro Dynamic Light Scattering Instrument (Protein Solutions Inc.) at 37° C. Protein (~1 mg/mL) was preincubated in assay buffer at 37° C. for 10 min. Immediately after the addition of ALA to a final concentration of 10 mM, the solution mixture was filtered through a 0.2 μm membrane into a 37° C. pre-warmed light scattering cuvette. The cuvette was kept at 37° C. in an incubator during the experiment except the times at which the light scattering measurements were taken. The average molecular weight calculated was based on the measurement of $KC/R_{90}$ [82]. The calculated molecular weights are lower than that expected for octamer and hexamer presumably due to the presence of a small concentration of the dimers.

Mass Spectral Analysis of the Disproportionation of Heteromeric Oligomers

WT+F12L Pool I and Pool II protein solutions underwent 24 hours of equilibrium dialysis in the presence of 10 mM ALA. The hexameric and octameric forms of the protein were separated after the dialysis using a 1 ml Mono-Q column. The Mono-Q buffer was 30 mM potassium phosphate, pH 7.0, 10 mM βME and 10 μl $ZnCl_2$. The hexameric and octameric forms were separated using a 0.02-1.0 M KCl gradient in 27 column volumes. Fractions containing hexameric and octameric forms were pooled and concentrated to a final concentration of ~1 mg/mL. The concentrated pools were dialyzed against 300 mL of 2 mM BTP-HCl buffer at pH 7.0 for 3 hours to remove the phosphate from the Mono-Q buffer. Samples were subject to overnight trypsin (Promega, sequencing grade modified) digestion using 1:20 (w/w) trypsin:protein ratio. The tryptic peptide mixtures were spotted on a gold plate with cyano-4-hydroxycinnamic acid matrix on top of that. The mass spectral data was collected using Reflex IV Matrix Assisted Laser Desorption/Ionization Time-of-Flight mass spectrometer (Bruker Inc.)

Figure 25A:
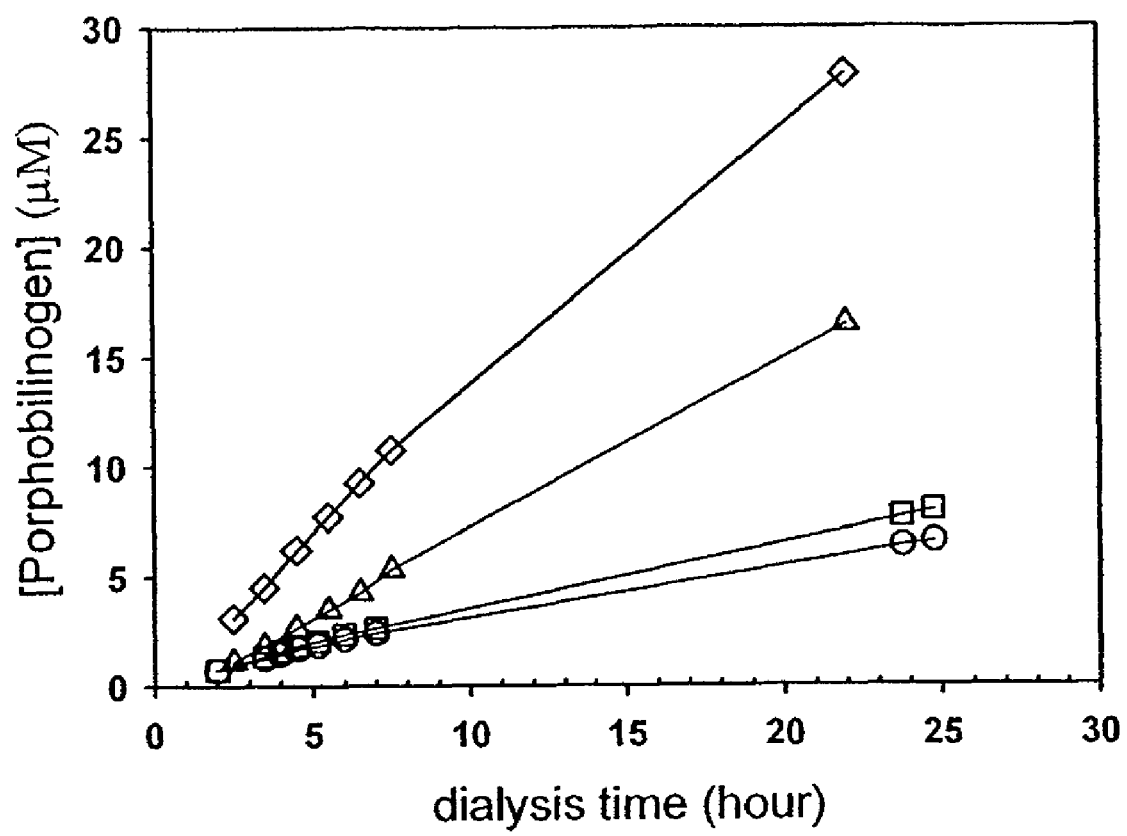
FIGS. 25A-C demonstrate dynamic interconversion of heteromeric WT+F12L human PBGS during equilibrium dialysis.
Figure 25B:
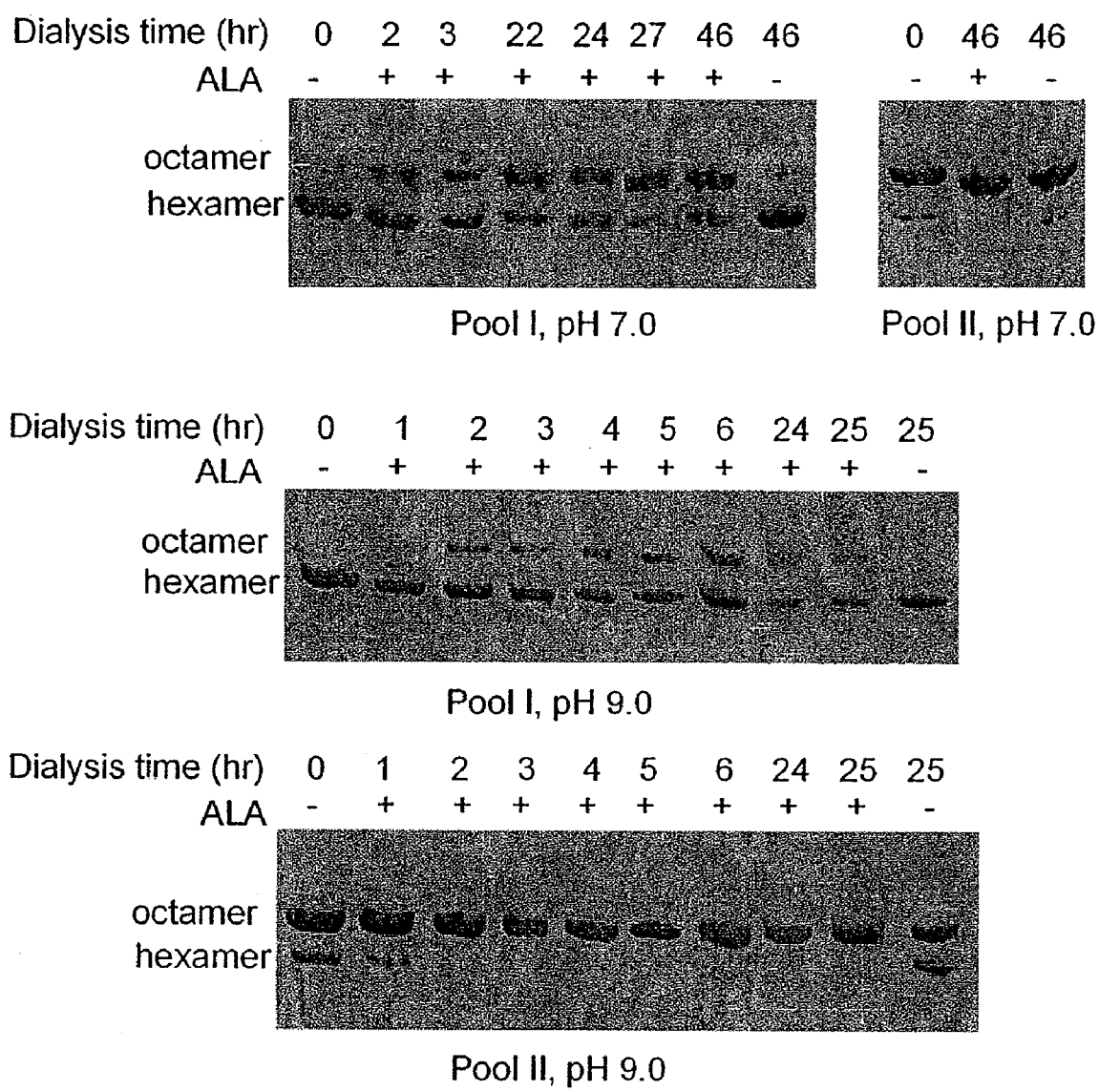
Figure 25C:
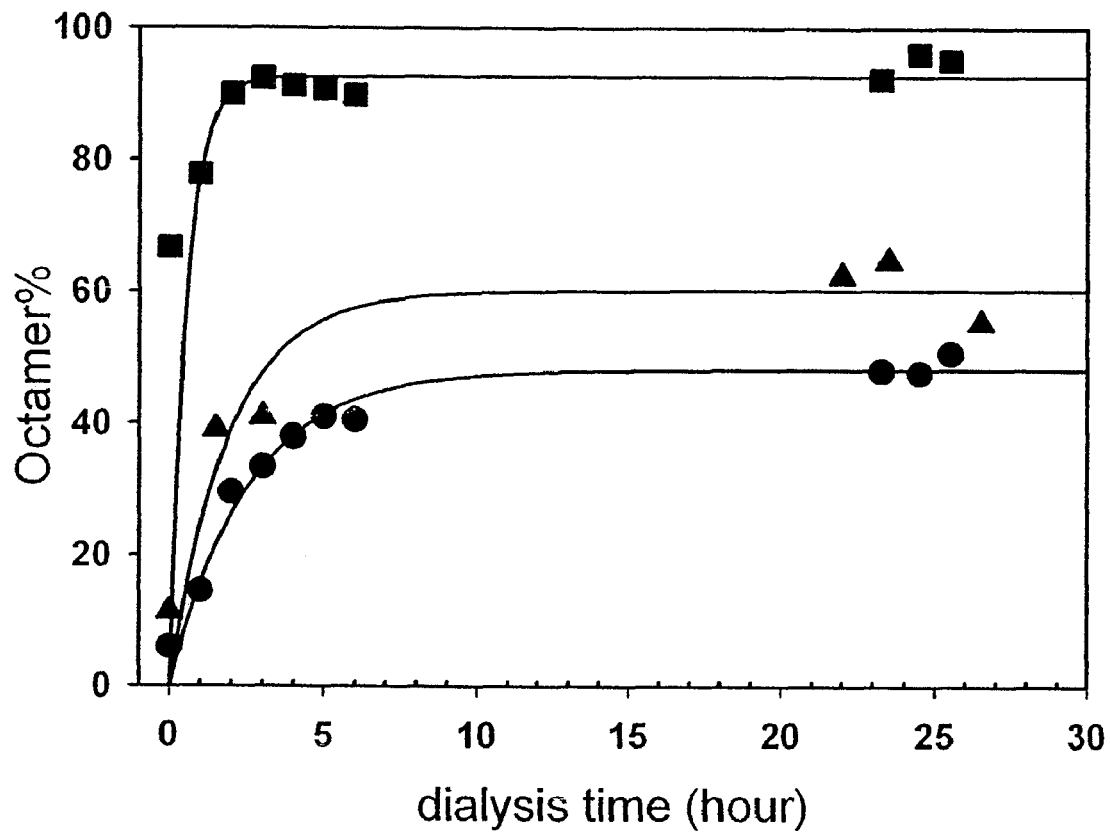

Interconversion and reequilibration of (WT+F12L) heteromeric oligomers were monitored by equilibrium dialysis. Using heteromeric Pool I and Pool II, equilibrium dialysis was used to provide a physical demonstration that substrate can promote the reequilibration between octamer and hexamer as per the reaction illustrated in FIG. 24. The proteins comprised of Pool I and Pool II were separately dialyzed at 37° C. in the presence and absence of the substrate, ALA, and the quaternary structure was probed by native gel electrophoresis as a function of dialysis time. Product formation was monitored in the dialysate and indicated that catalysis was ongoing throughout the dialysis procedure (FIG. 25A). The electrophoretic results (FIG. 25B) show that the oligomeric structures are stable for at least 46 hours when dialysis is carried out in the absence of substrate. However, the presence of the substrate causes a dramatic reequilibration of quaternary structure isoforms, favoring accumulation of the octamer in all cases (Pool I and Pool II at pH 7.0 and pH 9.0). These pH values correspond to the optimal pH for the activity of the octamer and the hexamer respectively[39]. Densitometry was used to estimate the rate and extent of the re-equilibration reaction for Pool I at pH 7 and pH 9 and for Pool II at pH 9 (FIG. 25C), where the data was fitted to a exponential function and fit to rate constants of 0.54 $h^{-1}$ (Pool I, pH 7), 0.4 $h^{-1}$ (Pool I, pH 9), and 1.8 $h^{-1}$ (Pool II, pH 7) respectively. The rate and extent of conversion of Pool I to octamer was greater at pH 7 than at pH 9, suggesting that there is a pH dependence to the equilibrium between the PBGS quaternary structure isoforms. This is consistent with data on wild type human PBGS (octamer) where kinetic evidence indicates catalysis by both octamer and hexamer at pH 9 but catalysis only by octamer at pH 7 [39].

Analysis of Pool I and Pool II oligomers following the substrate induced interconversion of quaternary isoforms.

Figure 26A:
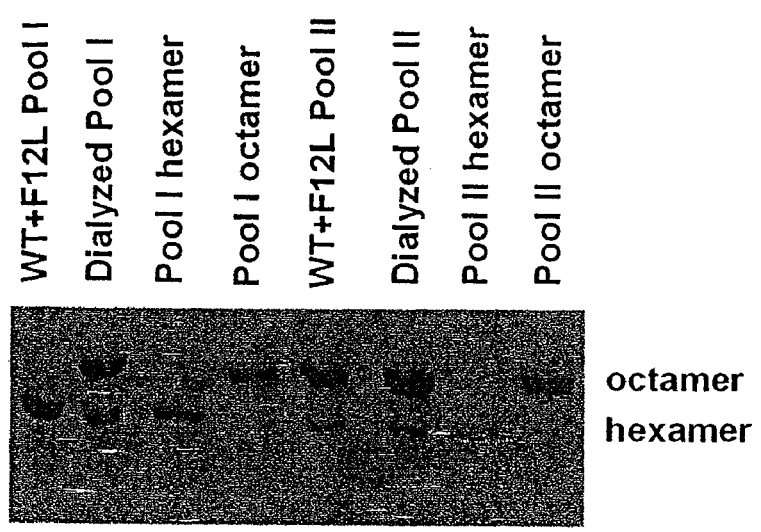
FIGS. 26A and B demonstrate analysis of the disproportionation products of human Wt+F12L Pool I and Pool II, first introduced in FIG. 17A.

Using freshly prepared hetero-oligomers of WT+F12L, the Pool I and Pool II proteins were separated chromatographically and then dialyzed for 24 hours at pH 7 in the presence of 10 mM ALA. Following dialysis, the re-equilibrated hetero-oligomers were again separated into their hexameric and octameric components by chromatography on a Mono-Q column. The separated proteins were characterized for their specific activity and for their Phe12 and Leu12 content. The specific activity of hexamer and octamer are dramatically different with hexamer showing optimal activity at pH 9 and the activity of octamer is maximal at pH 7 (Table 4) [39]. A native gel of these proteins shows the relative distribution of octamer and hexamer in samples before dialysis and after Mono-Q chromatography (FIG. 26A). Following chromatographic separation, the proteins were called Pool I hexamer, Pool I octamer, Pool II hexamer, and Pool II octamer and are described below. The peak to elute first on the Mono-Q column runs comparably to the F12L mutant, which is the hexamer. The hexameric structure is substantiated by native gel electrophoresis and by specific activity at pH 7 and pH 9 (FIG. 26A and Table 4). The second peak to elute runs comparably to the WT human PBGS, which is the octamer. The octameric structure is substantiated by native gel electrophoresis and specific activity at pH 7 and pH 9 (FIG. 26A and Table 4). Consistent with the documented characteristics of human PBGS hexamers and octamers [39], Pool I hexamer and Pool II hexamer have very low activity at pH 7 and considerable activity at pH 9. Pool I octamer and Pool II octamer both show substantially higher activity at pH 7 than at pH 9.

Figure 26B:
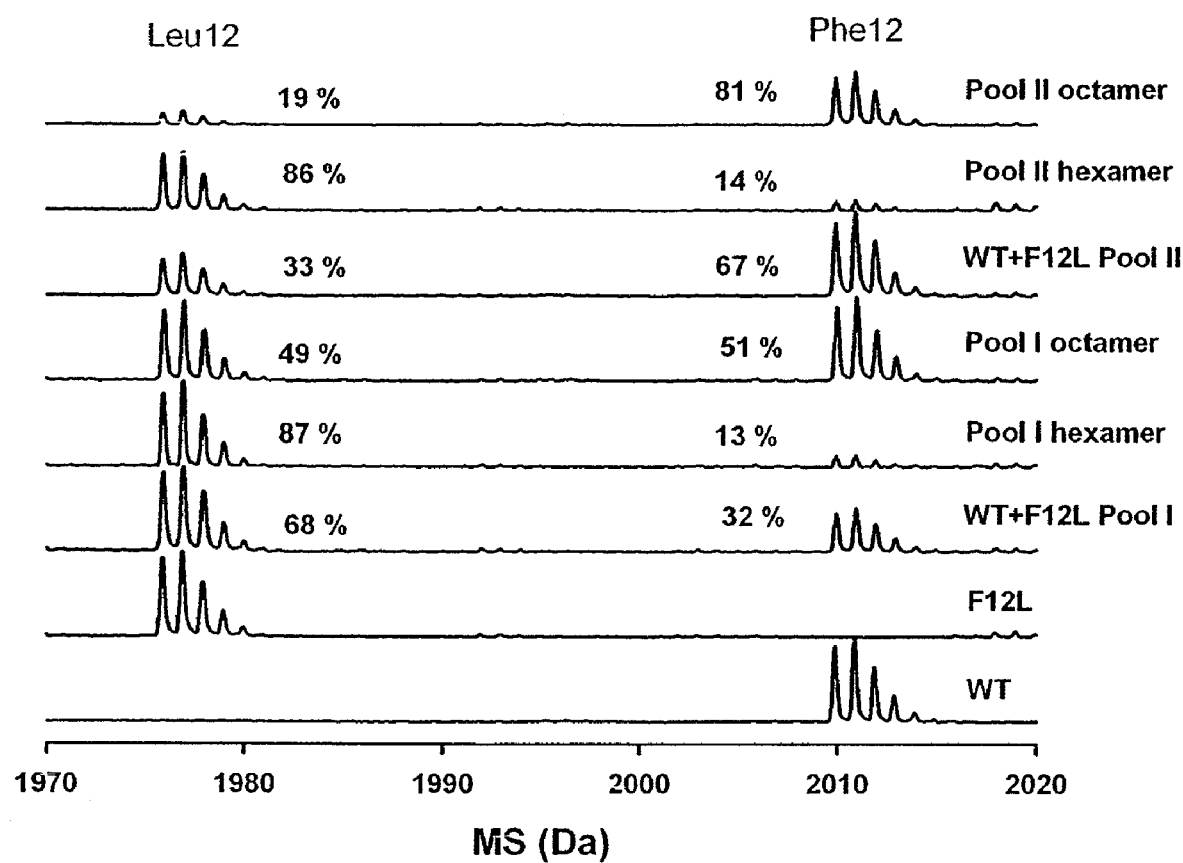
FIG. 26B shows mass spectral data for the N-terminal tryptic peptide of WT+F12L Pool I and WT+F12L Pool II before and after the disproportionation reaction and Mono-Q chromatography. WT and F12L are included as standards.

To address the hypothesis that hetero-oligomeric WT+F12L pools will disproportionate, resulting in accumulation of Phe12 in the octamer and Leu12 in the hexamer, the Phe12 and Leu12 content of the heteromeric PBGS oligomers was determined before dialysis and after Mono-Q chromatography. The proteins were subjected to tryptic digestion and the N-terminal peptide was analyzed by laser desorption mass spectroscopy. Prior work had established that this technique gives quantitative results that are comparable to those obtained by quantitative N-terminal sequencing for these two very similar peptides [39]. The mass of the N-terminal tryptic peptides are 2010.2 Da for the Phe12-containing peptide and 1976.2 Da for the Leu12-containing peptide (FIG. 26B). The data confirm that both Pool I and Pool II contain heteromeric species. The Pool I protein, initially a hetero-hexamer at a Phe:Leu ratio of 32:68, when dialyzed against ALA, yields the Pool I hexamer and a Pool I octamer of respective ratios 13:86 and 51:49. This demonstrates a dramatic disproportionation of the Leu-containing species to the hexamer and the Phe-containing species to the octamer. The dramatic change in the Phe:Leu ratio was also observed when the Pool II protein, initially at 67:32, was dialyzed against ALA. On native gel, Pool II shows a major octamer band and a light hexamer band (FIG. 26A). After 24 hours of dialysis in the presence of ALA, the Pool II octamer was enriched in Phe (Phe:Leu ratio of 81:19) and the small amount of remaining hexamer was enriched in Leu (Phe:Leu ratio of 14:86). The mass spectral data unequivocally establishes the disproportionation of heteromeric PBGS isoforms under turnover conditions. The mass spectral data also confirm that human PBGS with phenylalanine at position 12 prefers the octamer, which assembles from the hugging dimer, and protein with leucine at position 12 prefers the hexamer, which assembles from the detached dimer. It remains unclear whether the dynamic structural interconversion illustrated in FIG. 24 is further complicated by the dissociation of dimers into their component monomers. Such a re-equilibration of dimers could result in the disproportionation of a population of Phe+Leu dimers into Phe+Phe and Leu+Leu dimers.

Figure 27A:
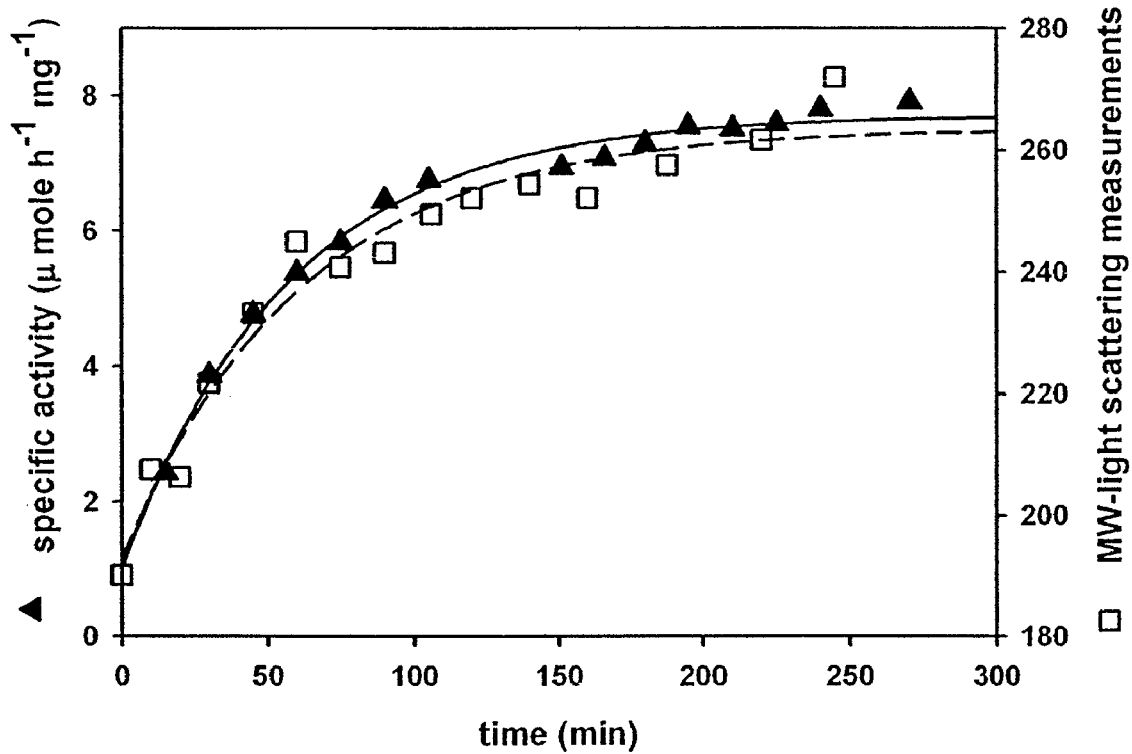
FIG. 27A illustrates the substrate induced dynamic interconversion (disproportionation) of WT+F12L hetero-hexamers (Pool I) to WT+F12L hetero-octamers at pH 7 by monitoring the increase in specific activity with time (▲) and the increase in molecular size by dynamic light scattering. Pools I is introduced in FIG. 17A.
Figure 27B:
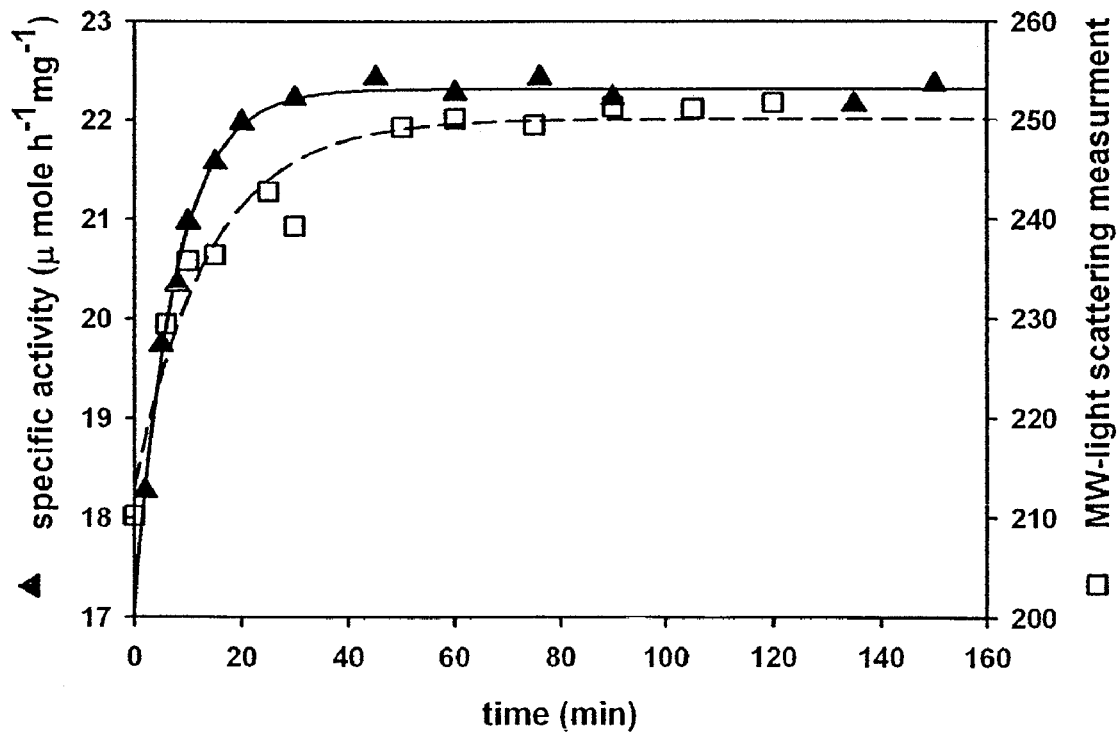
FIG. 27B is like FIG. 27A but starts with Pool II. Pool II is introduced in FIG. 17A.

It has been observed that dynamic interconversion of WT+F12L hetero-oligomeric PBGS quaternary structure isoforms is accompanied by an increase in activity at pH 7. Prior kinetic studies of PBGS showed that the dependence of activity on substrate concentration does not follow a simple hyperbolic Michaelis-Menten relationship (Tables 1 and 3). The kinetic data are best fit using a double hyperbolic equation, which is applicable to a model in which two enzymes of different kinetic parameters are catalyzing the same reaction [81]. The substrate induced structural interconversion (FIGS. 25A-C and 26A-C) and the resulting specific activity changes (Table 4) suggest that the heteromeric WT+F12L pools undergo structural rearrangement under assay conditions. Since substrate induced interconversion favors the octamer, which has increased activity at pH 7 relative to the hexamer, then the time course of product formation should show an increase in rate with time. This change is proposed to be most dramatic for Pool I (the heterologously expressed heterohexamer of WT+F12L) at pH 7, where the difference between the activities of octamer and hexamer is the greatest. As predicted, the specific activity of WT+F12L Pool I protein increases with time (FIG. 27A). The rate constant (1.05 h$^{-1}$) is based on fitting the data to an exponential rate equation and is about twice as fast as that determined from the equilibrium dialysis experiment (0.54 h$^{-1}$), qualitatively consistent with an expected delay caused by the time required for substrate and product to cross the dialysis membrane. Similar behavior was observed for WT+F12L pool II where the rate constant is 7.9 h$^{-1}$ (FIG. 27B).

Structural interconversion between hexamer and octamer not only has an effect on the protein's activity; it also alters the average molecular weight of protein. Using dynamic light scattering, the molecular weight change during the structural rearrangement of Pools I and II in the presence of substrate was monitored (FIGS. 27A-B). The light scattering data yield rate constants that are comparable to the rate constants from the time course activity assay (1.0 h$^{-1}$ for Pool I at pH 7, 5.0 h$^{-1}$ for Pool II), thus supporting the conclusion that the increase in activity is due to the interconversion of hexamer to octamer in the presence of substrate.

Light scattering was used as a method for monitoring the equilibration of quaternary structure isoforms. Light scattering has been used as a powerful tool for protein characterization, including purification monitoring [83], aggregation [84], assembly [85], structural stability [86], and crystal growth [87]. The current work is the first use of light scattering to monitor the molecular weight change due to the dynamic interconversion of quaternary structure isoforms of a homomeric protein. This demonstration opens possibilities for investigation of the kinetics of protein structure changes that in some cases could be very difficult to monitor by other spectroscopy techniques.

The dynamic interconversion of PBGS quaternary isoforms and the resulting disproportionation introduces the morpheein concept of quaternary structure equilibrium. The morpheein concept describes alternate quaternary structures of a protein with different functional characteristics, such as the octameric and hexameric forms of PBGS. The differences in oligomeric multiplicity, structure, and function result from a dramatic conformational change in the monomer. The interconversion and disporprotionation between heteromeric human PBGS morpheeins, as demonstrated herein, substantiates the reaction illustrated in FIG. 25.

TABLE 4

Specific activities ($\mu$mol h$^{-1}$ mg$^{-1}$) of hexameric and octameric forms of human PBGS before and after substrate induced disproportionation.

|  | F12L | WT | WT + F12L Pool I | WT + F12L Pool I | Pool I hexamer | Pool I octamer | Pool II hexamer | Pool II octamer |
|---|---|---|---|---|---|---|---|---|
| pH 7 | 0.3 | 56.9 | 7.9 | 21.8 | 0.5 | 11.5 | 0.2 | 17.6 |
| pH 9 | 14.5 | 13.1 | 6.6 | 5.4 | 5.8 | 6.8 | 1.6 | 5.7 |

Example 4

This example describes building the models for the hexameric morpheeins of *P. aeruginosa* PBGS and *R. capsulatus* PBGS.

The only existing crystal structure on which one can base a model of hexameric R capsulatus (or any other) PBGS is that of hexameric human PBGS clinical variant F12L, PDB code 1PV8 [39]. Unfortunately, the crystal structure of F12L shows significant disorder, which limits its use as the sole foundation for homology model building. However, comparison of human PBGS octameric and hexameric structures (PDB codes 1E51 and 1PV8) show near identity for the amino acids that comprise a TIM-like αβ-barrel domain. The differences between the octamer and the hexamer are in the 24 N-terminal amino acids and in the disordered regions [39]. Hence, one can use a higher quality crystal structure of a PBGS octamer for homology model building the αβ-barrel domain of *R. capsulatus* PBGS. The chosen structure is PDB code 1GZG [40], which is a highly ordered, high resolution crystal structure of *Pseudomonas aeruginosa* PBGS, and 56% sequence identical to *R. capsulatus* PBGS. The model building procedure was a two step process. The first step was construction of a model of a hexameric form of *P. aeruginosa* PBGS; the second step was to use that hexamer to build the *R. capsulatus* PBGS hexamer.

*P. aeruginosa* PBGS hexamer preparation used various capacities of the program Swiss-PDB Viewer [88] and some in-house programs. First, the N-terminal arms (amino acid numbers<32) were removed from the structure file for the 1 GZG dimer. The resulting αβ-barrel domains were successively overlaid upon the three diners of hexameric 1PV8 to create a hexameric assembly of *P. aeruginosa* PBGS αβ-barrels. There is no significant sequence identity between the N-terminal arms of human and *P. aeruginosa* PBGS, hence there is an alignment ambiguity when trying to build the outstretched arms of the *P. aeruginosa* PBGS hexamer. However, there is a region of the arm that is α-helical in both the human octamer and the human hexamer.

Hence, a structure alignment of octameric forms of human PBGS and *P. aeruginosa* PBGS was used to determine the proper sequence alignment for this α-helical segment. This information was used to spatially position the amino acids 22-29 of *P. aeruginosa* PBGS in the hexamer according to the position of this helix in the hexamer of human PBGS. Loop and side-chain prediction was performed in a graphical user environment [89], developed in the FCCC Molecular Modeling Facility, that integrates the functions of the programs Loopy [90], and SCWRL [91]. Within this environment, the program Loopy [90] was used to model the backbone of amino acids 29-32, so as to connect the N-terminal α-helix to the αβ-barrel domain of each subunit. The most N-terminal amino acids were built onto the structure within the Swiss-PDB viewer software using phi, psi, and omega angle information for the corresponding amino acids of hexameric human PBGS. Finally, the program SCWRL [91] was used to position the side chains for the N-terminal arm segments resulting in a model for hexameric *P. aeruginosa* PBGS, which could then be used for preparing hexameric models of other PBGS as has been done before for the octameric forms of pea and *D. melanogaster* PBGS [13,16]. The model for hexameric *R. capsulatus* PBGS was build using the same integrated graphical environment developed in house. This software integrates sequence alignment, threading, loop model building to accommodate insertions and deletions, and side chain optimization similar to that used for previously published models [13,16].

Example 5

Experimental Data with Rosmarinic Acid

Figure 22A:
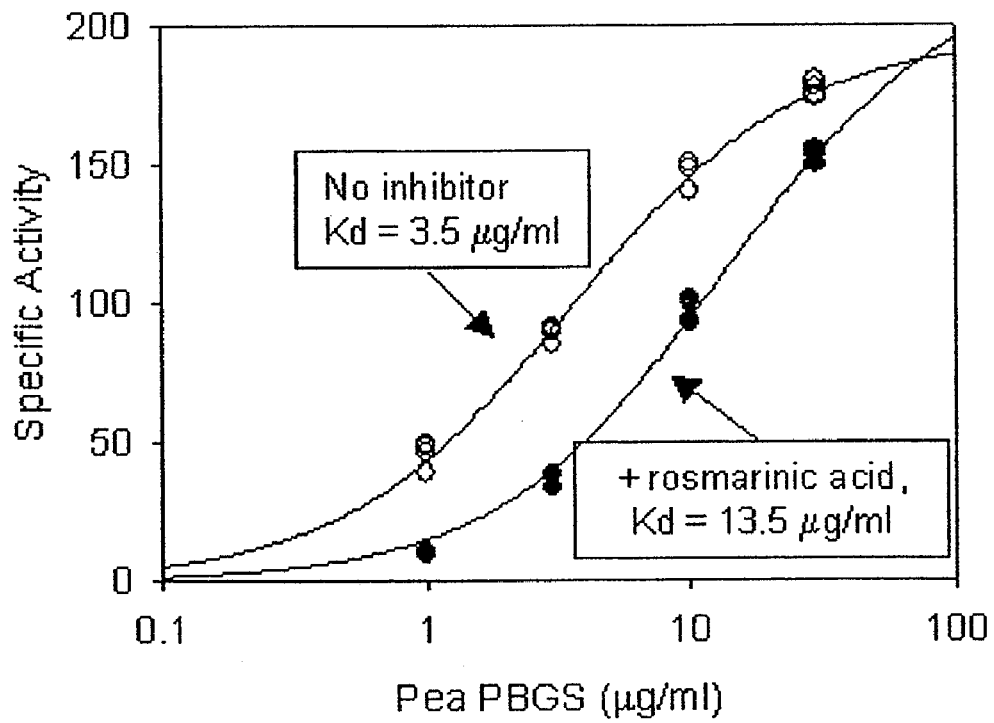
FIG. 22A shows the effect of rosmarinic acid on the protein concentration dependence of pea PBGS.
Figure 22B:
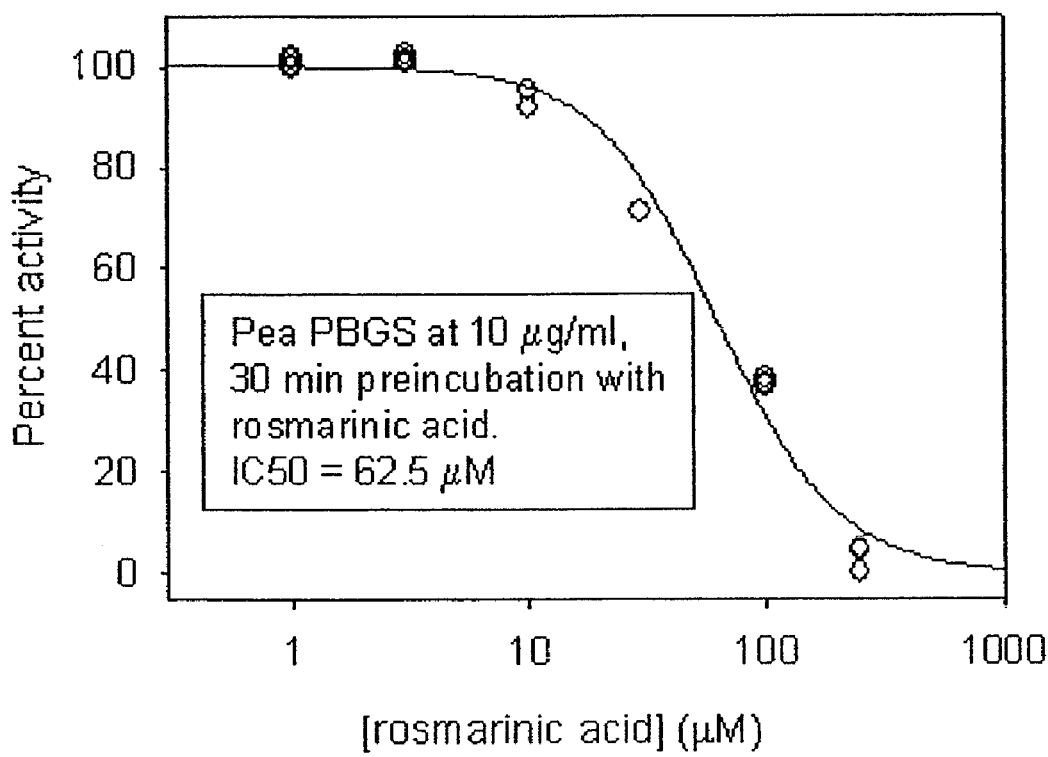
FIG. 22B shows a dose response curve for rosmarinic acid acting on pea PBGS.
Figure 22C:
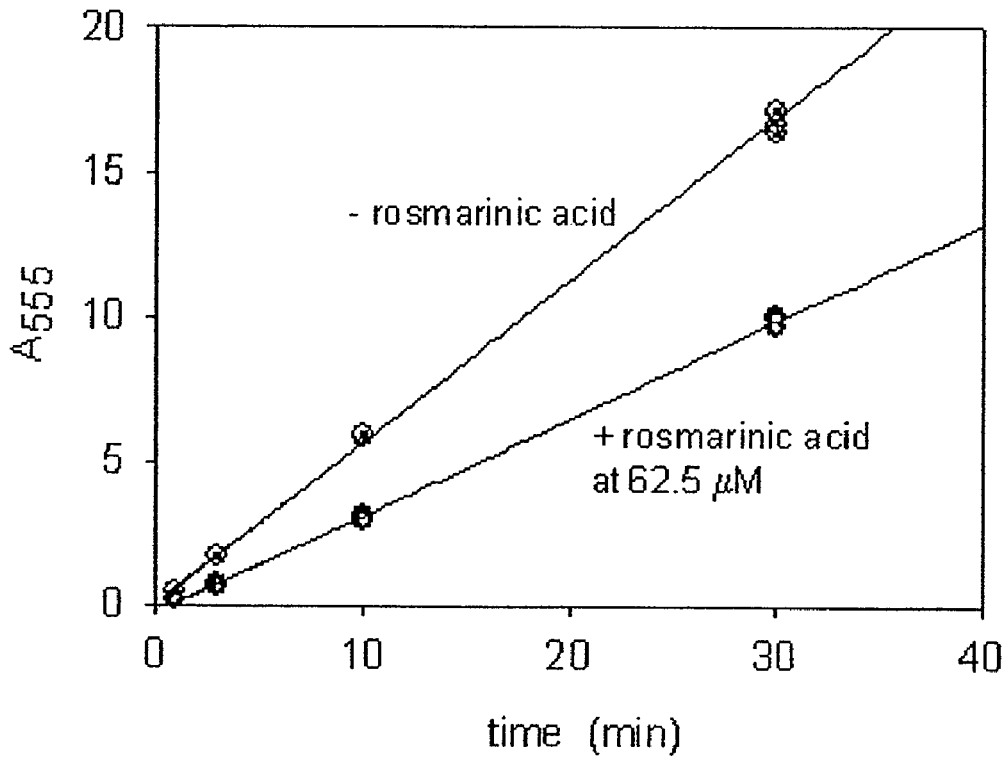
FIG. 22C shows that the enzyme catalyzed reaction rate is linear following treatment with rosmarinic acid.

Inhibition data with rosmarinic acid (benzenepropanoic acid, α-[[(2E)-3-(3,4-dihydroxyphenyl)-1-oxo-2-propenyl]oxy]-3,4-dihydroxy-, (αR)— (9CI)) is consistent with a slow-tight binding inhibition model wherein rosmarinic acid binds preferentially to the quaternary forms of pea PBGS that are smaller than the octamer. FIG. 22A, open symbols, illustrates the protein concentration dependence of the specific activity of pea PBGS, which shows half maximal activity at 3.5 µg/ml PBGS. This means that at 3.5 µg/ml (under assay conditions), the equilibrium of quaternary isoforms (morpheeins) contains about 50% octamer and about 50% smaller less active isoforms (e.g. hexamers). If an inhibitor acted through preferential binding to these smaller forms, one would expect a more profound inhibition under conditions where the morpheein equilibrium contains these smaller forms. In other words, the inhibitor would be expected to shift the protein concentration dependence to a higher protein concentration, which is shown for rosmarinic acid in FIG. 22A (see below). FIGS. 22B and 22C show experiments that were done to determine how best to demonstrate this shift in protein concentration dependence. FIG. 22B shows a dose response curve for pea PBGS, which indicates that the IC50 for rosmarinic acid is 63 µM, when the inhibitor is given 30 minutes to act on the protein prior to the addition of substrate. Not shown is the dependence of the inhibition on the preincubation time, where inhibition by any one concentration of rosmarinic acid increases with increasing preincubation time, showing that rosmarinic acid acts as a slow-binding inhibitor. FIG. 22C shows that once inhibition has taken place, the protein does not recover within a 30 minute assay time. The data obtained in FIGS. 22A, 22B, and 22C, were used to choose the appropriate conditions necessary to demonstrate the effect of rosmarinic acid on the protein concentration dependence of pea PBGS, as follows. The closed circles of FIG. 22A show the protein concentration dependence of the specific activity of pea PBGS following a 30 minute treatment with 30 µM rosmarinic acid, which results in half maximal activity at 13.5 µg/ml PBGS. Thus, following this treatment with rosmarinic acid, the equilibrium of quaternary forms has shifted from 3.5 µM to 13.5 µM; under these conditions it takes 13.5 µg/ml PBGS to obtain an equilibrium with 50% octamer. This is consistent with the interpretation that rosmarinic acid stabilizes the smaller, less active forms of PBGS, as illustrated schematically in by the balls in FIG. 13. FIGS. 23 A-B (described in detail below) support this conclusion with native gel electrophoresis data.

Figure 23A:
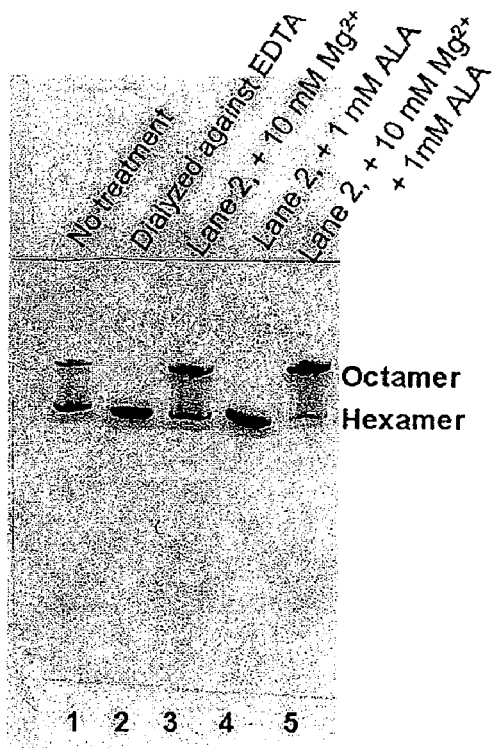
FIG. 23A shows the differential effects of various treatments on the morpheein equilibrium of pea PBGS, as analyzed by 12.5% acrylamide native gel electrophoresis. The protein is peaPBGS variant C326A, which has all the characteristics of the wild type protein. Lane 1—as purified; Lane 2—dialyzed against EDTA at low salt (10 mM BTP) to make the hexamer; Lane 3—hexameric pea PBGS (same as lane 2) treated with 10 mM magnesium, which helps to form the octamer from the hexamer; Lane 4—hexameric pea PBGS treated with ALA alone, which does not reform the octamer from the hexamer; Lane 5—hexameric pea PBGS treated with 10 mM magnesium and 1 mM ALA, which is more effective than magnesium alone at shifting the equilibrium toward the octamer.

FIG. 23A shows the effects of magnesium and ALA on the hexamer-octamer equilibrium of pea PBGS (variant C326A) [13]. Lane 1—Pea PBGS as purified runs as an octamer/hexamer mixture. Lane 2—hexameric pea PBGS can be prepared (from lane 1) by dialysis against 1 mM EDTA, 10 mM BTP. This suggests that magnesium stabilizes the octameric. Lane 3-hexameric pea PBGS, from lane 2, incubated with 10 mM $MgCl_2$. Magnesium, which is proposed to be the specific allosteric activator that stabilizes the octamer, indeed fills this role. Lane 4—hexameric pea PBGS, from lane 2, incubated with 1 mM ALA, does not run differently from lane 2. This is consistent with the data on the human protein which shows that the hexameric form does not bind ALA very well. Lane 5—hexameric incubated with both 10 mM $MgCl_2$ and 1 mM ALA. One can observe a dramatic conversion of the hexamer to the octamer under conditions where the protein is active and the equilibrium can be drawn toward the octamer. This, like all other incubations, was for 5 min at 37° C.

Figure 23B:
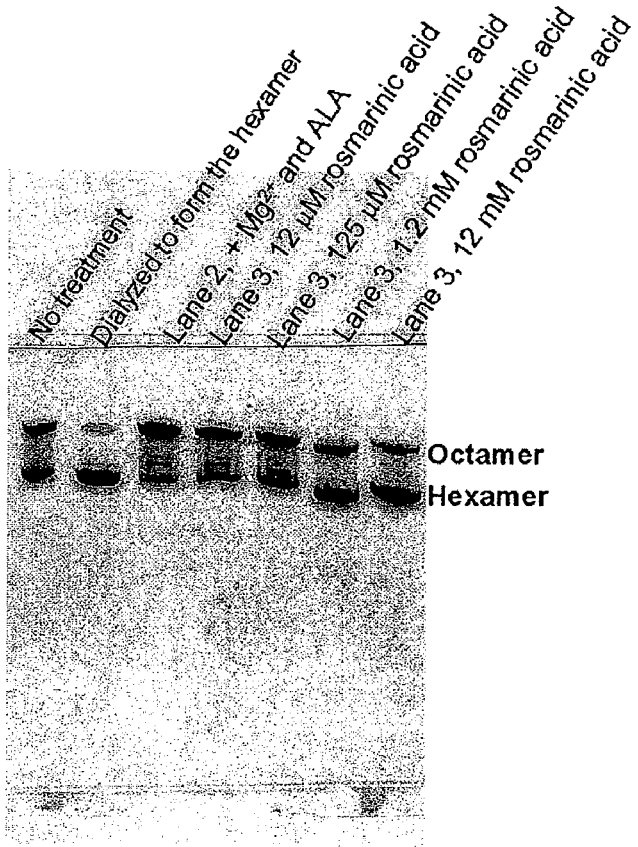
FIG. 23B shows that rosmarinic acid stabilizes the hexamer of pea PBGS C326A against conversion from hexamer to octamer. Lane 1—as purified; Lane 2—dialyzed against EDTA at low salt (10 mM BTP) to make the hexamer; Lane 3—hexameric pea PBGS (same as lane 2) preincubated at 37 C for 30 min followed by 5 min with 1 mM ALA and 1 mM MgCl$_2$, which shifts the equilibrium away from the hexamer and toward the octamer. Lane 4-7 like lane 3, but with the addition of rosmarinic acid in the preincubation mixture at 12.5 μM, 125 μM, 1.25 mM, and 12.5 mM rosmarinic acid. Increasing concentrations of rosmarinic acid are shown to prevent conversion of the hexamer to the octamer by magnesium and ALA.

FIG. 23B shows that rosmarinic acid stabilizes the hexameric pea PBGS against conversion to the octamer in the presence of ALA and magnesium. FIG. 23B is obtained using pea PBGS (C326A) under the following conditions: Lane 1—as purified; Lane 2—dialyzed to make the hexamer; Lane 3—hexameric pea PBGS (from lane 2) preincubated at 37 C for 30 min followed by 5 min with 1 mM ALA and 1 mM $MgCl_2$. Again this demonstrates how substrate plus magnesium causes conversion of the hexamer to the octamer; Lane 4-7 Like lane 3, but with the addition of rosmarinic acid in the preincubation mixture at 12.5 µM, 125 µM, 1.25 mM, and 12.5 mM rosmarinic acid.

Based on the inventor's modeling results, the interactions of this biphenyl compound (rosmarinic acid) with the "arm pit" of the pea PBGS hexamer are predominantly through hydrogen bonds between the protein subunits A, B, and E and the polar moieties of the rosmarinic acid. The protein contains additional hydrogen bonding potential within 4.0 angstroms of the rosmarinic acid. Hence, a derivative of the rosmarinic acid can be made to have an improved binding by adding additional hydrogen bonding potential to the rosmarinic acid molecule. For instance, one could add a hydroxyl group at the 5 position of either phenyl moiety and improve hydrogen bonding to the protein. Additional hydrophobic interactions with the protein could be obtained by substituting a phenyl or benzyl group at the 2 position of the propanoic acid portion of the molecule.

Example 6

A Prophetic Example

Inhibition of GDP-Mannose Dehydrogenase

Figure 29A:
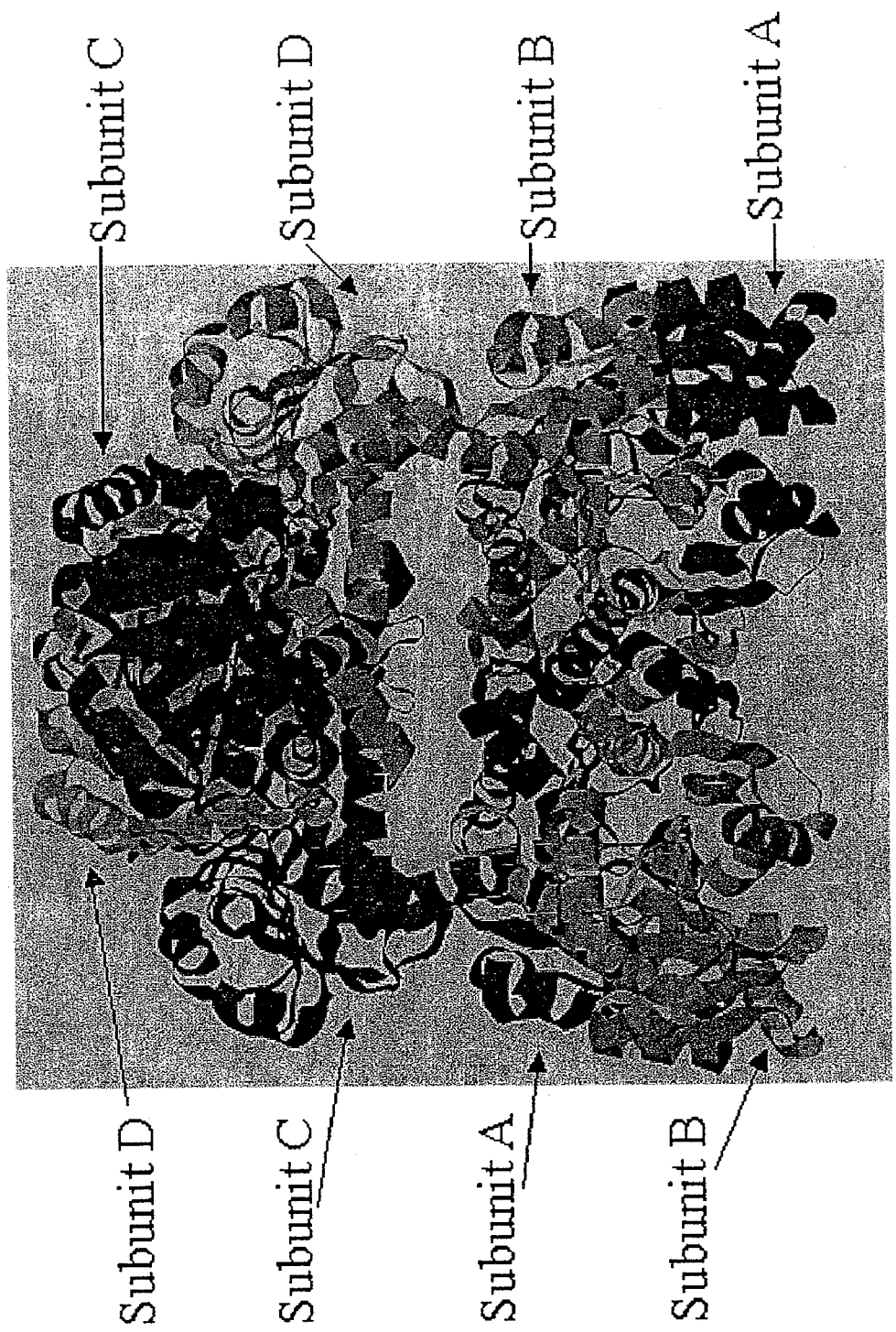
FIG. 29A is an illustration of the crystallographic asymmetric unit for *Pseudomonas aeruginosa* GDP-Mannose dehydrogenase, which is a tetramer [18]. The protein subunits are represented with ribbons, subunits A and C are in black, subunits B and D are in gray.

The alginates are a family of polysaccharides that exist in the cell walls of brown algae and in the capsular material (biofilm) that is laid down by some pathogenic *Pseudomonas* and *Azotobacter*. In the service of mankind alginate has been used as a wound dressing, but to the scourge of mankind the alginate laid down by pathogens provides a barrier against the host immune response and against antibiotics. Thus, inhibition of alginate biosynthesis is an attractive target for antibiotic development, particularly toward the antibiotic resistant *Pseudomonas aeruginosa* that have become ubiquitous hospital pathogens. *Pseudomonas aeruginosa* GDP-mannose dehydrogenase (GMD, EC 1.1.1.132) is a key regulatory enzyme in the biosynthesis of alginate [92]. The inventor proposes the existence of GMD morpheeins based published kinetic phenomena [19]. The specific activity is dependent upon the concentration of the enzyme and is dependent upon the order of addition of reaction components. Activity assays initiated by addition of enzyme show marked hysteresis, whereas assays of the same composition started by the addition of the NAD cofactor show a constant activity, suggesting that substrate initiates a re-equilibration of GMD morpheeins from a less active form to a more active form. Measurements of GMD size and cooperativity suggest that the catalytically active form is a hexamer, perhaps in equilibrium with a trimer [19]. However the published crystal structure (FIG. 29A) shows a tetramer made up of two loosely associated dimers [18]. In support of an active and an inactive form, it has been reported that GMD "interconverts readily" between two forms, which are a "cooperative" form with a low affinity for NAD but a higher $V_{max}$, and a "noncooperative" form with a high affinity for NAD but a lower $V_{max}$ [19,93]. The inventor proposes that the available crystal structure represents the low $V_{max}$ morpheein.

Figure 29B:
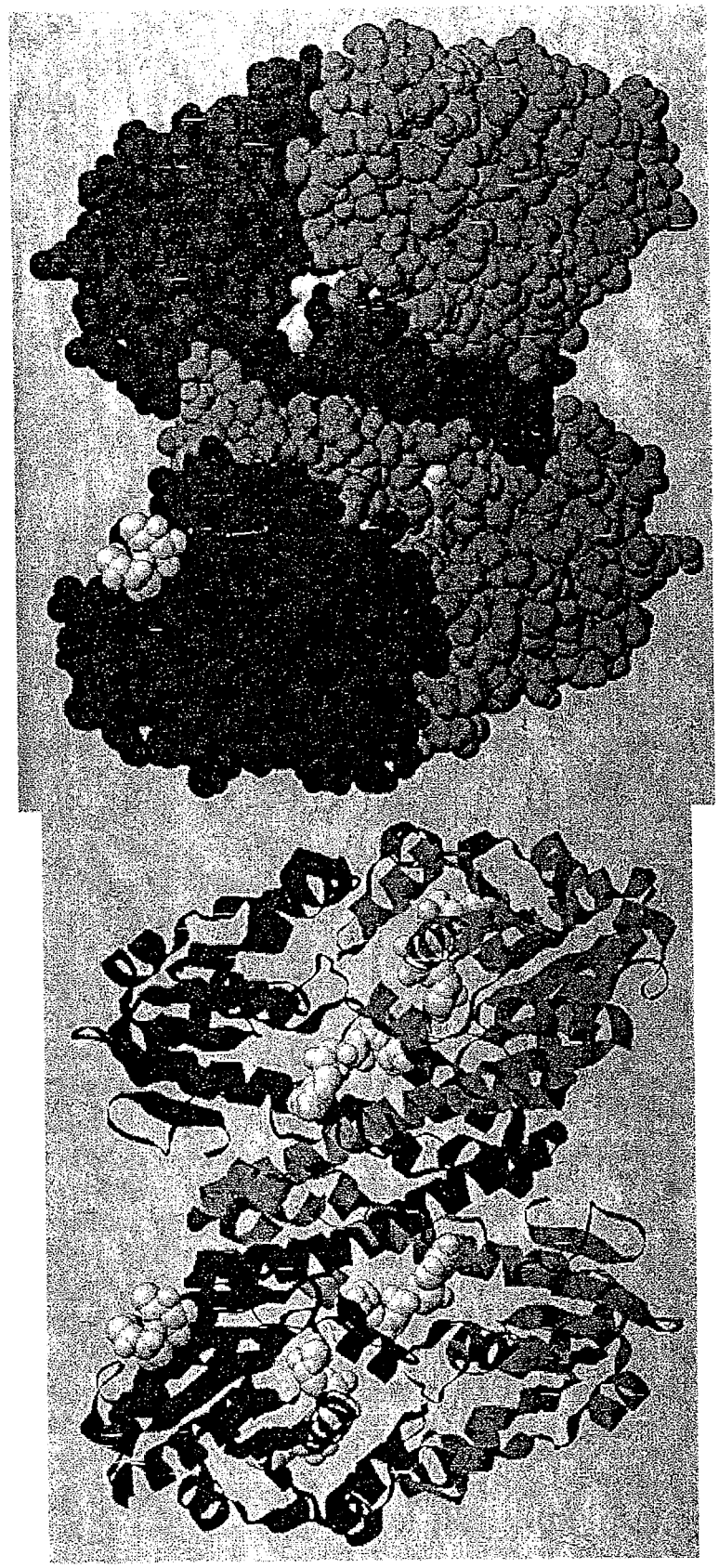
FIG. 29B is side view of the AB dimer, including enzyme-bound ligands in space filling representation, white. The illustration on the left uses ribbons to represent subunits A and B, while the illustration on the right uses a space filling representation. In the right hand illustration one can see how the active site ligand are buried.
Figure 29C:
FIG. 29C is a similar side view of the AB dimer, illustrating the large number of ordered water molecules that solvate the dimer interface.

The crystallographic tetramer of *pseudomonas aeruginosa* GDP-Mannose dehydrogenase (FIG. 29A, PDB code 1MV8) shows the intimate, almost pretzel-like relationship between subunits A and B or C and D, but the weak interaction between the AB and CD dimers. FIG. 29B shows a side view of the AB dimer, the left half uses a ribbon representation for the protein and a white space filling representation for the enzyme bound ligands. The right half uses a space filling representation for the protein as well. A comparison of the left and right halves shows how the active site ligands are located between subunits, and in fact are nearly buried between them. One can imagine that the protein might need to substantially reorient these subunits in order to release the ligands, which in the crystal structure are NAD and an analog of GDP-mannose. The inventor proposes that this dimer or tetramer is the low activity form that binds NAD very tightly and also proposes that it may be possible to trap this form to prevent formation of the active hexamer, whose structure remains unknown. In support of the notion that this structure can readily unravel are the large number of water molecules that lie at the subunit interfaces. FIG. 29C shows the water molecules (as white spheres) that are within 4.0 A of both subunits A and B.

Figure 29D:
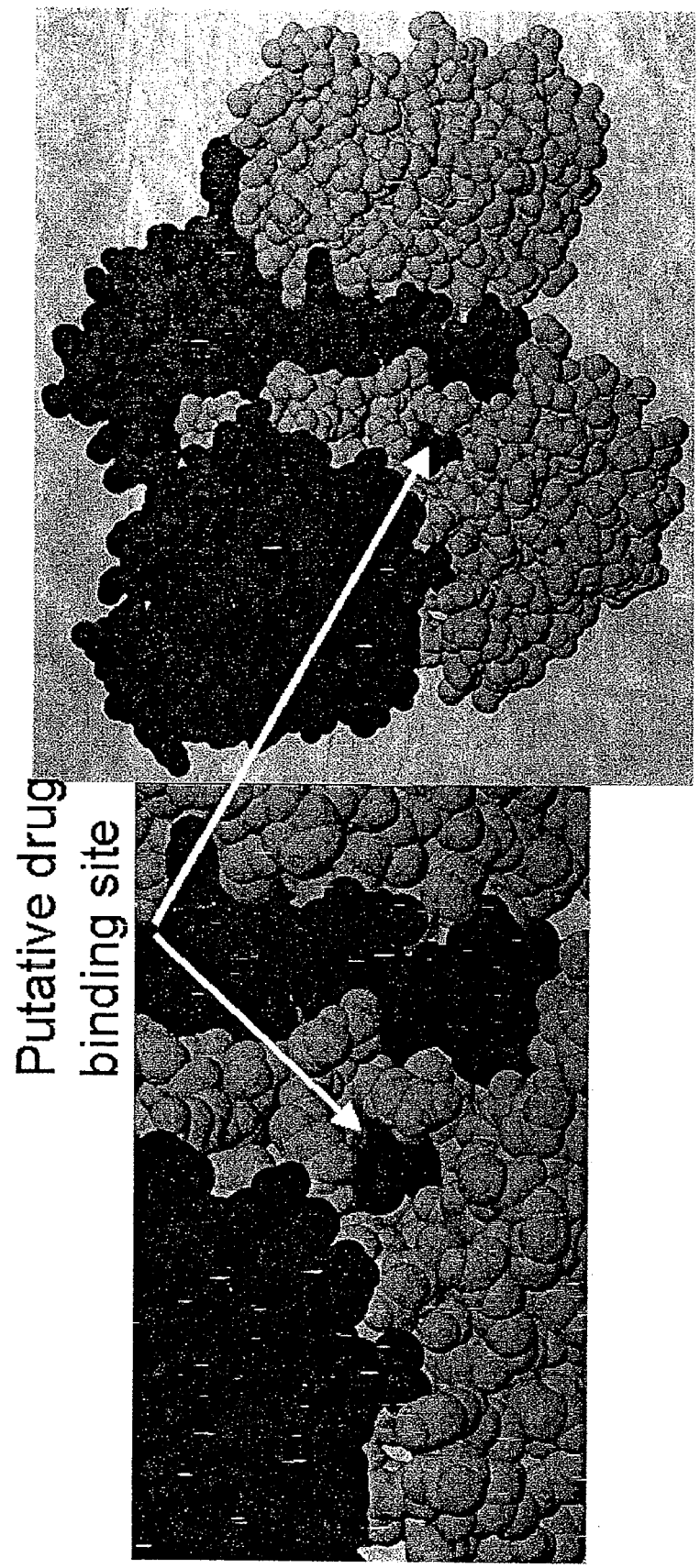
FIG. 29D uses a space filling representation of the side view of the AB dimer to show the surface cleft that is predicted as a putative drug binding site. This site is enlarged on the left.

The surface of the AB dimer of GMD has at least one deep pocket which can be targeted for drug discovery (FIG. 29D). This binding pocket is comprised of residues from both subunits and a ligand bound at this site would be expected to draw the morpheein equilibrium toward this putatively less active form. This example relies on the presumption that the intimately intertwined dimer must come apart and re-associate in order to form the more active hexameric morpheein. To test this hypothesis, the 1.6 A crystal structure of *Pseudomonas aeruginosa* GMD will be used, this pocket will be selected as the drug binding site, and the cited in silico methods will be used to dock compounds into this site. Hit molecules would then be tested for their ability to inhibit GMD in a way that effects the protein concentration dependence to the specific activity.

Example 7

A Prophetic Example

Locking the Bacterial Histidine Containing Phosphocarrier Protein Kinase/Phosphatase as the Phosphatase Active Oligomer The bifunctional HPr kinase/phosphatase (HPrK/P, EC 2.7.1.-/3.1.3.) of most gram-positive (and some gram negative) bacteria is involved in the regulation of carbon catabolite repression or activation. This complex regulatory pathway allows bacteria to adapt rapidly to environmental changes in carbon sources [20], thus ensuring their survival. The inventor proposes that HPrK/P exists as morpheeins for the following reasons. The complex kinetics of HPrK/P shows varying degrees of cooperativity dependent upon the reaction conditions. The crystal structures of HPrK/P from *Lactobacillis casei* [94], *Staphylococcus xylosis* [95] and *Mycoplasma pneumoniae* [96] all show a hexameric assembly composed of two trimers. Based on these crystal structures, it has been suggested that nucleotide binding would either involve an unusual configuration of the nucleotide, or that the protein would have to change its quaternary structure to accommodate the nucleotide [20]. Hence, this hexameric morpheein is proposed to be the one with phosphatase activity; this morpheein cannot be a kinase if it cannot bind the nucleotide. A detailed analysis of B. subtilis HPrK/P suggests a pH dependent structural equilibrium of monomers, dimers, and hexamers [97]; the lower oligomeric states, whose structures are unknown, are proposed to be the kinase active forms. The oligomeric structure equilibrium is affected by allosteric activators and substrates, which suggests that the oligomerization state is an important factor in the switch between kinase and phosphatase activity [97]. A tryptophan fluorescence study, which predated the crystal structure determinations, concluded that the enzyme exists as a heterogeneous population of oligomers, approximately a 50/50 mixture of two forms. One form contained the single tryptophan residue in a solvent exposed position and the other form contained the tryptophan in a position that was buried from solvent [98]. The inventor has mapped the unique tryptophan of B. subtilis HPrK/P onto the crystal structure of Lactobacillus casei HPrK/P (PDB code 1KKJ) and finds this tryptophan to be completely solvent exposed, (illustrated in FIG. 30) which is interpreted to reflect the population of oligomers (~50%) where tryptophan fluorescence was readily quenched by the addition of iodide. Because this tryptophan is on the surface of the hexamer, a simple dissociation of hexamer to trimers, dimers, or monomers would not change the solvent exposed character of the unique tryptophan. Hence, the kinase active form is proposed to involve an alternate morpheein configuration wherein this tryptophan is buried.

Figure 31:
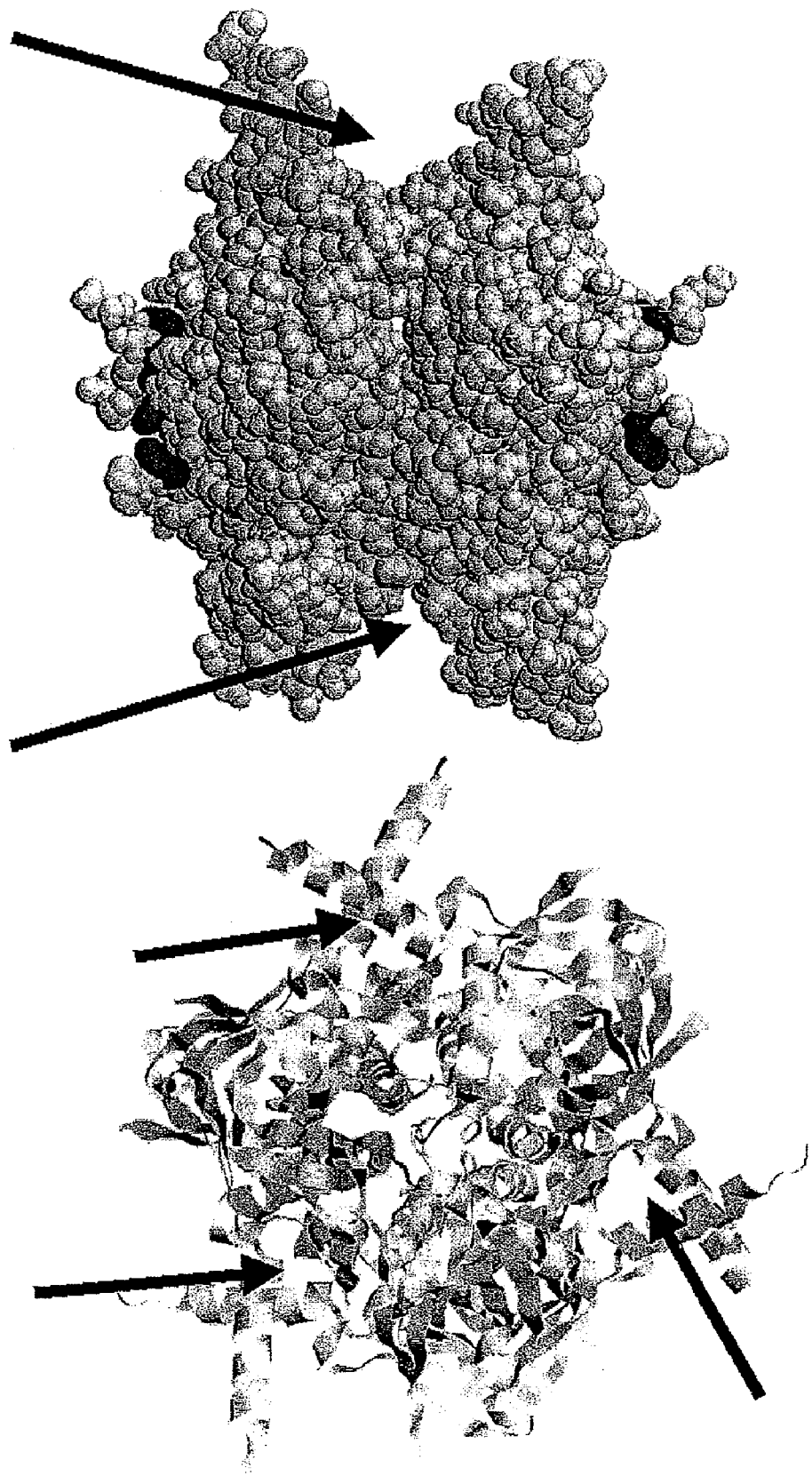
FIG. 31 illustrates the same two orientations of the crystal structure of *Lactobacillus casei* HPrK/P, in the hexameric assembly, without the HPr protein. The arrows depict an alternative drug binding site. The top illustration uses a space filling representation and the bottom uses a ribbon diagram.

Since there is no available crystal structure for the kinase active form of HPrK/P, the inventor suggests a rationale for trapping the phosphatase active hexameric form. When HPr is phosphorylated at Ser-46, it is capable of interacting with a carbon catabolite control protein. In the absence of this interaction, one could predict that the bacteria would not be capable of turning on the genes necessary for metabolizing the available carbon sources. Hence, one could argue that trapping HPrK/P in the hexameric assembly might act to inhibit bacterial cell growth, or to encourage the bacteria to enter a sporulation state. The L. casei structure, illustrated in FIG. 30 shows the three surface tryptophans forming the base of a unique surface binding site for a putative drug molecule that will trap this hexameric, putatively kinase inactive form of the protein. Surface tryptophan residues clustered such as these should form an excellent binding site, however the cleft is a shallow one. Furthermore, this tryptophan is not conserved in all HPrK/P from pathogenic organisms. FIG. 31 illustrates an alternative cleft in the hexameric assembly of HPrK/P, which is a deep surface cleft and is expected to be a common structure (if not a common sequence) for all the HPrK/P proteins.

While the invention has been described in detail and with reference to specific examples thereof, it will be apparent to one skilled in the art that various changes and modifications can be made therein without departing from the spirit and scope thereof.

REFERENCES

1 Anfinsen, C. B. (1973) Principles that govern the folding of protein chains. *Science* 181 (96), 223-230

2 Caspar, D. L. and Klug, A. (1962) Physical principles in the construction of regular viruses. *Cold Spring Harb Symp Quant Biol* 27, 1-24

3 Morgan, G. J. (2003) Historical review: viruses, crystals and geodesic domes. *Trends Biochem Sci* 28 (2), 86-90

4 Koshland, D. E., Jr. et al. (1966) Comparison of experimental binding data and theoretical models in proteins containing subunits. *Biochemistry* 5 (1), 365-385

5 Monod, J. et al. (1965) On the Nature of Allosteric Transitions: A Plausible Model. *J Mol Biol* 12, 88-118

6 Jordan, P. M. (1994) Highlights in haem biosynthesis. *Curr Opin Struct Biol* 4 (6), 902-911

7 Battersby, A. R. and Leeper, F. J. (1997) Biosynthesis of vitamin B12. *Topics in Current Chemistry* 195(Biosynthesis: Polyketides and Vitamins), 143-193

8 Battersby, A. R. (2000) Tetrapyrroles: the pigments of life. *Nat Prod Rep* 17 (6), 507-526

9 Jaffe, E. K. (2000) The porphobilinogen synthase family of metalloenzymes. *Acta Crystallogr D Biol Crystallogr* 56 (Pt 2), 115-128

10 Berman, H. M. et al. (2000) The Protein Data Bank. *Nucleic Acids Res* 28 (1), 235-242

11 Jaffe, E. K. (2003) An unusual phylogenetic variation in the metal ion binding sites of porphobilinogen synthase. *Chem Biol* 10 (1), 25-34

12 Jaffe, E. K. and Hanes, D. (1986) Dissection of the early steps in the porphobilinogen synthase catalyzed reaction. Requirements for Schiff's base formation. *J Biol Chem* 261 (20), 9348-9353

13 Kervinen, J. et al. (2000) Porphobilinogen synthase from pea: expression from an artificial gene, kinetic characterization, and novel implications for subunit interactions. *Biochemistry* 39 (30), 9018-9029

14 Petrovich, R. M. et al. (1996) *Bradyrhizobium japonicum* porphobilinogen synthase uses two Mg(II) and monovalent cations. *J Biol Chem* 271 (15), 8692-8699

15 Bollivar, D. W. et al. (2004) *Rhodobacter capsulatus* porphobilinogen synthase, a high activity metal ion independent hexamer. *BMC Biochem* 5 (1), 17

16 Kundrat, L. et al. (2003) A structural basis for half-of-the-sites metal binding revealed in *Drosophila melanogaster* porphobilinogen synthase. *J. Biol. Chem.* 278 (33), 31325-31330

17 Bevan, D. R. et al. (1980) Mechanism of porphobilinogen synthase. Requirement of Zn2+ for enzyme activity. *J Biol Chem* 255 (5), 2030-2035

18 Snook, C. F. et al. (2003) Crystal structure of GDP-mannose dehydrogenase: a key enzyme of alginate biosynthesis in *P. aeruginosa*. *Biochemistry* 42 (16), 4658-4668

19 Naught, L. E. et al. (2002) Allosterism and cooperativity in *Pseudomonas aeruginosa* GDP-mannose dehydrogenase. *Biochemistry* 41 (30), 9637-9645

20 Poncet, S. et al. (2004) HPr kinase/phosphorylase, a Walker motif A-containing bifunctional sensor enzyme controlling catabolite repression in Gram-positive bacteria. *Biochim Biophys Acta* 1697 (1-2), 123-135

21 Rochet, J. C. et al. (2000) Pig heart CoA transferase exists as two oligomeric forms separated by a large kinetic barrier. *Biochemistry* 39 (37), 11291-11302

22 Bzowska, A. et al. (1995) Calf spleen purine nucleoside phosphorylase: purification, sequence and crystal structure of its complex with an N(7)-acycloguanosine inhibitor. *FEBS Lett* 367 (3), 214-218

23 Koellner, G. et al. (1998) Crystal structure of the ternary complex of *E. coli* purine nucleoside phosphorylase with formycin B, a structural analogue of the substrate inosine, and phosphate (Sulphate) at 2.1 A resolution. *J Mol Biol* 280 (1), 153-166

24 Poole, L. B. (2005) Bacterial defenses against oxidants: mechanistic features of cysteine-based peroxidases and their flavoprotein reductases. *Arch Biochem Biophys* 433 (1), 240-254

25 Wood, Z. A. et al. (2002) Dimers to doughnuts: redox-sensitive oligomerization of 2-cysteine peroxiredoxins. *Biochemistry* 41 (17), 5493-5504

26 Akagi, R. et al. (1999) A novel mutation of delta-aminolaevulinate dehydratase in a healthy child with 12% erythrocyte enzyme activity. *Br J Haematol* 106 (4), 931-937

27 Maruno, M. et al. (2001) Highly heterogeneous nature of delta-aminolevulinate dehydratase (ALAD) deficiencies in ALAD porphyria. *Blood* 97 (10), 2972-2978

28 Jaffe, E. K. (2004) The porphobilinogen synthase catalyzed reaction mechanism. *Bioorg Chem* 32 (5), 316-325

29 Frankenberg, N. et al. (1999) High resolution crystal structure of a Mg2+-dependent porphobilinogen synthase. *J Mol Biol* 289 (3), 591-602

30 Kervinen, J. et al. (2001) Mechanistic basis for suicide inactivation of porphobilinogen synthase by 4,7-dioxosebacic acid, an inhibitor that shows dramatic species selectivity. *Biochemistry* 40 (28), 8227-8236

31 Jaffe, E. K. et al. (1995) Characterization of the role of the stimulatory magnesium of *Escherichia coli* porphobilinogen synthase. *Biochemistry* 34 (1), 244-251

32 Frankenberg, N. et al. (1999) Production, purification, and characterization of a Mg2+-responsive porphobilinogen synthase from *Pseudomonas aeruginosa*. *Biochemistry* 38 (42), 13968-13975

33 Schneider, H. A. (1976) Enzymic capacities for chlorophyll biosynthesis. Activation and de novo synthesis of enzymes. *Z Naturforsch [C]* 31 (1-2), 55-63

34 Papenbrock, J. et al. (2000) Role of magnesium chelatase activity in the early steps of the tetrapyrrole biosynthetic pathway. *Plant Physiol* 122 (4), 1161-1169

35 Papenbrock, J. and Grimm, B. (2001) Regulatory network of tetrapyrrole biosynthesis—studies of intracellular signalling involved in metabolic and developmental control of plastids. *Planta* 213 (5), 667-681

36 Walker, D. A. (1976) Regulatory mechanisms in photosynthetic carbon metabolism. *Curr Top Cell Regul* 11, 203-241

37 Stolz, M. and Dornemann, D. (1996) Purification, metal cofactor, N-terminal sequence and subunit composition of a 5-aminolevulinic acid dehydratase from the unicellular green alga Scenedesmus obliquus, mutant C-2A'. *Eur J Biochem* 236 (2), 600-608

38 Tamai, H. et al. (1979) *Plant Cell Physiol*. 20, 435-444

39 Breinig, S. et al. (2003) Control of tetrapyrrole biosynthesis by alternate quaternary forms of porphobilinogen synthase. *Nat. Struct. Biol.* 10, 757-763

40 Frere, F. et al. (2002) Structure of porphobilinogen synthase from *Pseudomonas aeruginosa* in complex with 5-fluorolevulinic acid suggests a double Schiff base mechanism. *J Mol Biol* 320 (2), 237-247

41 Xiang, Z. et al. (2002) Evaluating conformational free energies: the colony energy and its application to the problem of loop prediction. *Proc. Natl. Acad. Sci. US* 99, 7432-7437

42 Friesner, R. A. et al. (2004) Glide: a new approach for rapid, accurate docking and scoring. 1. Method and assessment of docking accuracy. *J Med Chem* 47 (7), 1739-1749

43 Halgren, T. A. et al. (2004) Glide: a new approach for rapid, accurate docking and scoring. 2. Enrichment factors in database screening. *J Med Chem* 47 (7), 1750-1759

44 Cooperman, B. S. and Kashlan, O. B. (2003) A comprehensive model for the allosteric regulation of Class Ia ribonucleotide reductases. *Adv Enzyme Regul* 43, 167-182

45 Dhanasekaran, S. et al. (2004) Delta-aminolevulinic acid dehydratase from *Plasmodium falciparum*: indigenous versus imported. *J Biol Chem* 279 (8), 6934-6942

46 Irwin, J. J. and Shoichet, B. K. (2005) ZINC—a free database of commercially available compounds for virtual screening. *J Chem Inf Model* 45 (1), 177-182

47 Shimizu-Sato, S. et al. (2002) A light-switchable gene promoter system. *Nat Biotechnol* 20 (10), 1041-1044

48 Eichholtz, D. A. et al. (1994) Glyphosate-tolerant 5-enolpyruvyl-3-phosphoshikimate synthases. Monsanto Company (St. Louis, Mo.)

49 Daniell, H. et al. (1998) Containment of herbicide resistance through genetic engineering of the chloroplast genome. *Nat. Biotechnol.* 16 (4), 345-348

50 Suzuki, M. et al. (1994) Isolation and characterization of two tightly linked catalase genes from castor bean that are differentially regulated. *Plant Mol. Biol.* 25 (3), 507-516

51 Potrykus, I. et al. (1985) Molecular and general genetics of a hybrid foreign gene introduced into tobacco by direct gene transfer. *Mol. Gen. Genet.* 199 (2), 169-177

52 Hinchee, M. A. et al. (1988) Production of transgenic soybean plants using *Agrobacterium*-mediated DNA transfer. *Bio/Technology* 6, 915-922

53 Stalker, D. M. et al. (1988) Purification and properties of a nitrilase specific for the herbicide bromoxynil and corresponding nucleotide sequence analysis of the bxn gene. *J. Biol. Chem.* 263 (13), 6310-6314

54 (1985)

55 Thillet, J. et al. (1988) Site-directed mutagenesis of mouse dihydrofolate reductase. Mutants with increased resistance to methotrexate and trimethoprim. *J. Biol. Chem.* 263 (25), 12500-12508

56 Herrera-Estrella, L. et al. (1983) Expression of chimaeric genes transferred into plant cells using a Ti-plasmid-derived vector. *Nature* 303, 209-213

57 Bevan, M. (1984) Binary Arobacterium vectors for plant transformation. *Nucleic Acids Res.* 12 (22), 8711-8721

58 Klee, H. J. et al. (1985) Vectors for transformation of higher plants. *Bio/Technology* 3, 637-642

59 PCT Publication WO 93/19189.

60 Fraley, R. T. et al. (1983) Expression of bacterial genes in plant cells. *Proc. Natl. Acad. Sci. USA* 80 (15), 4803-4807

61 Rogers, S. G. et al. (1987) *Improved vectors for plant transformation: expression cassette vectors and new selectable markers*, San Diego: Academic Press 62 Schmidhauser, T. J. and Helinski, D. R. (1985) Regions of broad-host-range plasmid RK2 involved in replication and stable maintenance in nine species of Gram-negative bacteria. *J. Bacteriol.* 164, 446-455

63 Horsch, R. B. and Klee, H. J. (1986) Rapid assay of foreign gene expression in leaf discs transformed by *agrobacterium tumefaciens*: Role of T-DNA borders in the transfer process. *Proc. Natl. Acad. Sci. USA* 83 (12), 4428-4432

64 Hayashimoto, A. et al. (1990) A polyethylene glycol-mediated protoplast transformation system for production of fertile transgenic rice plants. *Plant Physiol*. 93, 857-863

65 Datta, S. K. et al. (1990) Genetically engineered fertile indica rice recovered from protoplasts. *Bio/Technology* 8, 736-740

66 Vasil, V. et al. (1992) Herbicide resistant fertile transgenic wheat plants obtained by microprojectile bombardment of regenerable embryogenic callus. *Bio/Technology* 10, 667-674

67 Vasil, V. et al. (1990) Regeneration of plants from embryogenic suspension culture protoplasts of wheats (*Triticum aestivum* L.). *Bio/Technology* 8, 429-434

68 Fromm, M. (1990) In *UCLA Symposium on Molecular Strategies for Crop Improvement*

69 Wetmur, J. G. et al. (1986) Human delta-aminolevulinate dehydratase: nucleotide sequence of a full-length cDNA clone. *Proc Natl Acad Sci USA* 83 (20), 7703-7707

70 Jaffe, E. K. et al. (2001) The molecular mechanism of lead inhibition of human porphobilinogen synthase. *J Biol Chem* 276 (2), 1531-1537

71 Laue, T. et al. (1992) In *Analytical Ultracentrifugation in Biochemistry and Polymer Science* (Harding, S. et al., eds.), pp. 90-125, The Royal Society 72 Frankenberg, N. et al. (1999) *Pseudomonas aeruginosa* contains a novel type V porphobilinogen synthase with no required catalytic metal ions. *Biochemistry* 38 (42), 13976-13982

73 Erskine, P. T. et al. (1997) X-ray structure of 5-aminolaevulinate dehydratase, a hybrid aldolase. *Nat Struct Biol* 4 (12), 1025-1031

74 Erskine, P. T. et al. (1999) X-ray structure of 5-aminolevulinic acid dehydratase from *Escherichia coli* complexed with the inhibitor levulinic acid at 2.0 A resolution. *Biochemistry* 38 (14), 4266-4276

75 Erskine, P. T. et al. (1999) The Schiff base complex of yeast 5-aminolaevulinic acid dehydratase with laevulinic acid. *Protein Sci* 8 (6), 1250-1256

76 Erskine, P. T. et al. (2000) MAD analyses of yeast 5-aminolaevulinate dehydratase: their use in structure determination and in defining the metal-binding sites. *Acta Crystallogr D Biol Crystallogr* 56 (Pt 4), 421-430

77 Erskine, P. T. et al. (2001) The X-ray structure of yeast 5-aminolaevulinic acid dehydratase complexed with two diacid inhibitors. *FEBS Lett* 503 (2-3), 196-200

78 Erskine, P. T. et al. (2001) The x-ray structure of yeast 5-aminolaevulinic acid dehydratase complexed with substrate and three inhibitors. *J Mol Biol* 312 (1), 133-141

79 Jaffe, E. K. et al. (2002) Species-specific inhibition of porphobilinogen synthase by 4-oxosebacic acid. *J Biol Chem* 277 (22), 19792-19799

80 Murzin, A. G. et al. (1995) SCOP: a structural classification of proteins database for the investigation of sequences and structures. *J Mol Biol* 247 (4), 536-540

81 Segel, I. (1975) *Enzyme Kinetics*, John Wiley and Sons, Inc 82 van Holde, K. E. et al. (1998) *Principles of Physical Biochemistry*, Prentice-Hall, Englewood Cliffs, N.J.

83 Schonfeld, H. J. et al. (1998) Quasi-elastic light scattering and analytical ultracentrifugation are indispensable tools for the purification and characterization of recombinant proteins. *Biochem. Soc. Trans.* 26 (4), 753-758

84 Wu, H. et al. (1997) Dimeric association and segmental variability in the structure of human CD4. *Nature* 387 (6632), 527-530

85 Moradian-Oldak, J. et al. (1998) Temperature and pH-dependent supramolecular self-assembly of amelogenin molecules: a dynamic light-scattering analysis. *J. Struct. Biol.* 122 (3), 320-327

86 Gast, K. et al. (1997) Ribonuclease Ti has different dimensions in the thermally and chemically denatured states: a dynamic light scattering study. *FEBS Lett.* 403 (3), 245-248

87 Ferre-D'Amare, A. R. and Burley, S. K. (1997) Dynamic light scattering in evaluation crystallizability of macromolecules. *Methods Enzymol.* 276, 157-166

88 Kaplan, W. and Littlejohn, T. G. (2001) Swiss-PDB Viewer (Deep View). *Brief Bioinform* 2 (2), 195-197

89 Canutescu, A. A. and Dunbrack, R. L., Jr. (2005) MolIDE (Molecular Integrated Development Environment): a homology modeling framework you can click with. *Bioinformatics*

90 Xiang, Z. et al. (2002) Evaluating conformational free energies: the colony energy and its application to the problem of loop prediction. *Proc Natl Acad Sci USA* 99 (11), 7432-7437

91 Canutescu, A. A. et al. (2003) A graph-theory algorithm for rapid protein side-chain prediction. *Protein Sci* 12 (9), 2001-2014

92 Shankar, S. et al. (1995) Exopolysaccharide alginate synthesis in *Pseudomonas aeruginosa*: enzymology and regulation of gene expression. *Adv Enzymol Relat Areas Mol Biol* 70, 221-255

93 Roychoudhury, S. et al. (1989) Purification and characterization of guanosine diphospho-D-mannose dehydrogenase. A key enzyme in the biosynthesis of alginate by *Pseudomonas aeruginosa*. *J Biol Chem* 264 (16), 9380-9385

94 Fieulaine, S. et al. (2001) X-ray structure of HBr kinase: a bacterial protein kinase with a P-loop nucleotide-binding domain. *Embo J* 20 (15), 3917-3927

95 Marquez, J. A. et al. (2002) Structure of the full-length HPr kinase/phosphatase from *Staphylococcus xylosus* at 1.95 A resolution: Mimicking the product/substrate of the phospho transfer reactions. *Proc Natl Acad Sci USA* 99 (6), 3458-3463

96 Allen, G. S. et al. (2003) Crystal structure of HPr kinase/phosphatase from *Mycoplasma pneumoniae*. *J Mol Biol* 326 (4), 1203-1217

97 Ramstrom, H. et al. (2003) Properties and regulation of the bifunctional enzyme HPr kinase/phosphatase in *Bacillus subtilis*. *J Biol Chem* 278 (2), 1174-1185

98 Jault, J. M. et al. (2000) The HPr kinase from *Bacillus subtilis* is a homo-oligomeric enzyme which exhibits strong positive cooperativity for nucleotide and fructose 1,6-bisphosphate binding. *J Biol Chem* 275 (3), 1773-1780

What is claimed is:

1. A method of inhibiting a multimeric porphobilinogen synthase from forming an active form, the method comprising: applying a composition comprising an inhibitor adapted to inhibit formation of an active form of a multimeric porphobilinogen synthase to the multimeric porphobilinogen synthase; associating the composition with the less active form of the multimeric porphobilinogen synthase; inhibiting the less active form from assembling into the active form and thereby inhibiting the multimeric porphobilinogen synthase from forming the active form.

2. A method of inhibiting a multimeric protein comprising an equilibrium of assembly states, each assembly having a plurality of units, wherein each of said units comprises a first complementary surface and a second complementary surface and wherein the first complementary surface of one unit is associated with the second complementary surface of another unit, provided that the assembly is at least one of different quaternary isoforms on condition that:
   (1) one conformation of said units determines a first quaternary isoform but does not allow formation of other quaternary isoforms;
   (2) a different conformation of said units determines one of a different quaternary isoforms, but does not allow formation of the first quaternary isoform;
   (3) the different conformations of said units are in an equilibrium; and
   (4) the conformation of said different quaternary isoforms influences a function of said multimeric protein, the method comprising:

applying to the multimeric protein a composition comprising an inhibitor adapted to inhibit formation of an active form of the multimeric protein;

associating the composition with a less active form of the multimeric protein;

inhibiting the less active form from assembling into the active form and thereby inhibiting the multimeric protein from forming the active form, wherein said multimeric protein is a member selected from the group consisting of porphobilinogen synthase, a Class Ia ribonucleotide reductase, Pseudomonas aeruginosa GDP- Mannose dehydrogenase, Bacillus subtilis HPr, mammalian CoA transferase, purine nucleoside phosphorylase, and peroxiredoxins.

3. The method of claim 2, wherein the unit is a member selected from the group consisting of a monomer, a dimer, a trimer, a tetramer, a pentamer, a hexamer, a heptamer, an octamer, and a decamer.

4. The method of claim 2, wherein said multimeric protein is porphobilinogen synthase comprising eight porphobilinogen synthase monomers.

* * * * *

UNITED STATES PATENT AND TRADEMARK OFFICE
CERTIFICATE OF CORRECTION

PATENT NO.       : 7,863,029 B2                                    Page 1 of 1
APPLICATION NO.  : 12/106498
DATED            : January 4, 2011
INVENTOR(S)      : Eileen K. Jaffe It is certified that error appears in the above-identified patent and that said Letters Patent is hereby corrected as shown below:

In col. 116, lines 15-16, replace "Bacillus subtilis HPr"

with

"Bacillus subtilis HPr kinase/phosphatase"

Signed and Sealed this
Fourteenth Day of August, 2012

David J. Kappos
*Director of the United States Patent and Trademark Office*

SEQUENCE LISTING

```
<160> NUMBER OF SEQ ID NOS: 135

<210> SEQ ID NO 1
<211> LENGTH: 3142
<212> TYPE: DNA
<213> ORGANISM: Homo sapiens

<400> SEQUENCE: 1
cttacgcggt ctgtgggaga ccggagcggg agacagcggt gacaggagca gcggccggga    60
```

| | |
|---|---|
| gcccttaggg aggcagacag agcctgcagc caatgcccca ggagccctcg gttccaacca | 120 |
| actgatgccc ctgtgcccac tggcccacgc catgcagccc cagtccgttc tgcacagcgg | 180 |
| ctacttccac ccactacttc gggcctggca gacagccacc accaccctca atgcctccaa | 240 |
| cctcatctac cccatctttg tcacggatgt tcctgatgac atacagccta tcaccagcct | 300 |
| cccaggagtg gccaggtatg tgtgtgaagcg gctggaagag atgctgaggc ccttggtgga | 360 |
| agagggccta cgctgtgtct tgatcttttgg cgtccccagc agagttccca aggacgagcg | 420 |
| gggttccgca gctgactccg aggagtcccc agctattgag gcaatccatc tgttgaggaa | 480 |
| gaccttcccc aacctcctgg tggcctgtga tgtctgcctg tgtccctaca cctcccatgg | 540 |
| tcactgcggg ctcctgagtg aaaacggagc attccgggct gaggagagcc gccagcggct | 600 |
| ggctgaggtg gcattggcgt atgccaaggc aggatgtcag gtggtagccc cgtcggacat | 660 |
| gatggatgga cgcgtggaag ccatcaaaga ggccctgatg gcacatggac ttggcaacag | 720 |
| ggtatcggta tgagctaca gtgccaaatt tgcttcctgt ttctatggcc ctttccggga | 780 |
| tgcagctaag tcaagcccag cttttgggga ccgccgctgc taccagctgc ccctggagc | 840 |
| acgaggcctg gctctccgag ctgtggaccg ggatgtacgg gaaggagctg acatgctcat | 900 |
| ggtgaagccg ggaatgccct acctggacat cgtgcgggag gtaaaggaca agcaccctga | 960 |
| cctccctctc gccgtgtacc acgtctctgg agagtttgcc atgctgtggc atggagccca | 1020 |
| ggccggggca tttgatctca aggctgccgt actggaggcc atgactgcct ccgcagagc | 1080 |
| aggtgctgac atcatcatca cctactacac accgcagctg ctgcagtggc tgaaggagga | 1140 |
| atgatggaga cagtgccagg cccaagaact agaactttaa aacgttcccg gggcctcaga | 1200 |
| caagtgaaaa ccaaagtaaa tgctgctttt agaactgtgc cctcatgccc tcttcctgct | 1260 |
| cacatgctag cggggcccag cagccctggg tggttttgcc agcatgctaa ctcttgtaac | 1320 |
| tcgcagctgc atcctatgag ctctcccaag cttccccgcc cctcccctgg gtcagccgtg | 1380 |
| aggcccacct ttgccaccct cagctctttc ctctggtgtg gcttcagctt gaaagcaacc | 1440 |
| tggagtcggg ggcacagcct ttggggcctg gctgggagag ggtcttggag cattagggga | 1500 |
| agaagagagc agtgggatct tggggcctga gaagccttgg aacgcttctg gcagcagagc | 1560 |
| tgggtgtggg aatgaggcct agatcgatat ccctgggtta gagttgaaat ttgccgcaat | 1620 |
| tccactggaa ggcatttccc acgaggccag aggttgccag gctgcctgag gtctcctatt | 1680 |
| ctactctgaa ccataaaccc agagaagaat tactcattaa ccagcataaa tactgcctga | 1740 |
| ggatcaaaac tcagaggcaa agagggagtt cctgactgct agaggtgcca ccaccacaaa | 1800 |
| cactttttat tcaggagata cttttttgaga atctctgctc tgttcctagg ttcagtgctg | 1860 |
| ggtcctggga atacagcagg acagacctca gcttatctct tcatagaaat tatacaaaga | 1920 |
| gaattgggga gacagctaag aagaaaacaa agaaataaag cagttacaaa ttgtgataag | 1980 |
| tgctttgaag gaaagaaggg gtctgagaca acaacgggga aggggcctct cttgaaacag | 2040 |
| tagttgggaa ggaggcagac atgcaccagt gatgtggtga caggtgctct gaaggaggtc | 2100 |
| accaggacct gacctctttg aaggatcaga aaatacttcc ctgaaggact gacatttgag | 2160 |
| cctagacctg aagggtgagc catcaagcta agacaattgg ggaagagcat tccagggaga | 2220 |
| gggaggagtt gtgcaaaggc cctggggctc cttctagctg gaggaatgca aggctagctt | 2280 |
| gtctggagca ctgagaggat ggcctgaact gagtggagag agacagacca ggaccaaacc | 2340 |
| atgcagaggt caagggccac attcacccttt tcagagtgac tcaatcaaat ttgtagtttg | 2400 |
| taaaagtatt ttaacagctc tgcggcaaag tgcaaatgaa aagtcttgat ggcatggact | 2460 |

| ggagcgggga cagtggggat ggagaaaggg gaatggattg tggatgtgtt tagaaggtag | 2520 |
| attcgatgtg aaggatgaat ctggcttgac cttctgggtg gctgatgggc catttactga | 2580 |
| gatggggcag cctggaagag aacagaagc agggtcgggg tggagggaga atactaaact | 2640 |
| tagcttgaga cattttgcaa taaggaagct atatctagag tgcttatgtg actcacctaa | 2700 |
| ggccactcaa caagtttgtg gcagaactgg attagaactg cacagaaaac agccaagctg | 2760 |
| ggatttgaac ccatgtagtc caactccaag gcctctgccc ctaaccactg tgccatacca | 2820 |
| cctcccaata atcaacagca aaattatagg tctaacaatg ttttatagac acccctccat | 2880 |
| ttatgtgatg ggtttgcatc ctgataaacc catcataagt tgaaaatatg atcataagtt | 2940 |
| gaaaatatga tcataagtca aaatgtatt taatatacct aacctaccaa acatcatagc | 3000 |
| ttagcctagc ctgccttaaa catgctcaga acacttacat tagcctacag tgggcaaaac | 3060 |
| tatccaacac aaaatctata ttgtaataaa gttgtaaaga attttgaata aaaattcaat | 3120 |
| atttgaaaaa aaaaaaaaaa aa | 3142 |

<210> SEQ ID NO 2
<211> LENGTH: 1154
<212> TYPE: DNA
<213> ORGANISM: Homo sapiens

<400> SEQUENCE: 2

| gcagccaaag ccccaggagc cctaggttcc aaccaactga tgcccctgtg cccactggcc | 60 |
| cacgccatgc agccccagtc cgttctgcac agcggctact ccacccact acttcgggcc | 120 |
| tggcagacag ccaccaccac cctcaatgcc tccaacctca tctaccccat ctttgtcacg | 180 |
| gatgttcctg atgacataca gcctatcacc agcctcccag gagtggccag gtatggtgtg | 240 |
| aagcggctgg aagagatgct gaggcccttg gtggaagagg gcctacgctg tgtcttgatc | 300 |
| tttggcgtcc ccagcagagt tcccaaggac gagcgggtt ccgcagctga ctccgaggag | 360 |
| tccccagcta ttgaggcaat ccatctgttg aggaagacct tccccaacct cctggtggcc | 420 |
| tgtgatgtct gcctgtgtcc ctacacctcc catggtcact gcgggctcct gagtgaaaac | 480 |
| ggagcattcc gggctgagga gagccgccag cggctggctg aggtggcatt ggcgtatgcc | 540 |
| aaggcaggat gtcaggtggt agcccgtcg gacatgatgg atggacgcgt ggaagccatc | 600 |
| aaagaggccc tgatggcaca tggacttggc aacagggtat cggtgatgag ctacagtgcc | 660 |
| aaatttgctt cctgtttcta tggccctttc cgggatgcag ctaagtcaag cccagctttt | 720 |
| ggggaccgcc gctgctacca gctgcccct ggagcacgag gcctggctct ccgagctgtg | 780 |
| gaccgggat tacgggaagg agctgacatg ctcatggtga agccgggaat gccctacctg | 840 |
| gacatcgtgc gggaggtaaa ggacaagcac cctgacctcc ctctcgccgt gtaccacgtc | 900 |
| tctggagagt ttgccatgct gtggcatgga gcccaggccg ggcatttga tctcaaggct | 960 |
| gccgtactgg aggccatgac tgccttccgc agagcaggtg ctgacatcat catcacctac | 1020 |
| tacacaccgc agctgctgca gtggctgaag gaggaatgat ggaggacagt gccaggccca | 1080 |
| agaactagaa ctttcaaacg ttcccggggc ctcagacaag tgacaaccaa agtaaatgct | 1140 |
| gcttttagaa ctgt | 1154 |

<210> SEQ ID NO 3
<211> LENGTH: 330
<212> TYPE: PRT
<213> ORGANISM: Homo sapiens

```
<400> SEQUENCE: 3

Met Gln Pro Gln Ser Val Leu His Ser Gly Tyr Phe His Pro Leu Leu
1               5                   10                  15

Arg Ala Trp Gln Thr Ala Thr Thr Leu Asn Ala Ser Asn Leu Ile
            20                  25                  30

Tyr Pro Ile Phe Val Thr Asp Val Pro Asp Ile Gln Pro Ile Thr
                35                  40                  45

Ser Leu Pro Gly Val Ala Arg Tyr Gly Val Lys Arg Leu Glu Met
    50                  55                  60

Leu Arg Pro Leu Val Glu Glu Gly Leu Arg Cys Val Leu Ile Phe Gly
65                  70                  75                  80

Val Pro Ser Arg Val Pro Lys Asp Glu Arg Gly Ser Ala Ala Asp Ser
                85                  90                  95

Glu Glu Ser Pro Ala Ile Glu Ala Ile His Leu Leu Arg Lys Thr Phe
            100                 105                 110

Pro Asn Leu Leu Val Ala Cys Asp Val Cys Leu Cys Pro Tyr Thr Ser
            115                 120                 125

His Gly His Cys Gly Leu Leu Ser Glu Asn Gly Ala Phe Arg Ala Glu
            130                 135                 140

Glu Ser Arg Gln Arg Leu Ala Glu Val Ala Leu Ala Tyr Ala Lys Ala
145                 150                 155                 160

Gly Cys Gln Val Val Ala Pro Ser Asp Met Met Asp Gly Arg Val Glu
                165                 170                 175

Ala Ile Lys Glu Ala Leu Met Ala His Gly Leu Gly Asn Arg Val Ser
            180                 185                 190

Val Met Ser Tyr Ser Ala Lys Phe Ala Ser Cys Phe Tyr Gly Pro Phe
            195                 200                 205

Arg Asp Ala Ala Lys Ser Ser Pro Ala Phe Gly Asp Arg Arg Cys Tyr
    210                 215                 220

Gln Leu Pro Pro Gly Ala Arg Gly Leu Ala Leu Arg Ala Val Asp Arg
225                 230                 235                 240

Asp Val Arg Glu Gly Ala Asp Met Leu Met Val Lys Pro Gly Met Pro
                245                 250                 255

Tyr Leu Asp Ile Val Arg Glu Val Lys Asp Lys His Pro Asp Leu Pro
            260                 265                 270

Leu Ala Val Tyr His Val Ser Gly Glu Phe Ala Met Leu Trp His Gly
            275                 280                 285

Ala Gln Ala Gly Ala Phe Asp Leu Lys Ala Ala Val Leu Glu Ala Met
            290                 295                 300

Thr Ala Phe Arg Arg Ala Gly Ala Asp Ile Ile Ile Thr Tyr Tyr Thr
305                 310                 315                 320

Pro Gln Leu Leu Gln Trp Leu Lys Glu Glu
                325                 330

<210> SEQ ID NO 4
<211> LENGTH: 27
<212> TYPE: DNA
<213> ORGANISM: Homo sapiens

<400> SEQUENCE: 4
ggctacctcc acccactgct tcgggcc                                      27

<210> SEQ ID NO 5
<211> LENGTH: 20
<212> TYPE: PRT
```

-continued

```
<213> ORGANISM: Spinacia oleracea

<400> SEQUENCE: 5

Asp Val Ala Leu Asp Pro Tyr Tyr Tyr Asp Gly His Asp Gly Ile Lys
1               5                   10                  15

Lys Thr Tyr Gln
            20

<210> SEQ ID NO 6
<211> LENGTH: 20
<212> TYPE: PRT
<213> ORGANISM: Arabidopsis thaliana

<400> SEQUENCE: 6

Asp Val Ala Leu Asp Pro Tyr Ser Ser Asp Gly His Asp Gly Ile Lys
1               5                   10                  15

Lys Thr Tyr Gln
            20

<210> SEQ ID NO 7
<211> LENGTH: 20
<212> TYPE: PRT
<213> ORGANISM: Raphanus sativus

<400> SEQUENCE: 7

Asp Val Ala Leu Asp Pro Tyr Ser Ser Asp Gly His Asp Gly Ile Lys
1               5                   10                  15

Lys Thr Tyr Gln
            20

<210> SEQ ID NO 8
<211> LENGTH: 20
<212> TYPE: PRT
<213> ORGANISM: Lycopersicon esculentum

<400> SEQUENCE: 8

Asp Val Ala Leu Asp Pro Tyr Ser Ser Asp Gly His Asp Gly Ile Lys
1               5                   10                  15

Lys Thr Tyr Gln
            20

<210> SEQ ID NO 9
<211> LENGTH: 20
<212> TYPE: PRT
<213> ORGANISM: Glycine max

<400> SEQUENCE: 9

Asp Val Ala Leu Asp Pro Tyr Ser Ser Asp Gly His Asp Gly Ile Lys
1               5                   10                  15

Lys Thr Tyr Gln
            20

<210> SEQ ID NO 10
<211> LENGTH: 20
<212> TYPE: PRT
<213> ORGANISM: Pisum sativum

<400> SEQUENCE: 10

Asp Val Ala Leu Asp Pro Tyr Ser Ser Asp Gly His Asp Gly Ile Lys
1               5                   10                  15

Lys Thr Tyr Gln
            20
```

<210> SEQ ID NO 11
<211> LENGTH: 20
<212> TYPE: PRT
<213> ORGANISM: Amaranthus tricolor

<400> SEQUENCE: 11

Asp Val Ala Leu Asp Pro Tyr Ser Ser Asp Gly His Asp Gly Ile Lys
1               5                   10                  15

Lys Thr Tyr Gln
            20

<210> SEQ ID NO 12
<211> LENGTH: 20
<212> TYPE: PRT
<213> ORGANISM: Hordeum vulgare

<400> SEQUENCE: 12

Asp Val Ala Leu Asp Pro Tyr Ser Ser Asp Gly His Asp Gly Ile Lys
1               5                   10                  15

Lys Thr Tyr Gln
            20

<210> SEQ ID NO 13
<211> LENGTH: 20
<212> TYPE: PRT
<213> ORGANISM: Selaginella martensii

<400> SEQUENCE: 13

Asp Val Ala Leu Asp Pro Tyr Ser Ser Asp Gly His Asp Gly Ile Lys
1               5                   10                  15

Lys Thr Tyr Gln
            20

<210> SEQ ID NO 14
<211> LENGTH: 20
<212> TYPE: PRT
<213> ORGANISM: Physcomitrella patens

<400> SEQUENCE: 14

Asp Val Ala Leu Asp Pro Tyr Ser Ser Asp Gly His Asp Gly Ile Lys
1               5                   10                  15

Lys Thr Tyr Gln
            20

<210> SEQ ID NO 15
<211> LENGTH: 20
<212> TYPE: PRT
<213> ORGANISM: Chlamydomonas reinhardtii

<400> SEQUENCE: 15

Asp Val Ala Leu Asp Pro Tyr Asn Ser Asp Gly His Asp Gly Ile Lys
1               5                   10                  15

Lys Thr Tyr Gln
            20

<210> SEQ ID NO 16
<211> LENGTH: 11
<212> TYPE: PRT
<213> ORGANISM: Volvox carteri

<400> SEQUENCE: 16

-continued

Asp Gly His Asp Gly Ile Lys Lys Thr Tyr Gln
1               5                   10

<210> SEQ ID NO 17
<211> LENGTH: 20
<212> TYPE: PRT
<213> ORGANISM: Cyanophora paradoxa

<400> SEQUENCE: 17

Asp Ile Ala Leu Asp Pro Tyr Asn Ser Asp Gly His Asp Gly Ile Lys
1               5                   10                  15

Thr Thr Tyr Gln
            20

<210> SEQ ID NO 18
<211> LENGTH: 5
<212> TYPE: PRT
<213> ORGANISM: Guillardia theta

<400> SEQUENCE: 18

Lys Arg Thr Tyr Gln
1               5

<210> SEQ ID NO 19
<211> LENGTH: 20
<212> TYPE: PRT
<213> ORGANISM: Fucus vesiculosus

<400> SEQUENCE: 19

Asp Val Ala Leu Asp Pro Tyr Ser Asp Gln Gly His Asp Gly Val Lys
1               5                   10                  15

Lys Thr Tyr Gln
            20

<210> SEQ ID NO 20
<211> LENGTH: 20
<212> TYPE: PRT
<213> ORGANISM: Laminaria saccharina

<400> SEQUENCE: 20

Asp Val Ala Leu Asp Pro Tyr Ser Asp Gln Gly His Asp Gly Val Lys
1               5                   10                  15

Lys Thr Tyr Gln
            20

<210> SEQ ID NO 21
<211> LENGTH: 20
<212> TYPE: PRT
<213> ORGANISM: Odontella sinensis

<400> SEQUENCE: 21

Asp Val Ala Leu Asp Pro Tyr Ser Asp Gln Gly His Asp Gly Val Lys
1               5                   10                  15

Lys Thr Tyr Gln
            20

<210> SEQ ID NO 22
<211> LENGTH: 20
<212> TYPE: PRT
<213> ORGANISM: Gracilaria sp.

<400> SEQUENCE: 22

Asp Val Ala Leu Asp Pro Tyr Ser Asp Gln Gly His Asp Gly Val Lys

```
1               5                   10                  15

Asn Thr Tyr Gln
            20

<210> SEQ ID NO 23
<211> LENGTH: 20
<212> TYPE: PRT
<213> ORGANISM: Gonyaulax polyedra

<400> SEQUENCE: 23

Asp Val Ala Leu Asp Pro Tyr Asn Ser Leu Gly His Asp Gly Ile Lys
1               5                   10                  15

Gln Thr Tyr Gln
            20

<210> SEQ ID NO 24
<211> LENGTH: 20
<212> TYPE: PRT
<213> ORGANISM: Plasmodium falciparum

<400> SEQUENCE: 24

Asp Val Ala Leu Asp Pro Tyr Asn Ile Tyr Gly His Asp Gly Ile Lys
1               5                   10                  15

Gln Ser Tyr Gln
            20

<210> SEQ ID NO 25
<211> LENGTH: 20
<212> TYPE: PRT
<213> ORGANISM: Mus musculus

<400> SEQUENCE: 25

Asp Val Cys Leu Cys Pro Tyr Thr Ser His Gly His Cys Gly Leu Arg
1               5                   10                  15

Arg Cys Tyr Gln
            20

<210> SEQ ID NO 26
<211> LENGTH: 20
<212> TYPE: PRT
<213> ORGANISM: Homo sapiens

<400> SEQUENCE: 26

Asp Val Cys Leu Cys Pro Tyr Thr Ser His Gly His Cys Gly Leu Arg
1               5                   10                  15

Arg Cys Tyr Gln
            20

<210> SEQ ID NO 27
<211> LENGTH: 20
<212> TYPE: PRT
<213> ORGANISM: Rattus norvegicus

<400> SEQUENCE: 27

Asp Val Cys Leu Cys Pro Tyr Thr Ser His Gly His Cys Gly Leu Arg
1               5                   10                  15

Arg Cys Tyr Gln
            20

<210> SEQ ID NO 28
<211> LENGTH: 20
<212> TYPE: PRT
```

-continued

```
<213> ORGANISM: Drosophila melanogaster

<400> SEQUENCE: 28

Asp Val Cys Ile Cys Pro Tyr Ser Ser His Gly His Cys Gly Leu Arg
1               5                   10                  15

Arg Cys Tyr Gln
            20

<210> SEQ ID NO 29
<211> LENGTH: 20
<212> TYPE: PRT
<213> ORGANISM: Saccharomyces cerevisiae

<400> SEQUENCE: 29

Asp Val Cys Leu Cys Glu Tyr Thr Ser His Gly His Cys Gly Val Arg
1               5                   10                  15

Lys Cys Tyr Gln
            20

<210> SEQ ID NO 30
<211> LENGTH: 20
<212> TYPE: PRT
<213> ORGANISM: Aspergillus fumigatus

<400> SEQUENCE: 30

Asp Val Cys Leu Cys Glu Tyr Thr Ser His Gly His Cys Gly Ile Arg
1               5                   10                  15

Arg Cys Tyr Gln
            20

<210> SEQ ID NO 31
<211> LENGTH: 20
<212> TYPE: PRT
<213> ORGANISM: Candida glabrata

<400> SEQUENCE: 31

Asp Val Cys Leu Cys Glu Tyr Thr Ser His Gly His Cys Gly Val Arg
1               5                   10                  15

Lys Cys Tyr Gln
            20

<210> SEQ ID NO 32
<211> LENGTH: 20
<212> TYPE: PRT
<213> ORGANISM: Schizosaccharomyces pombe

<400> SEQUENCE: 32

Asp Val Cys Leu Cys Glu Tyr Thr Asp His Gly His Cys Gly Leu Arg
1               5                   10                  15

Ser Cys Tyr Gln
            20

<210> SEQ ID NO 33
<211> LENGTH: 20
<212> TYPE: PRT
<213> ORGANISM: Candida albicans

<400> SEQUENCE: 33

Asp Val Cys Leu Cys Glu Tyr Thr Asp His Gly His Cys Gly Ile Arg
1               5                   10                  15

Lys Ala Tyr Gln
            20
```

```
<210> SEQ ID NO 34
<211> LENGTH: 20
<212> TYPE: PRT
<213> ORGANISM: Sulfolobus sp.

<400> SEQUENCE: 34

Asp Glu Cys Thr Asp Glu Tyr Thr Ser His Gly His Cys Gly Ile Arg
1               5                   10                  15

Arg Gly Tyr Gln
            20

<210> SEQ ID NO 35
<211> LENGTH: 20
<212> TYPE: PRT
<213> ORGANISM: Sulfolobus solfataricus

<400> SEQUENCE: 35

Asp Glu Cys Thr Asp Glu Tyr Met Ala Asn Gly His Cys Gly Leu Arg
1               5                   10                  15

Arg Gly Tyr Gln
            20

<210> SEQ ID NO 36
<211> LENGTH: 20
<212> TYPE: PRT
<213> ORGANISM: Pyrobaculum aerophilum

<400> SEQUENCE: 36

Asp Val Cys Leu Cys Glu Tyr Thr Glu His Gly His Cys Gly Val Arg
1               5                   10                  15

Arg Thr Tyr Gln
            20

<210> SEQ ID NO 37
<211> LENGTH: 20
<212> TYPE: PRT
<213> ORGANISM: Aeropyrum pernix

<400> SEQUENCE: 37

Asp Val Cys Leu Cys Gly Tyr Thr Asp His Gly His Cys Gly Tyr Arg
1               5                   10                  15

Arg Ser Tyr Gln
            20

<210> SEQ ID NO 38
<211> LENGTH: 20
<212> TYPE: PRT
<213> ORGANISM: Thermoplasma volcanium

<400> SEQUENCE: 38

Asp Leu Cys Leu Cys Glu Tyr Thr Asp Thr Gly Gln Cys Gly Leu Arg
1               5                   10                  15

Lys Ser Tyr Gln
            20

<210> SEQ ID NO 39
<211> LENGTH: 20
<212> TYPE: PRT
<213> ORGANISM: ferroplasma acidarmanus

<400> SEQUENCE: 39
```

-continued

Asp Leu Cys Leu Cys Glu Tyr Thr Asp Thr Gly His Cys Gly Val Arg
1               5                   10                  15

Lys Ser Tyr Gln
            20

<210> SEQ ID NO 40
<211> LENGTH: 20
<212> TYPE: PRT
<213> ORGANISM: Thermoplasma acidophilum

<400> SEQUENCE: 40

Asp Leu Cys Leu Cys Glu Tyr Thr Asp Thr Gly Gln Cys Gly Leu Arg
1               5                   10                  15

Lys Ser Tyr Gln
            20

<210> SEQ ID NO 41
<211> LENGTH: 20
<212> TYPE: PRT
<213> ORGANISM: Methanothermus sociabilis

<400> SEQUENCE: 41

Asp Val Cys Leu Cys Gln Tyr Thr Glu His Gly His Cys Gly Ile Arg
1               5                   10                  15

Ser Thr Tyr Gln
            20

<210> SEQ ID NO 42
<211> LENGTH: 20
<212> TYPE: PRT
<213> ORGANISM: methanothermobacter thermautotrophicus

<400> SEQUENCE: 42

Asp Val Cys Leu Cys Gln Tyr Thr Ser His Gly His Cys Gly Ile Arg
1               5                   10                  15

Arg Ser Tyr Gln
            20

<210> SEQ ID NO 43
<211> LENGTH: 20
<212> TYPE: PRT
<213> ORGANISM: Archaeoglobus fulgidus

<400> SEQUENCE: 43

Asp Val Cys Leu Cys Glu Tyr Thr Thr His Gly His Cys Gly Val Arg
1               5                   10                  15

Arg Gly Tyr Gln
            20

<210> SEQ ID NO 44
<211> LENGTH: 20
<212> TYPE: PRT
<213> ORGANISM: Halobacterium sp.

<400> SEQUENCE: 44

Asp Val Cys Leu Cys Glu Tyr Thr Ser His Gly His Cys Gly Val Arg
1               5                   10                  15

Arg His Tyr Gln
            20

<210> SEQ ID NO 45
<211> LENGTH: 20

```
<212> TYPE: PRT
<213> ORGANISM: Methanococcus jannaschii

<400> SEQUENCE: 45

Asp Cys Cys Leu Cys Glu Tyr Thr Ser His Gly His Cys Gly Ile Arg
1               5                   10                  15

Lys Ser Tyr Gln
            20

<210> SEQ ID NO 46
<211> LENGTH: 18
<212> TYPE: PRT
<213> ORGANISM: Methanosarcina barkeri

<400> SEQUENCE: 46

Asp Val Cys Met Cys Glu Tyr Thr Ser His Gly His Cys Gly Ile Arg
1               5                   10                  15

Ser Thr

<210> SEQ ID NO 47
<211> LENGTH: 20
<212> TYPE: PRT
<213> ORGANISM: Streptomyces coelicolor

<400> SEQUENCE: 47

Asp Ile Ala Leu Asp Pro Tyr Thr Thr His Gly Gln Asp Gly Ile Lys
1               5                   10                  15

Lys Thr Tyr Gln
            20

<210> SEQ ID NO 48
<211> LENGTH: 20
<212> TYPE: PRT
<213> ORGANISM: Mycobacterium tuberculosis

<400> SEQUENCE: 48

Asp Val Ala Leu Asp Pro Phe Thr Thr His Gly Gln Asp Gly Ile Lys
1               5                   10                  15

His Ser Tyr Gln
            20

<210> SEQ ID NO 49
<211> LENGTH: 20
<212> TYPE: PRT
<213> ORGANISM: Mycobacterium avium

<400> SEQUENCE: 49

Asp Val Ala Leu Asp Pro Phe Thr Ser His Gly Gln Asp Gly Leu Lys
1               5                   10                  15

Tyr Ser Tyr Gln
            20

<210> SEQ ID NO 50
<211> LENGTH: 20
<212> TYPE: PRT
<213> ORGANISM: Mycobacterium leprae

<400> SEQUENCE: 50

Asp Val Ala Leu Asp Pro Phe Thr Thr His Gly Gln Asp Gly Ile Lys
1               5                   10                  15

Lys Asn Tyr Gln
            20
```

```
<210> SEQ ID NO 51
<211> LENGTH: 20
<212> TYPE: PRT
<213> ORGANISM: Mycobacterium bovis

<400> SEQUENCE: 51

Asp Val Ala Leu Asp Pro Tyr Thr Thr His Gly Gln Asp Gly Ile Lys
1               5                   10                  15

Lys Thr Tyr Gln
            20

<210> SEQ ID NO 52
<211> LENGTH: 20
<212> TYPE: PRT
<213> ORGANISM: Mycobacterium smegmatis

<400> SEQUENCE: 52

Asp Val Ala Leu Asp Pro Tyr Thr Asp His Gly His Asp Gly Ile Lys
1               5                   10                  15

Ser Ser Tyr Gln
            20

<210> SEQ ID NO 53
<211> LENGTH: 20
<212> TYPE: PRT
<213> ORGANISM: Corynebacterium diphtheriae

<400> SEQUENCE: 53

Asp Val Ala Leu Asp Pro Phe Thr Asp His Gly His Asp Gly Val Lys
1               5                   10                  15

Lys Thr Tyr Gln
            20

<210> SEQ ID NO 54
<211> LENGTH: 20
<212> TYPE: PRT
<213> ORGANISM: Staphylococcus epidermidis

<400> SEQUENCE: 54

Asp Val Ala Leu Asp Pro Phe Thr Ser His Gly His Asp Gly Ile Lys
1               5                   10                  15

Asn Ser Tyr Tyr
            20

<210> SEQ ID NO 55
<211> LENGTH: 20
<212> TYPE: PRT
<213> ORGANISM: Staphylococcus aureus

<400> SEQUENCE: 55

Asp Val Ala Leu Asp Pro Phe Thr Ser His Gly His Asp Gly Ile Lys
1               5                   10                  15

Lys Thr Tyr Tyr
            20

<210> SEQ ID NO 56
<211> LENGTH: 20
<212> TYPE: PRT
<213> ORGANISM: Bacillus subtilis

<400> SEQUENCE: 56
```

Asp Ala Ala Leu Asp Pro Phe Thr Thr His Gly His Asp Gly Ile Lys
1               5                   10                  15

Lys Thr Tyr Tyr
        20

<210> SEQ ID NO 57
<211> LENGTH: 20
<212> TYPE: PRT
<213> ORGANISM: Bacillus halodenitrificans

<400> SEQUENCE: 57

Asp Val Ala Leu Asp Pro Tyr Thr Ser His Gly His Asp Gly Leu Lys
1               5                   10                  15

Arg Thr Tyr Gln
        20

<210> SEQ ID NO 58
<211> LENGTH: 20
<212> TYPE: PRT
<213> ORGANISM: Bacillus anthracis

<400> SEQUENCE: 58

Asp Ala Ala Leu Asp Pro Phe Thr Ser His Gly His Asp Gly Ile Lys
1               5                   10                  15

Lys Thr Tyr Tyr
        20

<210> SEQ ID NO 59
<211> LENGTH: 20
<212> TYPE: PRT
<213> ORGANISM: geobacillus staerothermophilus

<400> SEQUENCE: 59

Asp Val Ala Leu Asp Pro Phe Thr Ser His Gly His Asp Gly Leu Lys
1               5                   10                  15

Arg Thr Tyr Gln
        20

<210> SEQ ID NO 60
<211> LENGTH: 20
<212> TYPE: PRT
<213> ORGANISM: Listeria innocua

<400> SEQUENCE: 60

Asp Ala Ala Leu Asp Pro Phe Thr Thr His Gly His Asp Gly Ile Lys
1               5                   10                  15

Lys Thr Tyr Tyr
        20

<210> SEQ ID NO 61
<211> LENGTH: 20
<212> TYPE: PRT
<213> ORGANISM: Listeria monocytogenes

<400> SEQUENCE: 61

Asp Ile Ala Leu Asp Pro Tyr Asn Ala Asn Gly His Asp Gly Leu Lys
1               5                   10                  15

Lys Thr Tyr Gln
        20

<210> SEQ ID NO 62
<211> LENGTH: 20

```
<212> TYPE: PRT
<213> ORGANISM: Desulfitobacterium hafniense

<400> SEQUENCE: 62

Asp Val Ala Leu Asp Pro Tyr Asn Ala Asn Gly His Asp Gly Leu Lys
1               5                   10                  15

Lys Thr Tyr Gln
            20

<210> SEQ ID NO 63
<211> LENGTH: 20
<212> TYPE: PRT
<213> ORGANISM: Selenomonas ruminantium

<400> SEQUENCE: 63

Asp Val Ala Leu Asp Pro Tyr Asn Ser Asp Gly His Asp Gly Leu Lys
1               5                   10                  15

Lys Thr Tyr Gln
            20

<210> SEQ ID NO 64
<211> LENGTH: 20
<212> TYPE: PRT
<213> ORGANISM: Clostridium botulinum

<400> SEQUENCE: 64

Asp Val Ala Leu Asp Pro Tyr Thr Thr His Gly His Asp Gly Ile Lys
1               5                   10                  15

Ser Ser Tyr Gln
            20

<210> SEQ ID NO 65
<211> LENGTH: 20
<212> TYPE: PRT
<213> ORGANISM: Clostridium difficile

<400> SEQUENCE: 65

Asp Val Ala Leu Asp Pro Tyr Thr Ile Ser Gly His Asp Gly Ile Lys
1               5                   10                  15

Ser Ser Tyr Gln
            20

<210> SEQ ID NO 66
<211> LENGTH: 20
<212> TYPE: PRT
<213> ORGANISM: Clostridium josui

<400> SEQUENCE: 66

Asp Val Ala Leu Asp Pro Tyr Thr Ile His Gly His Asp Gly Ile Lys
1               5                   10                  15

Ser Gly Tyr Gln
            20

<210> SEQ ID NO 67
<211> LENGTH: 20
<212> TYPE: PRT
<213> ORGANISM: Clostridium acetobutylicum

<400> SEQUENCE: 67

Asp Val Ala Leu Asp Pro Tyr Thr Ser His Gly Gln Asp Gly Leu Lys
1               5                   10                  15

Lys Thr Tyr Gln
```

<210> SEQ ID NO 68
<211> LENGTH: 20
<212> TYPE: PRT
<213> ORGANISM: Clostridium perfringens

<400> SEQU

```
Asp Val Ala Leu Asp Pro Tyr Thr Ser His Gly Gln Asp Gly Val Lys
1               5                   10                  15

Met Thr Tyr Gln
            20

<210> SEQ ID NO 74
<211> LENGTH: 20
<212> TYPE: PRT
<213> ORGANISM: Desulfacinum infernum

<400> SEQUENCE: 74

Asp Val Ala Leu Asp Pro Tyr Thr Val His Gly Gln Asp Gly Leu Lys
1               5                   10                  15

Lys Thr Tyr Gln
            20

<210> SEQ ID NO 75
<211> LENGTH: 20
<212> TYPE: PRT
<213> ORGANISM: Campylobacter jejuni

<400> SEQUENCE: 75

Asp Val Ala Leu Asp Pro Tyr Thr Val His Gly Gln Asp Gly Leu Lys
1               5                   10                  15

Lys Thr Tyr Gln
            20

<210> SEQ ID NO 76
<211> LENGTH: 20
<212> TYPE: PRT
<213> ORGANISM: Helicobacter pylori

<400> SEQUENCE: 76

Asp Val Ala Leu Asp Pro Tyr Thr Ser His Gly Gln Asp Gly Val Lys
1               5                   10                  15

Met Thr Tyr Gln
            20

<210> SEQ ID NO 77
<211> LENGTH: 20
<212> TYPE: PRT
<213> ORGANISM: magnetic coccus MP17

<400> SEQUENCE: 77

Asp Val Ala Leu Asp Pro Tyr Thr Ser His Gly Gln Asp Gly Val Lys
1               5                   10                  15

Met Thr Tyr Gln
            20

<210> SEQ ID NO 78
<211> LENGTH: 20
<212> TYPE: PRT
<213> ORGANISM: Pseudomonas fluorescens

<400> SEQUENCE: 78

Asp Ile Ala Leu Asp Pro Phe Thr Thr Ser Gly His Asp Gly Ile Lys
1               5                   10                  15

Arg Gln Tyr Gln
            20

<210> SEQ ID NO 79
```

```
<211> LENGTH: 20
<212> TYPE: PRT
<213> ORGANISM: Coxiella burnetii

<400> SEQUENCE: 79

Asp Ile Ala Leu As

-continued

```
Lys Thr Tyr Gln
            20

<210> SEQ ID NO 85
<211> LENGTH: 20
<212> TYPE: PRT
<213> ORGANISM: Salmonella typhimurium

<400> SEQUENCE: 85

Asp Val Ala Leu Asp Pro Tyr Ser Ser Asp Gly His Asp Gly Ile Lys
1               5                   10                  15

Lys Thr Tyr Gln
            20

<210> SEQ ID NO 86
<211> LENGTH: 20
<212> TYPE: PRT
<213> ORGANISM: Yersinia enterocolitica

<400> SEQUENCE: 86

Asp Val Ala Leu Asp Pro Tyr Ser Cys Asp Gly His Asp Gly Ile Lys
1               5                   10                  15

Ser Thr Tyr Gln
            20

<210> SEQ ID NO 87
<211> LENGTH: 20
<212> TYPE: PRT
<213> ORGANISM: Pseudomonas syringae

<400> SEQUENCE: 87

Asp Val Ala Leu Asp Pro Tyr Ser Cys Asp Gly His Asp Gly Leu Lys
1               5                   10                  15

Ser Thr Tyr Gln
            20

<210> SEQ ID NO 88
<211> LENGTH: 20
<212> TYPE: PRT
<213> ORGANISM: Pseudomonas aeruginosa

<400> SEQUENCE: 88

Asp Val Ala Leu Asp Pro Tyr Ser Cys Asp Gly His Asp Gly Ile Lys
1               5                   10                  15

Asp Thr Tyr Gln
            20

<210> SEQ ID NO 89
<211> LENGTH: 20
<212> TYPE: PRT
<213> ORGANISM: Actinobacillus sp.

<400> SEQUENCE: 89

Asp Val Ala Leu Asp Pro Phe Thr Thr His Gly His Asp Gly Leu Lys
1               5                   10                  15

Lys Thr Tyr Gln
            20

<210> SEQ ID NO 90
<211> LENGTH: 20
<212> TYPE: PRT
<213> ORGANISM: Pasteurella multocida
```

```
<400> SEQUENCE: 90

Asp Thr Cys Leu Cys Glu Tyr Thr Ser His Gly His Cys Gly Tyr Arg
1               5                   10                  15

Arg Thr Tyr Gln
            20

<210> SEQ ID NO 91
<211> LENGTH: 20
<212> TYPE: PRT
<213> ORGANISM: Shewanella putrefaciens

<400> SEQUENCE: 91

Asp Thr Cys Leu Cys Glu Tyr Thr Ser His Gly His Cys Gly Tyr Arg
1               5                   10                  15

Arg Thr Tyr Gln
            20

<210> SEQ ID NO 92
<211> LENGTH: 20
<212> TYPE: PRT
<213> ORGANISM: Methylococcus capsulatus

<400> SEQUENCE: 92

Asp Thr Cys Leu Cys Glu Tyr Thr Asn His Gly His Cys Gly Tyr Arg
1               5                   10                  15

Arg Thr Tyr Gln
            20

<210> SEQ ID NO 93
<211> LENGTH: 20
<212> TYPE: PRT
<213> ORGANISM: Vibrio cholerae

<400> SEQUENCE: 93

Asp Leu Cys Leu Asp Glu Phe Thr Asp His Gly His Cys Gly Val Arg
1               5                   10                  15

Lys Thr Tyr Gln
            20

<210> SEQ ID NO 94
<211> LENGTH: 20
<212> TYPE: PRT
<213> ORGANISM: Xylella fastidiosa

<400> SEQUENCE: 94

Asp Val Cys Leu Asp Glu Phe Thr Asp His Gly His Cys Gly Val Arg
1               5                   10                  15

Arg Ala Tyr Gln
            20

<210> SEQ ID NO 95
<211> LENGTH: 20
<212> TYPE: PRT
<213> ORGANISM: PROTEOBACTERIUM EBAC31A08

<400> SEQUENCE: 95

Asp Thr Cys Leu Asp Glu Phe Thr Asp His Gly His Cys Gly Val Arg
1               5                   10                  15

Arg Thr Tyr Gln
            20
```

<210> SEQ ID NO 96
<211> LENGTH: 20
<212> TYPE: PRT
<213> ORGANISM: Caulobacter crescentus

<400> SEQUENCE: 96

Asp Thr Cys Leu Asp Glu Phe Thr Asp His Gly His Cys Gly Val Arg
1               5                   10                  15

Arg Thr Tyr Gln
        20

<210> SEQ ID NO 97
<211> LENGTH: 20
<212> TYPE: PRT
<213> ORGANISM: Agrobacterium tumefaciens

<400> SEQUENCE: 97

Asp Thr Cys Leu Asp Glu Phe Thr Asp His Gly His Cys Gly Val Arg
1               5                   10                  15

Arg Thr Tyr Gln
        20

<210> SEQ ID NO 98
<211> LENGTH: 20
<212> TYPE: PRT
<213> ORGANISM: Sinorhizobium meliloti

<400> SEQUENCE: 98

Asp Thr Cys Leu Asp Glu Phe Thr Asp His Gly His Cys Gly Val Arg
1               5                   10                  15

Arg Thr Tyr Gln
        20

<210> SEQ ID NO 99
<211> LENGTH: 20
<212> TYPE: PRT
<213> ORGANISM: Brucella melitensis

<400> SEQUENCE: 99

Asp Thr Cys Leu Asp Glu Phe Thr Asp His Gly His Cys Gly Val Arg
1               5                   10                  15

Arg Thr Tyr Gln
        20

<210> SEQ ID NO 100
<211> LENGTH: 20
<212> TYPE: PRT
<213> ORGANISM: Rhodopseudomonas palustris

<400> SEQUENCE: 100

Asp Thr Cys Leu Asp Glu Phe Thr Asp His Gly His Cys Gly Ile Arg
1               5                   10                  15

Arg Ala Tyr Gln
        20

<210> SEQ ID NO 101
<211> LENGTH: 20
<212> TYPE: PRT
<213> ORGANISM: mesorhizobium loti

<400> SEQUENCE: 101

Asp Thr Cys Leu Cys Glu Tyr Thr Asp His Gly His Cys Gly Val Arg
1               5                   10                  15

Lys Thr Tyr Gln
            20

<210> SEQ ID NO 102
<211> LENGTH: 20
<212> TYPE: PRT
<213> ORGANISM: Bradyrhizobium japonicum

<400> SEQUENCE: 102

Asp Thr Cys Leu Cys Glu Tyr Thr Asp His Gly His Cys Gly Val Arg
1               5                   10                  15

Lys Thr Tyr Gln
            20

<210> SEQ ID NO 103
<211> LENGTH: 20
<212> TYPE: PRT
<213> ORGANISM: Brucella melitensis

<400> SEQUENCE: 103

Asp Thr Cys Leu Cys Glu Tyr Thr Asp His Gly His Cys Gly Leu Arg
1               5                   10                  15

Lys Thr Tyr Gln
            20

<210> SEQ ID NO 104
<211> LENGTH: 20
<212> TYPE: PRT
<213> ORGANISM: Rhodobacter capsulatus

<400> SEQUENCE: 104

Asp Thr Cys Leu Cys Gln Phe Thr Asp His Gly His Cys Gly Val Arg
1               5                   10                  15

Lys Thr Tyr Gln
            20

<210> SEQ ID NO 105
<211> LENGTH: 20
<212> TYPE: PRT
<213> ORGANISM: Rhodobacter sphaeroides

<400> SEQUENCE: 105

Asp Thr Cys Leu Cys Gln Phe Thr Ser His Gly His Cys Gly Val Arg
1               5                   10                  15

Lys Thr Tyr Gln
            20

<210> SEQ ID NO 106
<211> LENGTH: 20
<212> TYPE: PRT
<213> ORGANISM: Magnetospirillum magnetotacticum

<400> SEQUENCE: 106

Asp Thr Cys Leu Cys Glu Tyr Thr Ser His Gly His Cys Gly Val Arg
1               5                   10                  15

Lys Thr Tyr Gln
            20

<210> SEQ ID NO 107
<211> LENGTH: 20
<212> TYPE: PRT
<213> ORGANISM: Rickettsia conorii

```
<400> SEQUENCE: 107

Asp Thr Cys Leu Cys Glu Phe Thr Asp His Gly His Cys Gly Val Arg
1               5                   10                  15

Lys Ser Tyr Gln
            20

<210> SEQ ID NO 108
<211> LENGTH: 20
<212> TYPE: PRT
<213> ORGANISM: Rickettsia prowazekii

<400> SEQUENCE: 108

Asp Thr Cys Leu Cys Glu Phe Thr Asp His Gly His Cys Gly Val Arg
1               5                   10                  15

Lys Ser Tyr Gln
            20

<210> SEQ ID NO 109
<211> LENGTH: 20
<212> TYPE: PRT
<213> ORGANISM: Wolbachia sp.

<400> SEQUENCE: 109

Asp Val Cys Leu Cys Glu Tyr Thr Asp His Gly His Cys Gly Val Arg
1               5                   10                  15

Arg Thr Tyr Gln
            20

<210> SEQ ID NO 110
<211> LENGTH: 20
<212> TYPE: PRT
<213> ORGANISM: novosphingobium aromaticivorans

<400> SEQUENCE: 110

Asp Val Cys Met Cys Glu Tyr Thr Asp His Gly His Cys Gly His Arg
1               5                   10                  15

Arg Gln Tyr Gln
            20

<210> SEQ ID NO 111
<211> LENGTH: 20
<212> TYPE: PRT
<213> ORGANISM: Bordetella bronchiseptica

<400> SEQUENCE: 111

Asp Val Cys Met Cys Gln Tyr Thr Ser His Gly His Cys Gly Ile Arg
1               5                   10                  15

Lys Thr Tyr Gln
            20

<210> SEQ ID NO 112
<211> LENGTH: 20
<212> TYPE: PRT
<213> ORGANISM: Bordetella pertussis

<400> SEQUENCE: 112

Asp Val Cys Met Cys Gln Tyr Thr Ser His Gly His Cys Gly Ile Arg
1               5                   10                  15

Lys Thr Tyr Gln
            20
```

```
<210> SEQ ID NO 113
<211> LENGTH: 15
<212> TYPE: PRT
<213> ORGANISM: Nitrosomonas europaea

<400> SEQUENCE: 113

Asp Ile Cys Met Cys Glu Tyr Thr Ser His Gly His Cys Gly Ile
1               5                   10                  15

<210> SEQ ID NO 114
<211> LENGTH: 20
<212> TYPE: PRT
<213> ORGANISM: Burkholderia mallei

<400> SEQUENCE: 114

Asp Val Cys Met Cys Glu Tyr Thr Ser His Gly His Cys Gly Ile Arg
1               5                   10                  15

Lys Ser Tyr Gln
            20

<210> SEQ ID NO 115
<211> LENGTH: 20
<212> TYPE: PRT
<213> ORGANISM: Burkholderia pseudomallei

<400> SEQUENCE: 115

Asp Val Cys Met Cys Glu Tyr Thr Ser His Gly His Cys Gly Ile Arg
1               5                   10                  15

Lys Thr Tyr Gln
            20

<210> SEQ ID NO 116
<211> LENGTH: 20
<212> TYPE: PRT
<213> ORGANISM: Burkholderia sp.

<400> SEQUENCE: 116

Asp Val Cys Phe Cys Glu Tyr Thr Thr His Gly His Cys Gly Val Arg
1               5                   10                  15

Arg Thr Tyr Gln
            20

<210> SEQ ID NO 117
<211> LENGTH: 20
<212> TYPE: PRT
<213> ORGANISM: Neisseria meningitidis

<400> SEQUENCE: 117

Asp Thr Cys Leu Cys Glu Tyr Thr Ser His Gly His Cys Gly His Arg
1               5                   10                  15

Ala Ser Tyr Gln
            20

<210> SEQ ID NO 118
<211> LENGTH: 20
<212> TYPE: PRT
<213> ORGANISM: Neisseria gonorrhoeae

<400> SEQUENCE: 118

Asp Val Cys Leu Cys Glu Tyr Met Ser His Gly His Cys Gly Ile Arg
1               5                   10                  15

Lys Ser Tyr Gln
```

<210> SEQ ID NO 119
<211> LENGTH: 5
<212> TYPE: PRT
<213> ORGANISM: Ralstonia solanacearum

<400> SE

-continued

```
Lys Ser Tyr Gln
            20

<210> SEQ ID NO 125
<211> LENGTH: 20
<212> TYPE: PRT
<213> ORGANISM: Chlorobium vibrioforme

<400> SEQUENCE: 125

Asp Val Cys Met Cys Glu Tyr Thr Asp His Ala His Cys Gly Ile Arg
1               5                   10                  15

Arg Gly Tyr Gln
            20

<210> SEQ ID NO 126
<211> LENGTH: 20
<212> TYPE: PRT
<213> ORGANISM: Chlorobium tepidum

<400> SEQUENCE: 126

Asp Thr Cys Phe Cys Glu Tyr Thr Asp His Gly His Cys Gly Val Arg
1               5                   10                  15

Lys Ser Tyr Gln
            20

<210> SEQ ID NO 127
<211> LENGTH: 20
<212> TYPE: PRT
<213> ORGANISM: Rhodothermus marinus

<400> SEQUENCE: 127

Asp Leu Cys Phe Cys Glu Tyr Thr Asp His Gly His Cys Gly Val Arg
1               5                   10                  15

Lys Thr Tyr Gln
            20

<210> SEQ ID NO 128
<211> LENGTH: 20
<212> TYPE: PRT
<213> ORGANISM: Cytophaga sp.

<400> SEQUENCE: 128

Asp Leu Cys Phe Cys Glu Tyr Thr Asp His Gly His Cys Gly Val Arg
1               5                   10                  15

Lys Ala Tyr Gln
            20

<210> SEQ ID NO 129
<211> LENGTH: 20
<212> TYPE: PRT
<213> ORGANISM: Prochlorococcus marinus

<400> SEQUENCE: 129

Asp Ala Cys Phe Cys Glu Tyr Thr Ala His Gly His Cys Gly Val Arg
1               5                   10                  15

Lys Gly Tyr Gln
            20

<210> SEQ ID NO 130
<211> LENGTH: 20
<212> TYPE: PRT
<213> ORGANISM: Prochlorococcus marinus
```

-continued

```
<400> SEQUENCE: 130

Asp Thr Cys Phe Cys Glu Tyr Thr Ser His Gly His Cys Gly Val Arg
1               5                   10                  15

Lys Ser Tyr Gln
            20

<210> SEQ ID NO 131
<211> LENGTH: 20
<212> TYPE: PRT
<213> ORGANISM: Synechococcus sp.

<400> SEQUENCE: 131

Asp Thr Cys Phe Cys Glu Tyr Thr Ser His Gly His Cys Gly Val Arg
1               5                   10                  15

Lys Thr Tyr Gln
            20

<210> SEQ ID NO 132
<211> LENGTH: 20
<212> TYPE: PRT
<213> ORGANISM: Nostoc sp.

<400> SEQUENCE: 132

Asp Thr Cys Phe Cys Glu Tyr Thr Ser His Gly His Cys Gly Val Arg
1               5                   10                  15

Lys Thr Tyr Gln
            20

<210> SEQ ID NO 133
<211> LENGTH: 20
<212> TYPE: PRT
<213> ORGANISM: Nostoc sp.

<400> SEQUENCE: 133

Asp Thr Cys Phe Cys Glu Tyr Thr Ser His Gly His Cys Gly Val Arg
1               5                   10                  15

Lys Thr Tyr Gln
            20

<210> SEQ ID NO 134
<211> LENGTH: 20
<212> TYPE: PRT
<213> ORGANISM: Nostoc sp.

<400> SEQUENCE: 134

Asp Val Ala Leu Asp Pro Tyr Thr Thr His Gly Gln Asp Gly Val Lys
1               5                   10                  15

Lys Thr Tyr Gln
            20

<210> SEQ ID NO 135
<211> LENGTH: 20
<212> TYPE: PRT
<213> ORGANISM: Synechocystis PCC6803

<400> SEQUENCE: 135

Asp Val Ala Leu Asp Pro Tyr Thr Thr His Gly Gln Asp Gly Val Lys
1               5                   10                  15

Lys Thr Tyr Gln
            20
```